US007205295B2

(12) United States Patent
Barvian et al.

(10) Patent No.: US 7,205,295 B2
(45) Date of Patent: Apr. 17, 2007

(54) BENZOXAZIN-3-ONES AND DERIVATIVES THEREOF AS THERAPEUTIC AGENTS

(75) Inventors: Nicole Barvian, Ann Arbor, MI (US); Christine Nylund Kolz, Dexter, MI (US); Kimberly Suzanne Para, Ann Arbor, MI (US); William Chester Patt, Chelsea, MI (US); Melean Visnick, Ann Arbor, MI (US)

(73) Assignee: Warner-Lambert Company LLC, Morris Plains, NJ (US)

( * ) Notice: Subject to any disclaimer, the term of this patent is extended or adjusted under 35 U.S.C. 154(b) by 203 days.

(21) Appl. No.: 10/730,680

(22) Filed: Dec. 8, 2003

(65) Prior Publication Data

US 2004/0121996 A1 Jun. 24, 2004

Related U.S. Application Data

(60) Provisional application No. 60/431,528, filed on Dec. 6, 2002.

(51) Int. Cl.
C07D 413/10 (2006.01)
C07D 413/14 (2006.01)
A61K 31/5377 (2006.01)

(52) U.S. Cl. .................. 514/230.5; 544/105
(58) Field of Classification Search ............ 544/105; 514/230.5
See application file for complete search history.

(56) References Cited

U.S. PATENT DOCUMENTS

| 4,824,833 | A | 4/1989 | Iijima et al. |
| 5,703,075 | A | 12/1997 | Gammill et al. |
| 6,355,664 | B1 | 3/2002 | Boehringer |
| 6,518,277 | B1 | 2/2003 | Sadhu et al. |
| 2004/0092561 | A1* | 5/2004 | Ruckle et al. ............ 514/369 |

FOREIGN PATENT DOCUMENTS

| EP | 1277738 | 1/2003 |
| WO | WO 00/76987 | 12/2000 |
| WO | WO 00/76988 | 12/2000 |
| WO | WO 01/53266 | 7/2001 |
| WO | WO 01/81346 | 11/2001 |
| WO | WO 04/007491 | 1/2004 |

OTHER PUBLICATIONS

Chalmers (TiPS vol. 17, pp. 166-172 Apr. 1996).*
Abstract of US20040092561A1 (STN printout) 2 pages.*
Chemical Abstract AN: 2003:1957877 CHEMCATS, PD: Jul. 9, 2002.
Chemical Abstract AN: 2003:1940777 CHEMCATS, PD: Jul. 9, 2002.
Chemical Abstract AN: 2003:1940509 CHEMCATS, PD: Jul. 9, 2002.
Chemical Abstract AN: 2003:1940371 CHEMCATS, PD: Jul. 9, 2002.
Chemical Abstract AN: 2002:2995642 CHEMCATS, PD: Jan. 17, 2002.
Chemical Abstract AN: 2002:2977312 CHEMCATS, PD: Jul. 9, 2002.
Chemical Abstract AN: 2002:2647933 CHEMCATS, PD: Jul. 9, 2002.
Chemical Abstract AN: 2002:2272781 CHEMCATS, PD: Jul. 9, 2002.
Chemical Abstract AN: 2002:1467769 CHEMCATS, PD: Jan. 17, 2002.
Chemical Abstract AN: 2002:1464450 CHEMCATS, PD: Jan. 17, 2002.
Chemical Abstract AN: 2002:1461688 CHEMCATS, PD: Jan. 17, 2002.
Chemical Abstract AN: 2002:1460415 CHEMCATS, PD: Jan. 17, 2002.
Chemical Abstract AN: 2002:1458784 CHEMCATS, PD: Jan. 17, 2002.
Chemical Abstract AN: 2002:1455387 CHEMCATS, PD: Jan. 17, 2002.
Alimov, et al., Somatic Mutation and Homozygous Deletion fo PTEN/MMACI Gene 10q23 in Renal Cell Carcinoma, Anticancer Research, 1999, pp. 3841-3846, vol. 19.
Borlando, et al., Increased phosphoinositide 3-kinase activity induces a lymphoproliferative disorder and contributes to tumor generation in vivo, FASEB J., May 2000, pp. 895-903, vol. 14.

(Continued)

Primary Examiner—Kahsay Habte
(74) Attorney, Agent, or Firm—Bryan C. Zielinski; Galina M. Yakovleva

(57) ABSTRACT

The present invention provides compounds of Formula I wherein W, Q, E, D, $R^6$, $R^7$, $R^8$, Y, K, $R^9$, $R^{10}$, $R^{12}$, G, and the double bond denoted "*" have any of the values defined therefore in the specification, and pharmaceutically acceptable salts thereof, that are useful as agents in the treatment of diseases and conditions, including inflammatory diseases, cardiovascular diseases, and cancers. Also provided are pharmaceutical compositions comprising one or more compounds of Formula I.

19 Claims, No Drawings

OTHER PUBLICATIONS

Brass, et al., DNA Amplification on Chromosome 3q26.1-q26.3 in Squamous Cell Carcinoma of the Lung Detected by Reverse Chromosome Painting, Eur. J. Cancer, 1996, pp. 1205-1208, vol. 32A(7), Great Briatin.

Forgacs, et al., Mutation analysis of the PTEN/MMAC1 gene in lung cancer, Oncogene, 1998, pp. 1557-1565, vol. 17.

Hirsch, et al., Central Role for G Protein-Coupled Phosphoinositide 3-Kinase in Inflammation, Science, Feb. 2000, pp. 1049-1053, vol. 287, USA.

Hirsch, et al., Resistance to thromboemolism in PI3K-deficient mice, FASEB Journal, Jul. 2001, pp. 2019-2021, USA.

Hu, et al., Inhibition of Phosphatidylinositol, 3'-Kinase Increases Efficancy of Pactitaxel in in Vitro and in Vivo Ovarian Cancer Models I, Cancer Res., Feb. 2002, pp. 1087-1092, vol. 62.

Jimenez, et al., Identification and characterization of new oncogene derived from the regulatory subunit of phosphoinositide 3-kinase, EMBO Journal, 1998, pp. 743-753, vol. 17(3), USA.

Katso, et al., Cellular Function of phosphoinositide 3-Kinases: Implications for Development, Immunity, Homeostasis, and Cancer, Annu. Rev. Cell Dev. Biol. 2001, pp. 615-675, vol. 17, USA.

Kotelevets, et al., Inhibition by Platelet-activating Factor of Src-and Hepatocyte Growth Factor-dependent Invasiveness of Intestinal and Kidney Epithelial Cells, J. Biol. Chem., Jun. 1998, pp. 14138-14145, vol. 273(23), USA.

Krchak, et al., A solid phase traceless synthesis of quinoxalinones, Tetrahedron Letters, 2000, pp. 2835-2838, USA.

Lee, et al., Solid-phase combinatorial synthesis of 5-arylalkylidene rhodanine, Tetrahedron Letters, 2000, pp. 5729-5732, USA.

Lee, et al., The Raf/MEK/ERK singal transduction cascade as a targe for chemotherapeutic intervention in leuikemia, Leukemia, 2002, pp. 486-507, vol. 16, USA.

Leopoldt, et al., GBY Stimulates Phosphoinositide 3-Kinasey-y by Direct Interaction with Two Domains of the Catalytic p110 Subunit, Dec. 1997, pp. 7024-7029, vol. 273(12), USA.

Ma, et al., PIK3CA as an oncogene in cervical cancer, Oncogene, 2000 pp. 2739-2744, vol. 19.

Nakanishi, et al., Novel Functions of Phosphatidylinositol 3-Kinase in Terminally Differentiated Cells, Cellular Signalling, 1995, pp. 545-557, vol. 6, Great Britain.

Philp, et al., The Phosphatidylinositol 3'-kinase p85a Gene Is an Oncogene in Human Ovarian and Colon Tumors1, Cancer Sesearch, Oct. 2001, pp. 7426-7429, vol. 61, USA.

Shayesteh, et al., PIK3CA is implicated as an oncogene in ovarian cancer, Nature Genetics, Jan. 1999, pp. 99-102, vol. 21.

Susa, et al., Platelet-derived Growth Factor Activates Membrane-associated Phosphatidylinositol 3-Kinase and Mediates Its Translocation from the Cytosol, Nov. 1992. pp. 22951-22956, vol. 267(32), USA.

Vanhaesebroeck, et al., p110, a novel phosphoinositide 3-kinase in leukocytes, Proc. Natl. Acad. Sci., Apr. 1997, pp. 4330-4335, vol. 94, USA.

Vivanco, et al., The Phosphatidylinositol 3-Kinase-Art Pathway in Human Cancer, Nature Reviews Cancer, Jul. 2002, pp. 489-501, vol. 2, USA.

* cited by examiner

BENZOXAZIN-3-ONES AND DERIVATIVES THEREOF AS THERAPEUTIC AGENTS

CROSS-REFERENCES TO RELATED APPLICATIONS

This application claims the benefit of U.S. Provisional Patent application Ser. No. 60/431,528, filed on Dec. 6, 2002, the teachings of which are herein incorporated by reference.

BACKGROUND OF THE INVENTION

Phosphoinositide-3-kinases (PI3Ks) are a family of lipid kinases that phosphorylate phosphoinositols on the 3'-OH to generate PI3P (phosphatidylinositol 3-phosphate), PI-3,4-P2 and PI3,4,5-P3. One class of PI3Ks are stimulated by growth factors (Katso et al. *Annu. Rev. Cell Dev. Biol.* 2001;14: 615–675) and include PI3Kα, PI3Kβ, and PI3Kδ(Vanhaesebroeck et al. *Proc. Natl. Acad. Sci., U.S.A.,* 1997;94:4330–4335; Katso et al., 2001). A separate class of PI3Ks are activated by G-protein coupled receptors and include PI3Kγ. The growth-factor stimulated PI3Ks (e.g., PI3Kα), have been implicated in cellular proliferation and cancer (reviewed in Katso et al., 2001; and Vivanco and Sawyers *Nature Reviews,* 2002;2:489–501). PI3Kγ has been demonstrated to be involved in signaling cascades. For example, PI3Kγ is activated in response to ligands such as C5a, fMLP, ADP, and IL-8. In addition, PI3Kγ has been implicated in immune diseases (Hirsch et al. Science 2000; 287: 1049–1053). PI3Kγ null macrophages show a reduced chemotactic response and a reduced ability to fight inflammation (Hirsch et al. 2000). Furthermore, PI3Kγ has also been implicated in thrombolytic diseases (e.g., thromboembolism, ischemic diseases, heart attacks, and stroke) (Hirsch et al. *FASEB J.* 2000;15(11):2019–2021; and Hirsch et al. *FASEB J., Jul.* 9, 2001;10.1096/fj.00-0810fje (cited herein as Hirsch et al., 2001).

Inhibitors of members of the PI3Ks are being developed for the treatment of human disease (see e.g., WO 01/81346; WO 01/53266; and WO 01/83456). Therefore, there is a need in the art for compounds that can inhibit PI3Ks for use as pharmaceutical agents.

SUMMARY OF THE INVENTION

In one aspect, the present invention provides for compounds of formula I:

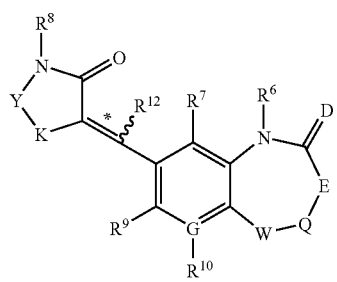

or a pharmaceutically acceptable salt thereof; wherein W is selected from the group consisting of: O, S, and $NR^{21}$; wherein $R^{21}$ is selected from the group consisting of: —H, —$CH_3$, a $C_{1-6}$alkyl, and phenyl; wherein Q is $(CR^2R^3)_n$, wherein $R^2$ and $R^3$ are independently selected from H or —$CH_3$, wherein n is 0 or 1; wherein E is $(CR^4R_5)_p$, wherein $R^4$ and $R^5$ are independently selected from H or —$CH_3$; wherein p is 0 or 1; wherein D is O or S; wherein $R^6$ is selected from the group consisting of H, a $C_{1-9}$alkyl, a —CO—$C_{1-9}$alkyl, a $C_{3-8}$cycloalkyl, a —C(O)—$C_{1-3}$alkylene-$C_{3-8}$cycloalkyl, a ($C_{1-6}$alkyl)-$C_{3-8}$cycloalkyl, a —O—$CH_2$—$C_{3-8}$cycloalkyl, a group of formula -A-B -L, and a group of formula —X—V—U-T; wherein A is absent, or —O—, wherein B is a $C_{1-6}$alkylene, wherein L is —$OR^{24}$, —$C(O)R^{24}$, —$OC(O)R^{24}$, —$C(O)OR^{24}$, —$SO_2$—$R^{24}$, —$NHC(O)R^{24}$, —$NR^{24}R^{26}$; —$C(O)NR^{24}R^{26}$, —$OC(O)NR^{24}R^{26}$, —$NC(O)O\ R^{24}$, a 3- to 8-membered heterocycloalkyl, a 6- to 11-membered bicyclic heterocycloalkyl, a 6- to 9-membered bridged bicyclic heterocycloalkyl, a 5-membered heteroaryl, a 6-membered heteroaryl, an 8- to 12-membered bicyclic heteroaryl, a phenyl, a naphthalenyl or a 9- to 12-membered bicyclic aryl; wherein $R^{24}$ and $R^{26}$ are independently selected from the group consisting of: a $C_{1-6}$alkyl, phenyl, naphthalenyl or a 9- to 12-membered bicyclic aryl, a 5-membered heteroaryl, a 6-membered heteroaryl, an 8- to 12-membered bicyclic heteroaryl, a $C_{1-6}$alkylene-phenyl, C 16alkylene-naphthalenyl or a $C_{1-6}$alkylene-(9- to 12-membered bicyclic aryl), a $C_{1-6}$alkylene-(5-membered heteroaryl), $C_{1-6}$alkylene-(6-membered heteroaryl), a $C_{1-6}$alkylene-(8- to 12-membered bicyclic heteroaryl), $C_{1-6}$alkylene-(3- to 8-membered heterocycloalkyl), $C_{1-6}$alkylene-(6- to 11-membered bicyclic heterocycloalkyl), $C_{1-6}$alkylene-(6- to 9-membered bridged bicyclic heterocycloalkyl), and H ,wherein X is $C_{1-3}$alkylene, —O—$C_{1-3}$alkylene, —$C_{1-3}$alkylene-CO—, —$C_{1-3}$alkylene-C(O)O—, —$C_{1-3}$alkylene-C(O)—$CH_2$—, —$C_1$-$C_3$alkylene-O—, —$C_{1-3}$ alkylene-S(O)—, —$C_{1-3}$ alkylene-S—, or —$C_{1-3}$alkylene-$SO_2$—; wherein V is a 9- to 12-membered bicyclic arylene, a naphthalenylene, a phenylene, a 5-membered heteroarylene, a 6-membered heteroarylene, an 8- to 12-membered bicyclic heteroarylene, a 3- to 8-membered heterocycloalkylene, a 6- to 11-membered bicyclic heterocycloalkylene, or a 6- to 9-membered bridged bicyclic heterocycloalkylene; wherein U is —CO—, —O—, —$CH_2$—O—, a $C_{1-3}$alkenylene, —$(CH_2)_m$—, —O—$CH_2$—, NH—, or is absent, wherein m is an integer from 1 to 3; wherein T is a $C_{3-8}$cycloalkyl, a 9- to 12-membered bicyclic aryl, a naphthalenyl, a phenyl, a 5-membered heteroarylene, a 6-membered heteroarylene, an 8- to 12-membered bicyclic heteroarylene, a piperizinyl, a pyridinyl, a 3- to 8-membered heterocycloalkyl, a 6- to 11-membered bicyclic heterocycloalkyl, a 6- to 9-membered bridged bicyclic heterocycloalkyl, a piperidinyl, a morpholinyl, or an aza-spiro[5.5]undecyl; wherein $R^7$ is H, F, $CF_3$, or $CH_3$; wherein $R^8$ is H, —$CH_2$COOH, phenyl, —$CH_3$, a $C_{1-6}$alkyl, or a $C_{2-6}$alkenyl; wherein Y is C(O), or C(S); wherein K is NH, O, $CH_2$, or S; wherein G is N or C; wherein $R^9$ is H, F, $CF_3$, or $CH_3$; wherein $R^{10}$ is H, —O—$C_{1-3}$alkyl, a $C_{1-3}$alkyl, $NO_2$, $NR^{16}R^{18}$, a S—$C_{1-3}$alkyl, F or Cl, wherein if G is N, then $R^{10}$ is absent, wherein $R^{16}$ and $R^{18}$ are independently selected from the group consisting of: H and $C_{1-3}$alkyl; wherein $R^{12}$ is H, or $C_{1-3}$alkyl; and wherein the stereochemistry of the double bond denoted "*" is entgegen or zusammen. In yet other embodiments, X is a $C_{1-3}$alkylene, and V is a phenylene, naphthalenylene, or a 9- to 12-membered bicyclic arylene. In other embodiments, X is a $C_{1-3}$ alkylene, and V is a 5-membered heteroarylene, a 6-membered heteroarylene, or an 8- to 12-membered bicyclic heteroarylene. In still other embodiments, A is absent, B is a $C_{1-3}$alkylene, L is a 5-membered heteroaryl, a 6-membered heteroaryl, an 8- to 12-membered bicyclic heteroaryl, a phenyl, a naphthalenyl or a 9- to 12-membered bicyclic aryl.

In certain embodiments, W is O, D is O, G is C, n is 1, p is 0, and $R^2$, $R^3$, $R^7$, $R^8$, $R^9$, $R^{10}$, and $R^{12}$ are H-a compound of Formula X:

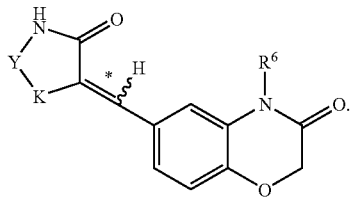

In certain embodiments, $R^6$ is -A-B-L or —X—V—U-T, where L and V are phenyl or a substituted phenyl. In other embodiments, $R^6$ is cyclohexyl or substituted cyclohexyl. Examples of compounds of Formula X include, but are not limited to:

4-(4-tert-Butyl-benzyl)-6-(4-oxo-2-thioxo-thiazolidin-5-ylidenemethyl)-4H-1,4-benzoxazin-3-one;

5-[4-(2,6-Di-tert-butyl-pyridin-4-ylmethyl)-3-oxo-3,4-dihydro-2H-1,4-benzoxazin-6-ylmethylene]-thiazolidine-2,4-dione;

6-(Oxo-2-thioxo-thiazolidin-5-ylidenemethyl)-4-[2-(4-trifluoromethyl-phenyl)-ethyl]-4H-benzo[1,4]oxazin-3-one;

4-(4-Methanesulfonyl-benzyl)-6-(4-oxo-2-thioxo-thiazolidin-5-ylidenemethyl)-4H-1,4-benzoxazin-3-one;

4-(3-tert-Butyl-5-hydroxymethyl-benzyl)-6-(4-oxo-2-thioxo-thiazolidin-5-ylidenemethyl)-4H-1,4-benzoxazin-3-one;

5-[4-(3,5-Di-tert-butyl-4-hydroxy-benzyl)-3-oxo-3,4-dihydro-2H-1,4-benzoxazin-6-ylmethylene]-thiazolidine-2,4-dione;

5-{4-[4-(4-Methyl-piperazin-1-ylmethyl)-benzyl]-3-oxo-3,4-dihydro-2H-1,4-benzoxazin-6-ylmethylene}-thiazolidine-2,4-dione;

4-Cyclohexylmethyl-6-(4-oxo-2-thioxo-oxazolidin-5-ylidenemethyl)-4H-1,4-benzoxazin-3-one;

4-[3-tert-Butyl-5-(morpholine-4-carbonyl)-benzyl]-6-(4-oxo-2-thioxo-thiazolidin-5-ylidenemethyl)-4H-1,4-benzoxazin-3-one;

5-[1-[4-(3-tert-Butyl-5-morpholin-4-ylmethyl-benzyl)-3-oxo-3,4-dihydro-2H-benzo[1,4]oxazin-6-yl]-meth-(Z)-ylidene]-thiazolidine-2,4-dione;

4-(3,5-Difluoro-4-hydroxy-benzyl)-6-(4-oxo-2-thioxo-thiazolidin-5-ylidenemethyl)-4H-benzo[1,4]oxazin-3-one;

5-[4-(3-Chloro-4-fluoro-benzyl)-3-oxo-3,4-dihydro-2H-benzo[1,4]oxazin-6-ylmethylene]-thiazolidine-2,4-dione; and 4-(1-tert-Butyl-5-methyl-1H-pyrazol-3-ylmethyl)-6-(4-oxo-2-hioxo-thiazolidin-5-ylidenemethyl)-4H-benzo[1,4]oxazin-3-one.

In certain embodiments, W is S, D is O, G is C, n is 1, p is 0, and $R^2$, $R^3$, $R^7$, $R^8$, $R^9$, $R^{10}$, and $R^{12}$ are H—a compound of Formula XI:

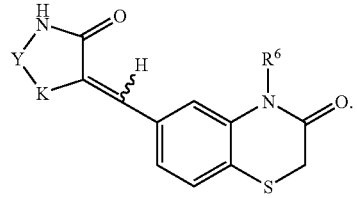

In certain embodiments, $R^6$ is -A-B-L or —X—V—U-T, where L and V are phenyl or a substituted phenyl. In other embodiments, $R^6$ is cyclohexyl or substituted cyclohexyl. Examples of compounds of Formula XI include, but are not limited to:

4-Benzyl-6-(4-oxo-2-thioxo-thiazolidin-5-ylidenemethyl)-4H-1,4-benzothiazin-3-one; and 4-(3,5-Di-tert-butyl-benzyl)-6-(4-oxo-2-thioxo-thiazolidin-5-ylidenemethyl)-4H-1,4-benzothiazin-3-one.

In certain embodiments, W is N, $R^{21}$ is methyl, D is O, G is C, n is 1, p is 0, and $R^2$, $R^3$, $R^7$, $R^8$, $R^9$, $R^{10}$, and $R^{12}$ are H-a compound of Formula XII:

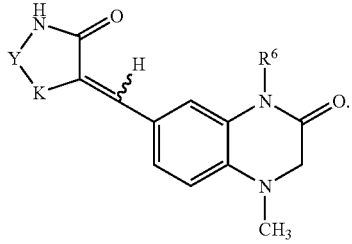

In certain embodiments, $R^6$ is -A-B-L or —X—V—U-T, where L and V are phenyl or a substituted phenyl. In other embodiments, $R^6$ is cyclohexyl or substituted cyclohexyl. Examples of compounds of Formula XII include, but are not limited to:

4-Methyl-7-(4-oxo-2-thioxo-thiazolidin-5-ylidenemethyl)-3,4-dihydro-1H-quinoxalin-2-one; and 1-Benzyl-4-methyl-7-(4-oxo-2-thioxo-thiazolidin-5-ylidenemethyl)-3,4-dihydro-1H-quinoxalin-2-one.

In certain embodiments, W is O, D is O, G is N, n is 1, p is 0, and $R^2$, $R^3$, $R^7$, $R^8$, $R^9$, $R^{10}$, and $R^{12}$ are H-a compound of Formula XIII:

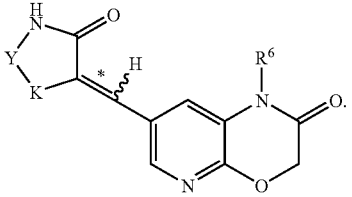

In certain embodiments, $R^6$ is -A-B-L or —X—V—U-T, where L and V are phenyl or a substituted phenyl. In other embodiments, $R^6$ is cyclohexyl or substituted cyclohexyl. Examples of compounds of Formula XIII include, but are not limited to:

1-Benzyl-7-(4-oxo-2-thioxo-thiazolidin-5-ylidenemethyl)-1H-pyrido[2,3-b][1,4]oxazin-2-one; and 7-(4-Oxo-2-thioxo-thiazolidin-5-ylidenemethyl)-1H-pyrido[2,3-b][1,4]oxazin-2-one.

In certain embodiments, W is O, D is O, G is C, n is 1, p is 0, $R^{10}$ is methoxy, and $R^2$, $R^3$, $R^7$, $R^8$, $R^9$, and $R^{12}$ are H—a compound of Formula XIV:

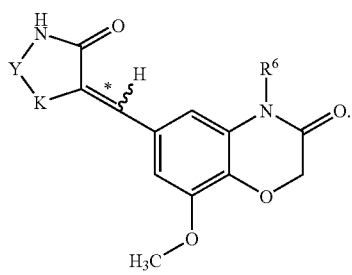

XIV

In certain embodiments, $R^6$ is -A-B-L or —X—V—U-T, where L and V are phenyl or a substituted phenyl. In other embodiments, $R^6$ is cyclohexyl or substituted cyclohexyl. Examples of compounds of Formula XIV include, but are not limited to:

8-Methoxy-6-(4-oxo-2-thioxo-thiazolidin-5-ylidenemethyl)-4H-1,4-benzoxazin-3-one; and 4-(3,5-Di-tert-butyl-benzyl)-8-methoxy-6-(4-oxo-2-thioxo-thiazolidin-5-ylidenemethyl)-4H-1,4-benzoxazin-3-one.

In certain embodiments, W is O, D is O, G is C, n is 1, p is 0, $R^{10}$ is methyl, and $R^2$, $R^3$, $R^7$, $R^8$, $R^9$, and $R^{12}$ are H—a compound of Formula XV:

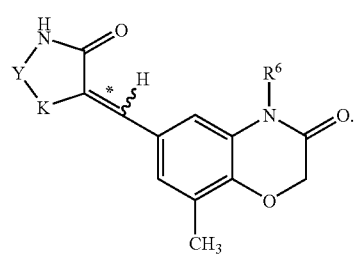

XV

In certain embodiments, $R^6$ is -A-B-L or —X—V—U-T, where L and V are phenyl or a substituted phenyl. In other embodiments, $R^6$ is cyclohexyl or substituted cyclohexyl. Examples of compounds of Formula XV include, but are not limited to:

4-(3,5-Dimethyl-benzyl)-8-methyl-6-(4-oxo-2-thioxo-thiazolidin-5-ylidenemethyl)-4H-1,4-benzoxazin-3-one; and In certain embodiments, W is O, D is O, G is C, n is 1, p is 0, $R^7$ and $R^{10}$ are methyl, and $R^2$, $R^3$, $R^8$, $R^9$, and $R^{12}$ are H—a compound of Formula XVI:

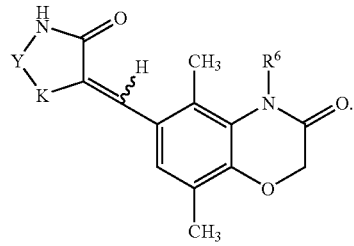

XVI

In certain embodiments, $R^6$ is -A-B-L or —X—V—U-T, where L and V are phenyl or a substituted phenyl. In other embodiments, $R^6$ is cyclohexyl or substituted cyclohexyl. Examples of compounds of Formula XVI include, but are not limited to:

5,8-Dimethyl-6-(4-oxo-2-thioxo-thiazolidin-5-ylidenemethyl)-4H-benzo[1,4]oxazin-3-one.

In certain embodiments, W is O, D is O, G is C, n is 1, p is 0, $R^{10}$ is chloro, and $R^2$, $R^3$, $R^7$, $R^8$, $R^9$, and $R^{12}$ are H—a compound of Formula XVII:

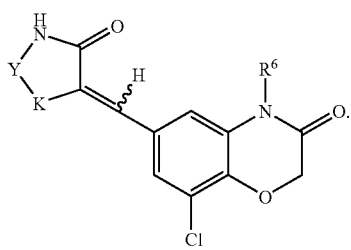

XVII

In certain embodiments, $R^6$ is -A-B-L or —X—V—U-T, where L and V are phenyl or a substituted phenyl. In other embodiments, $R^6$ is cyclohexyl or substituted cyclohexyl. Examples of compounds of Formula XVII include, but are not limited to:

8-Chloro-4-(3,5-di-tert-butyl-benzyl)-6-(4-oxo-2-thioxo-thiazolidin-5-ylidenemethyl)-4H-1,4-benzoxazin-3-one; and 8-Chloro-6-(4-oxo-2-thioxo-thiazolidin-5-ylidenemethyl)-4H-1,4-benzoxazin-3-one.

In certain embodiments, W is O, D is O, G is C, n is 1, p is 0, $R^{10}$ is fluoro, and $R^2$, $R^3$, $R^7$, $R^8$, $R^9$, and $R^{12}$ are H—a compound of Formula XVIII:

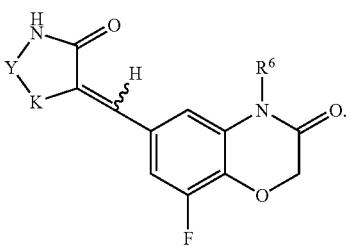

XVIII

In certain embodiments, $R^6$ is -A-B-L or —X—V—U-T, where L and V are phenyl or a substituted phenyl. In other embodiments, $R^6$ is cyclohexyl or substituted cyclohexyl. Examples of compounds of Formula XVIII include, but are not limited to:

5-[1-{4-[3-tert-Butyl-5-(1-hydroxy-1-methyl-ethyl)-benzyl]-8-fluoro-3-oxo-3,4-dihydro-2H-benzo[1,4]oxazin-6-yl}-meth-(Z)-ylidene]-thiazolidine-2,4-dione;

8-Fluoro-4-[4-(1-hydroxy-1-methyl-ethyl)-benzyl]-6-(4-oxo-2-thioxo-thiazolidin-5-ylidenemethyl)-4H-benzo[1,4]oxazin-3-one;

5-[8-Fluoro-4-(4-fluoro-benzyl)-3-oxo-3,4-dihydro-2H-benzo[1,4]oxazin-6-ylmethylene]-thiazolidine-2,4-dione;

4-(3-Chloro-4-fluoro-benzyl)-8-fluoro-6-(4-oxo-2-thioxo-oxazolidin-5-ylidenemethyl)-4H-benzo[1,4]oxazin-3-one;

8-Fluoro-6-(4-oxo-2-thioxo-thiazolidin-5-ylidenemethyl)-4-quinolin-6-ylmethyl-4H-1,4-benzoxazin-3-one; and 4-(3,4-Dichloro-benzyl)-8-fluoro-6-(4-oxo-2-thioxo-thiazolidin-5-ylidenemethyl)-4H-benzo[1,4]oxazin-3-one.

In certain embodiments, W is O, D is O, G is C, n is 1, p is 0, $R^2$ is methyl, and $R^3$, $R^7$, $R^8$, $R^9$, $R^{10}$, and $R^{12}$ are H—a compound of Formula XIX:

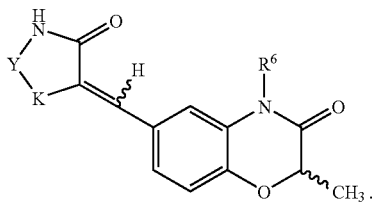

XIX

In certain embodiments, $R^6$ is -A-B-L or —X—V—U-T, where L and V are phenyl or a substituted phenyl. In other embodiments, $R^6$ is cyclohexyl or substituted cyclohexyl. Examples of compounds of Formula XIX include, but are not limited to:

(S)-2-Methyl-6-(4-oxo-2-thioxo-thiazolidin-5-ylidenemethyl)-4H-1,4-benzoxazin-3-one; and (S)-4-Benzyl-2-methyl-6-(4-oxo-2-thioxo-thiazolidin-5-ylidenemethyl)-4H-1,4-benzoxazin-3-one.

In certain embodiments, W is O, D is O, G is C, n is 0, p is 0, and $R^2$, $R^3$, $R^7$, $R^8$, $R^9$, $R^{10}$, and $R^{12}$ are H—a compound of Formula XX:

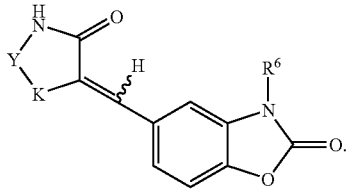

XX

In certain embodiments, $R^6$ is -A-B-L or —X—V—U-T, where L and V are phenyl or a substituted phenyl. In other embodiments, $R^6$ is cyclohexyl or substituted cyclohexyl. Examples of compounds of Formula XX include, but are not limited to:

3-(3,4-Dichloro-benzyl)-5-[4-oxo-2-thioxo-thiazolidin-(5Z)-ylidenemethyl]-3H-benzooxazol-2-one; and 3-Benzyl-5-[4-oxo-2-thioxo-thiazolidin-(5Z)-ylidenemethyl]-3H-benzooxazol-2-one.

In another aspect, the invention provides for pharmaceutical compositions that comprise a therapeutically effective amount of a compound of Formula I; and a pharmaceutically acceptable carrier. In certain embodiments, these compositions are useful in the treatment of a PI3K-mediated disorder or condition. The compounds of the invention can also be combined in a pharmaceutical composition that also comprise compounds that are useful for the treatment of cancer, a thrombolytic disease, heart disease, stroke, an inflammatory disease such as rheumatoid arthritis, or another PI3K-mediated disorder.

In another aspect, the present invention provides for methods of treating a subject suffering from a PI3K-mediated disorder or condition comprising: administering, to a subject suffering from a PI3K-mediated condition or disorder, a pharmaceutical composition comprising a therapeutically effective amount of a compound of Formula I and a pharmaceutically acceptable carrier. In certain embodiments, the PI3K-mediated condition or disorder is selected from the group consisting of: rheumatoid arthritis, ankylosing spondylitis, osteoarthritis, inflammatory diseases, and autoimmune diseases. In other embodiments, the PI3K-mediated condition or disorder is selected from the group consisting of: cardiovascular diseases, atherosclerosis, hypertension, deep venous thrombosis, stroke, myocardial infarction, unstable angina, thromboembolism, pulmonary embolism, thrombolytic diseases, acute arterial ischemia, peripheral thrombotic occlusions, and coronary artery disease. In still other embodiments, the PI3K-mediated condition or disorder is selected from the group consisting of: cancer, small cell lung cancer, squamous cell lung carcinoma, glioma, breast cancer, prostate cancer, ovarian cancer, cervical cancer, and leukemia. In yet another embodiment, the PI3K-mediated condition or disorder is selected from the group consisting of: type II diabetes. In still other embodiments, the PI3K-mediated condition or disorder is selected from the group consisting of: respiratory diseases, bronchitis, asthma, and chronic obstructive pulmonary disease. In certain embodiments, the subject is a human.

Definitions

As used herein, the following terms have the meanings ascribed to them unless specified otherwise.

A "PI3K-mediated disorder or condition" is characterized by the participation of one or more PI3Ks or a PI3P phosphatase, (e.g., PTEN, etc.) in the inception, manifestation of one or more symptoms or disease markers, severity, or progression of a disorder or condition. PI3K-mediated disorders and conditions include, but are not limited to: rheumatoid arthritis, ankylosing spondylitis, osteoarthritis, inflammatory diseases, pulmonary fibrosis, autoimmune diseases, cardiovascular diseases, atherosclerosis, hypertension, deep venous thrombosis, stroke, myocardial infarction, unstable angina, thromboembolism, pulmonary embolism, thrombolytic diseases, acute arterial ischemia, peripheral thrombotic occlusions, coronary artery disease, cancer, breast cancer, gliobastoma, endometrial carcinoma, heptocellular carcinoma, colon cancer, lung cancer, melanoma, renal cell carcinoma, thyroid carcinoma, small cell lung cancer, squamous cell lung carcinoma, glioma, breast cancer, prostate cancer, ovarian cancer, cervical cancer, leukemia, cell lymphoma, lymphoproliferative disorders, type II diabetes, respiratory diseases, bronchitis, asthma, and chronic obstructive pulmonary disease.

A PI3K is an enzyme that is able to phosphorylate the 3'-OH of a phosphoinositol to generate PI3P. PI3Ks include, but are not limited to, PI3Kα, PI3Kβ, PI3Kγ, and PI3Kδ. A PI3K typically comprises at least one catalytic subunit (e.g., p110γ), and may further comprise a regulatory subunit (e.g., p101, etc.).

The term "alkyl group" or "alkyl" includes straight and branched carbon chain radicals. For example, a "$C_{1-6}$ alkyl" is an alkyl group having from 1 to 6 carbon atoms. Examples of straight-chain alkyl groups include, but are not limited to, methyl, ethyl, n-propyl, n-butyl, n-pentyl, n-hexyl, n-heptyl, n-octyl, n-nonyl, n-decyl, etc. Examples of branched-chain alkyl groups include, but are not limited to, isopropyl, tert-butyl, isobutyl, etc.

Moreover, the term alkyl includes both "unsubstituted alkyls" and "substituted alkyls," the latter of which refers to alkyl moieties having substituents replacing a hydrogen on one or more carbons (e.g., replacing a hydrogen on 1, 2, 3, 4, 5, or 6 carbons) of the hydrocarbon backbone. Such substituents can include, but are not limited to, $C_2$–$C_6$-alkenyl, $C_2$–$C_6$-alkynyl, halo, I, Br, Cl, F, —OH, —COOH, sulfhydryl, ($C_1$–$C_6$-alkyl)S—, $C_1$–$C_6$-alkylsulfinyl, nitro, cyano, trifluoromethyl, —NH$_2$, =O, =S, =N—CN, =N—OH, —OCH$_2$F, —OCHF$_2$, —OCF$_3$, —SCF$_3$, —SO$_2$—NH$_2$, $C_1$–$C_6$-alkoxy, —C(O)O—($C_1$–$C_6$ alkyl), —O—C(O)—($C_1$–$C_6$ alkyl), —C(O)—NH$_2$, —C(O)—N(H)—$C_1$–$C_6$ alkyl, —C(O)—N($C_1$–$C_6$ alkyl)$_2$—OC(O)—NH$_2$, —C(O)—H, —C(O)—($C_1$–$C_6$ alkyl), —C(S)—($C_1$–$C_6$ alkyl), —NR$^7$OR$^{72}$, where R$^{70}$ and R$^{72}$ are each independently selected from H, $C_1$–$C_6$-alkyl, $C_2$–$C_6$-alkenyl, $C_2$–$C_6$-alkynyl, and C(O)—$C_1$–$C_6$-alkyl.

Alkyl substituents may also include heterocycloalkyl, heteroaryl, and aryl substituents such as, a ($C_3$–$C_8$)cycloalkyl, a 3- to 8-membered heterocycloalkyl, phenyl, naphthalenyl, benzyl, phenoxy, naphthalenyl-O—, a 9- to 12-membered bicyclic aryl, a 5-membered heteroaryl, 6-membered heteroaryl, and a 8- to 12-membered bicyclic heteroaryl.

Typical substituted alkyl groups thus are aminomethyl, 2-nitroethyl, 4-cyanobutyl, 2,3-dichloropentyl, and 3-hydroxy-5-carboxyhexyl, 2-aminoethyl, pentachloroethyl, trifluoromethyl, 2-diethylaminoethyl, 2-dimethylaminopropyl, ethoxycarbonylmethyl, methanylsulfanylmethyl, methoxymethyl, 3-hydroxypentyl, 2-carboxybutyl, 4-chlorobutyl, and pentafluoroethyl.

"Alkoxy" refers to the alkyl groups mentioned above bound through oxygen, examples of which include methoxy, ethoxy, isopropoxy, tert-butoxy, and the like. In addition, alkoxy refers to polyethers such as O—(CH$_2$)$_2$—O—CH$_3$, and the like. The term "alkoxy" is intended to include both substituted and unsubstituted alkoxy groups. Alkoxy groups can be substituted on carbon atoms with groups such as those set out above for alkyl. Typical substituted alkoxy groups include aminomethoxy, trifluoromethoxy, 2-diethylaminoethoxy, 2-ethoxycarbonylethoxy, 3-hydroxypropoxy, and the like.

"Alkanoyl" groups are alkyl linked through a carbonyl, e.g., $C_1$–$C_6$alkyl-C(O)—. Such groups include formyl, acetyl, propionyl, butyryl, and isobutyryl. The term "alkanoyl" is intended to include both substituted and unsubstituted alkanoyl groups. Alkanoyl groups can be substituted with groups such as those set out above for alkyl.

"Acyl" means an alkyl or aryl (Ar) group bonded through a carbonyl group, i.e., R—C(O)—. For example, acyl includes a $C_1$–$C_6$ alkanoyl, including substituted alkanoyl.

The term "acyl" is intended to include both substituted and unsubstituted acyl groups. Acyl groups can be substituted with groups such as those set out above for alkyl.

"Halo" includes fluoro, chloro, bromo, and iodo.

"Alkenyl" means straight and branched hydrocarbon radicals having 2 or more carbon atoms and comprising at least one double bond and includes ethenyl, 3-buten-1-yl, 2-ethenylbutyl, 3-hexen-1-yl, and the like. The term "alkenyl" is intended to include both substituted and unsubstituted alkenyl groups. A "$C_2$–$C_6$-alkenyl" is an alkenyl group having from from 2 to 6 carbon atoms. Alkenyl groups can be substituted with groups such as those set out above for alkyl.

"Alkynyl" means straight and branched hydrocarbon radicals having 2 or more carbon atoms and comprising at least one triple bond and includes ethynyl, 3-butyn-1-yl, propynyl, 2-butyn-1-yl, 3-pentyn-1-yl, and the like. The term "alkynyl" is intended to include both substituted and unsubstituted alkynyl groups. Alkynyl groups can be substituted with groups such as those set out above for alkyl. In certain embodiments, a straight chain or branched chain alkynyl group has 6 or fewer carbon atoms in its backbone (e.g., $C_2$–$C_6$ for straight chain, $C_3$–$C_6$ for branched chain). The term $C_2$–$C_6$ includes alkynyl groups containing 2 to 6 carbon atoms.

"Carbocycle" or "Cycloalkyl" means a mono or bicyclic carbocyclic ring functional group including, but not limited to, cyclopropyl, cyclobutyl, cyclopentyl, cyclohexyl, cycloheptyl, cyclooctyl, cyclononyl, bicyclo[2.2.1]heptanyl, bicyclo[3.2.1]octanyl, and bicyclo[5.2.0]nonanyl; wherein the cycloalkyl group may optionally contain 1 or 2 double bonds (i.e., a cycloalkylenyl) including, but not limited to, cyclopentenyl, cyclohexenyl, and cycloheptenyl. The term "cycloalkyl" is intended to include both substituted and unsubstituted cycloalkyl groups. Cycloalkyl groups and cyclohexyl groups can be substituted with groups such as those set out above for alkyl. Unless otherwise indicated, the term "($C_3$–$C_8$)cycloalkyl" refers to a cycloalkyl group containing from 3 to 8 carbons. Thus, the term "($C_3$–$C_8$) cycloalkyl" encompasses a monocyclic cycloalkyl group containing from 3 to 8 carbons and a bicyclic cycloalkyl group containing from 6 to 8 carbons.

The phrase "3- to 8-membered heterocycloalkyl" means a stable cyclic group having carbon atoms and 1 to 3 heteroatoms independently selected from S, N or O, wherein when two O atoms or one O atom and one S atom are present, the two O atoms or one O atom and one S atom are not bonded to each other, respectively. Optionally, a 3- to 8-membered heterocycloalkyl may contain 1 or 2 carbon-carbon or carbon-nitrogen double bonds. Illustrative examples of 3- to 8-membered heterocycloalkyl include aziridin-1-yl, 1-oxacyclobutan-2-yl, tetrahydrofuran-3-yl, morpholin-4-yl, 2-thiacyclohex-1-yl, 2-oxo-2-thiacyclohex-1-yl, 2,2-dioxo-2-thiacyclohex-1-yl, and 4-methyl-piperazin-2-yl.

The term "heterocycloalkyl" is intended to include both substituted and unsubstituted heterocycloalkyl groups. Heterocycloalkyl groups can be substituted with 1 to 4 groups such as those set out above for alkyl. Illustrative examples of substituted 3- to 8-membered heterocycloalkyl include 2-hydroxy-aziridin-1-yl, 3-oxo-1-oxacyclobutan-2-yl, 2,2-dimethyl-tetrahydrofuran-3-yl, 3-carboxy-morpholin-4-yl, and 1-cyclopropyl-4-methyl-piperazin-2-yl.

Unless otherwise indicated, the foregoing heterocycloalkyls can be C-attached or N-attached where such is possible and which results in the creation of a stable structure. For example, piperidinyl can be piperidin-1-yl (N-attached) or piperidin-4-yl (C-attached).

Embraced within the term "heterocycloalkyl" are 5 membered rings having one carbon-carbon or one carbon-nitrogen double bond in the ring (e.g., 2-pyrrolinyl, 3-pyrrolinyl, etc.) and 6 membered rings having one carbon-carbon or one carbon-nitrogen double bond in the ring (e.g., dihydro-2H-pyranyl, 1,2,3,4-tetrahydropyridine, 3,4-dihydro-2H-[1,4] oxazine, etc.).

A "3-membered heterocycloalkyl" is a stable 3-membered, monocyclic cycloalkyl ring having 2 carbon atoms and 1 heteroatom selected from the group consisting of: 1 O; 1 S; and 1 N. Illustrative examples of stable 3-membered heterocycloalkyls include oxiranyl, aziridinyl, and thiiranyl.

A "4-membered heterocycloalkyl" is a stable 4-membered, monocyclic cycloalkyl ring having 3 carbon atoms and 1 heteroatom selected from the group consisting of: 1 O; 1 S; and 1 N. Illustrative examples of stable 4-membered heterocycloalkyls include oxetanyl, azetidinyl, and thietanyl.

A "5-membered heterocycloalkyl" is a stable 5-membered, monocyclic cycloalkyl ring having from 1 to 4 carbon atoms and from 1 to 3 heteroatoms selected from the group consisting of: 1 O; 1 S; 1 N; 2 N; 3 N; 1 S and 1 N; 1 S, and 2 N; 1 O and 1 N; and 1 O and 2 N. Illustrative examples of stable 5-membered heterocycloalkyls include tetrahydrofuranyl, dihydrofuranyl, tetrahydrothienyl, dihydrothienyl, imidazolidinyl, oxazolidinyl, imidazolinyl, isoxazolidinyl, pyrrolidinyl, 2-pyrrolinyl, and 3-pyrrolinyl.

A "6-membered heterocycloalkyl" is a stable 6-membered, monocyclic cycloalkyl ring having from 3 to 5 carbon atoms and from 1 to 3 heteroatoms selected from the group consisting of: 1 O; 2 O; 3 O; 1 S; 2 S; 3 S; 1 N; 2 N; 3 N; 1 S, 1 O, and 1 N; 1 S and 1 N; 1 S and 2 N; 1 S and 1 O; 1 S and 2 O; 1 O and 1 N; and 1 O and 2 N. Illustrative examples of stable 6-membered heterocycloalkyls include tetrahydropyranyl, dihydropyranyl, dioxanyl, 1,3-dioxolanyl, 1,4-dithianyl, hexahydropyrimidine, morpholinyl, piperazinyl, piperidinyl, 2H-pyranyl, 4H-pyranyl, pyrazolidinyl, pyrazolinyl, 1,2,3,6-tetrahydropyridinyl, tetrahydrothiopyranyl, thiomorpholinyl, thioxanyl, and trithianyl.

A "7-membered heterocycloalkyl" is a stable 7-membered, monocyclic cycloalkyl ring having from 5 or 6 carbon atoms and from 1 to 3 heteroatoms selected from the group consisting of: 1 O; 2 O; 1 S; 2 S; 1 N; 2 N; 1 S, 1 O, and 1 N; 1 S and 1 N; 1 S and 2 N; 1 S and 1O; 1 S and 2 O; 1 O and 1 N; and 1 O and 2 N. Illustrative examples of stable 7-membered heterocycloalkyls include azepanyl, 2,3,4,5-tetrahydro-1H-azepinyl, oxepanyl, 2,3,4,5-tetrahydro-1H-oxepinyl, thiepanyl, and 2,3,4,5-tetrahydro-1H-thiepinyl.

An "8-membered heterocycloalkyl" is a stable 8-membered, monocyclic cycloalkyl ring having from 5 to 7 carbon atoms and from 1 to 3 heteroatoms selected from the group consisting of: 1 O; 2 O; 3 O; 1 S; 2 S; 3 S; 1 N; 2 N; 3 N; 1 S, 1 O , and 1 N; 1 S and 1 N; 1 S and 2 N; 1 S and 1O; 1 S and 2 O; 1 O and 1 N; and 1 O and 2 N. Illustrative examples of stable 8-membered heterocycloalkyls include azocanyl, thiocanyl, oxocanyl, 3,4,5,6-tetrahydro-2H-oxocinyl, etc.

The term "3- to 8-membered heterocycloalkyl" includes saturated and unsaturated "3- to 8-membered heterocycloalkyls." "3- to 8-membered heterocycloalkyls" may be substituted as set out above for alkyl.

The term "6- to 11-membered bicyclic heterocycloalkyl" refers to a stable ring structure which is either saturated or unsaturated, and which is the result of the fusion of a 5-, 6-, or 7-membered heterocycloalkyl to a 3-, 4-, 5-, 6-, or 7-membered heterocycloalkyl; or a 5-, 6-, or 7-membered heterocycloalkyl to a $C_{3-7}$-cycloalkyl, wherein the fusion junctions are at adjacent ring atoms. The term "6- to 11-membered bicyclic heterocycloalkyl" includes saturated and unsaturated "6- to 11-membered bicyclic heterocycloalkyls." "6- to 11-membered bicyclic heterocycloalkyls" may be substituted as set out above for alkyl. Examples of "6- to 11-membered bicyclic heterocycloalkyls" include 3-azabicyclo[3.1.0]hexanyl, and 3-azabicyclo[4.1.0]-heptanyl.

The term "6- to 9-membered bridged bicyclic heterocycloalkyl" refers to a stable ring structure which is either saturated or unsaturated, and which is the result of the fusion of 5-, 6-, or 7-membered heterocycloalkyl to a 3-, 4-, or 5-membered heterocycloalkyl; or a 5-, 6-, or 7-membered heterocycloalkyl to a $C_{5-7}$-cycloalkyl, wherein the fusion junctions have 1 to 3 intervening ring atoms. The term "6- to 9-membered bridged bicyclic heterocycloalkyl" includes saturated and unsaturated "6- to 9-membered bridged bicyclic heterocycloalkyls." "6- to 9-membered bridged bicyclic heterocycloalkyls" may be substituted as set out above for alkyl. Examples of "6- to 9-membered bridged bicyclic heterocycloalkyls" include 3-azabicyclo[4.2.1]nonanyl and 7-azabicyclo[2.2.1]heptanyl.

An aryl group is an aromatic hydrocarbon radical. Furthermore, the term "aryl" includes multicyclic aryl groups, bicyclic, e.g., naphthyl. Typical aryl groups include phenyl, and naphthyl. Typical substituted aryl groups include 3-chlorophenyl, 2,6-dibromophenyl, 2,4,6-tribromophenyl, 4,7-dichloronaphthyl, 2,6-dichlorophenyl, 3-methoxyphenyl, 4-trifluoromethylphenyl, 3-amino-4-nitrophenyl, 3,5-dihydroxyphenyl, and the like. Unless otherwise indicated, a $C_6$-aryl is a phenyl group. Phenyl may be unsubstituted or substituted at one or more positions with a substituent such as, but not limited to, those substituents described above for alkyl. Naphthalenyl may be unsubstituted or substituted at one or more positions with a substituent such as, but not limited to, those substituents described above for alkyl. The term "aryl" is intended to include both substituted and unsubstituted phenyl groups. An aryl or $C_6$- or $C_{10}$-aryl can be optionally substituted on any ring carbon atom by 1 to 4 functional groups per ring, wherein the substituents are set out above for alkyl.

A "9- to 12-membered bicyclic aryl" is a stable ring structure formed by the fusion of a benzene ring to:

(1) a $C_{5-8}$ monocyclic cycloalkyl (e.g., indanyl; 1,2,3,4-tetrahydro-naphthalenyl; 6,7,8,9-tetrahydro-5H-benzocycloheptenyl, etc.);

(2) a 5- to 7-membered heterocycloalkyl (e.g., benzoxazine, benzthiazine, chromanyl, 1,2,3,4-tetrahydro-quinolinyl, etc.); or (3) another benzene ring (e.g., naphthalenyl);

wherein the fusion junctions are at adjacent carbons on the benzene ring.

A "5-membered heteroaryl" is a stable 5-membered, monocyclic, aromatic ring radial having from 1 to 4 carbon atoms and from 1 to 4 heteroatoms selected from the group consisting of: 1 O; 1 S; 1 N; 2 N; 3 N; 4 N; 1 S and 1 N; 1 S and 2 N; 1 O and 1 N; and 1 O and 2 N. Illustrative examples of stable 5-membered heteroaryls include, but are not limited to, furanyl, 2-furanyl, 3-furanyl, imidazolyl, isoxazolyl, isothiazolyl, oxadiazolyl, oxazolyl, pyridinyl, 2-, 3-, or 4-pyridinyl, pyrimidinyl, 2-, 4-, or 5-pyrimidinyl, pyrazolyl, pyrrolyl, 2- or 3-pyrrolyl, pyrazinyl, pyridazinyl, 3- or 4-pyridazinyl, 2-pyrazinyl, thienyl, 2-thienyl, 3-thienyl, tetrazolyl, thiazolyl, thiadiazolyl, triazinyl and triazolyl.

A "6-membered heteroaryl" is a stable 6-membered, monocyclic, aromatic ring radical having from 3 to 5 carbon atoms and from 1 to 3 heteroatoms selected from the group consisting of: 1 N; 2 N; and 3 N. Illustrative examples of stable 6-membered heteroaryl include pyridin-2-yl, pyridin-4-yl, pyrimidin-2-yl, pyridazin-4-yl, and pyrazin-2-yl.

An "8- to 12-membered bicyclic heteroaryl" is a stable ring structure formed by the fusion of 5- or 6-membered heteroaryl to:
(1) an independently selected 5-membered heteroaryl;
(2) an independently selected 6-membered heteroaryl (e.g., naphthyridinyl, pteridinyl, phthalazinyl, purinyl, etc.);
(3) a $C_{5-8}$ monocyclic cycloalkyl;
(4) a 5- to 7-membered heterocycloalkyl; or
(5) a benzene ring (e.g., benzimidazolyl, benzofuranyl, benzofurazanyl, 2H-1-benzopyranyl, benzothiadiazine, benzothiazinyl, benzothiazolyl, benzothiophenyl, benzoxazolyl, cinnolinyl, furopyridinyl, indolinyl, indolizinyl, indolyl, or 2-, 3-, 4-, 5-, 6-, or 7-indolyl, 3H-indolyl, quinazolinyl, quinoxalinyl, isoindolyl, and isoquinolinyl), wherein the fusion junctions are at adjacent ring atoms. The fusion junctions may be at nitrogen (e.g., indolizine) or carbon atoms in the 5- or 6-membered heteroaryl.

A heteroaryl can also include ring systems substituted on ring carbons with one or more —OH functional groups (which may further tautomerize to give a ring C═O group) and or substituted on a ring sulfur atom by 1 or 2 oxygen atoms to give S═O, or $SO_2$ groups, respectively.

The phrase "pharmaceutical composition" refers to a composition suitable for administration in medical or veterinary use.

The phrase "therapeutically effective amount" means an amount of a compound, or a pharmaceutically acceptable salt thereof, sufficient to inhibit, halt, or cause an improvement in the disorder or condition being treated in a particular subject or subject population. For example in a human or other mammal, a therapeutically effective amount can be determined experimentally in a laboratory or clinical setting, or may be the amount required by the guidelines of the United States Food and Drug Administration, or equivalent foreign agency, for the particular disease and subject being treated.

It should be appreciated that determination of proper dosage forms, dosage amounts, and routes of administration is within the level of ordinary skill in the pharmaceutical and medical arts, and is described below.

Some of the compounds in the present invention may exist as stereoisomers, including enantiomers, diastereomers, and geometric isomers. Geometric isomers include compounds of the present invention that have alkenyl groups, which may exist as entgegen or zusammen conformations, in which case all geometric forms thereof, both entgegen and zusammen, cis and trans, and mixtures thereof, are within the scope of the present invention. Some compounds of the present invention have cycloalkyl groups, which may be substituted at more than one carbon atom, in which case all geometric forms thereof, both cis and trans, and mixtures thereof, are within the scope of the present invention. All of these forms, including (R), (S), epimers, diastereomers, cis, trans, syn, anti, (E), (Z), tautomers, and mixtures thereof, are contemplated in the compounds of the present invention.

The compounds to be used in the present invention can exist in unsolvated forms as well as solvated forms, including hydrated forms. In general, the solvated forms, including hydrated forms, are equivalent to unsolvated forms and are intended to be encompassed within the scope of the present invention.

The compounds of the present invention (e.g., compounds of Formula I) are capable of further forming both pharmaceutically acceptable salts, including but not limited to acid addition and/or base salts. This invention also provides pharmaceutical compositions comprising a compound of Formula I together with a pharmaceutically acceptable carrier, diluent, or excipient therefor. All of these forms can be used in the method of the present invention.

Pharmaceutically acceptable acid addition salts of the compounds of Formula I include salts derived from inorganic acids such as hydrochloric, nitric, phosphoric, sulfuric, hydrobromic, hydriodic, phosphorus, and the like, as well as the salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are the salts of amino acids such as arginate, gluconate, galacturonate, and the like; see, for example, Berge et al., "Pharmaceutical Salts," *J. of Pharmaceutical Science,* 1977;66: 1–19.

The acid addition salts of the basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali and alkaline earth metal hydroxides, or of organic amines. Examples of metals used as cations are sodium, potassium, magnesium, calcium, and the like. Examples of suitable amines are N,N'-dibenzylethylenediamine, chloroprocaine, choline, diethanolamine, ethylenediamine (ethane-1,2-diamine), N-methylglucamine, and procaine; see, for example, Berge et al., supra., 1977.

The base addition salts of acidic compounds are prepared by contacting the free acid form with a sufficient amount of the desired base to produce the salt in the conventional manner. The free acid form may be regenerated by contacting the salt form with an acid and isolating the free acid in a conventional manner. The free acid forms differ from their respective salt forms somewhat in certain physical properties such as solubility in polar solvents, but otherwise the salts are equivalent to their respective free acid for purposes of the present invention.

"Cancer cells," "transformed" cells, or "transformation" in tissue culture, refers to spontaneous or induced phenotypic changes that do not necessarily involve the uptake of new genetic material. Although transformation can arise from infection with a transforming virus and incorporation of new genomic DNA, or uptake of exogenous DNA, it can also arise spontaneously or following exposure to a carcinogen, thereby mutating an endogenous gene. Transformation is associated with phenotypic changes, such as immortalization of cells, aberrant growth control, and/or malignancy (see, Freshney, *Culture of Animal Cells: A Manual of Basic Technique,* 4th ed. Wiley-Liss, Inc., 2000).

The term "subject" refers to a member of the class Mammalia. Examples of mammals include, without limitation, humans, primates, chimpanzees, rodents, mice, rats, rabbits, horses, livestock, dogs, cats, sheep, and cows.

The term "treatment" includes the acute or prophylactic diminishment or alleviation of at least one symptom or characteristic associated or caused by the disorder being treated. For example, treatment can include diminishment of several symptoms of a disorder or complete eradication of a disorder.

The term "administering" refers to the method of contacting a compound with a subject. Modes of "administering" may include but are not limited to, methods that involve contacting the compound intravenously, intraperitoneally, intranasally, transdermally, topically, via implantation, subcutaneously, parentally, intramuscularly, orally, systemically, and via adsorption.

DETAILED DESCRIPTION OF THE INVENTION

I. Introduction

The present invention relates to compounds of Formula I and pharmaceutically acceptable salts thereof:

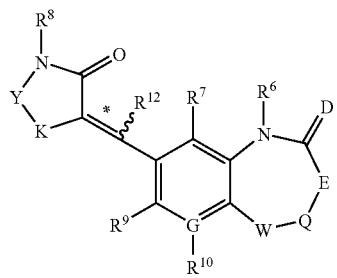

I wherein W, Q, E, D, $R^6$, $R^7$, $R^8$, Y, K, $R^9$, $R^{10}$, $R^{12}$, G, and the double bond denoted "*" have any of the values defined in the specification. Compounds of Formula I, and pharmaceutical compositions thereof, are useful as agents in the treatment of diseases and conditions, including inflammatory diseases, cardiovascular diseases, and cancers. Also disclosed are pharmaceutical compositions comprising one or more compounds of Formula I, processes for preparing compounds of Formula I, and intermediates useful for preparing compounds of Formula I. In particular, compounds of the present invention are useful for the treatment of a PI3K-mediated disorder or condition.

II. Preparation of Compounds

Compounds of the present invention (e.g., compounds of Formula I) can be prepared by applying synthetic methodology known in the art and synthetic methodology outlined in the schemes set forth below.

In Scheme 1, 2 is reacted with a compound 3 R'—O—C(O)—C($R^2R^3$)—$X^e$ (e.g., ethyl bromoacetate (Br—CH$_2$—C(O)O—CH$_2$CH$_3$), in THF with a non-nucleophilic base, e.g., a hydride such as NaH, to give 8. 2 is an appropriately substituted alpha nitrobenzene (e.g., 4-hydroxy-3-nitrobenzaldehyde) or nitropyridine. R' of 3 typically a $C_1$–$C_6$alkyl (e.g., CH$_3$, CH$_2$CH$_3$, t-butyl, etc.) $X^e$ of 3 represents Cl, I, or Br. Unless otherwise noted, group denoted "J" on 2 can be Br, —CHO, —CH$_2$OH, —C(O)CH$_3$, —C(O)$C_1$–$C_6$alkyl, —C(O)$R^{12}$— or —CH$_3$. The groups denoted $R^2$, $R^3$, $R^{10}$, $R^{12}$, and Q are as defined herein. A wavy bond denotes undefined stereochemistry, e.g., R or S; E (entgegen) or Z (zusammen); etc., depending on the context. The nitro moiety of 8 is then treated with a reducing agent such as iron(II)sulfate, zinc metal in acid, tin metal in acid, tin(II) chloride, dithionate; or catalytically with hydrogen gas and a catalyst (e.g., Raney Nickel) to give an amine which cyclizes in situ immediately or upon heating to yield 10.

Alternatively, an appropriately substituted alpha nitrobenzene or nitropyridine 6 (e.g., 5-bromo-2-chloro-3-nitropyridine) can be reacted with 5 (R'—O—C(O)—C($R^2R^3$)—R") in THF with a non-nucleophilic base, e.g., a hydride such as NaH, to yield 8. $X^d$ of 3 represents Cl, I, or Br. R' of 5 is typically a $C_1$–$C_6$alkyl (e.g., CH$_3$, CH$_2$CH$_3$, t-butyl, etc.). R" of 5 is OH or SH. Examples of 5 include, but are not limited to, methylglycolate, methyl(R)-(+)-lactate, and hydroxyacetic acid ethyl ester. A nitropyridine 6 can be provided by reacting an appropriately substituted pyridinol (e.g., 5-bromo-3-nitro-2-pyridinol) in DMF with phosphorus oxychloride.

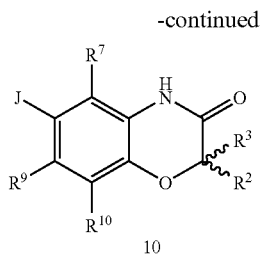

Alternatively, 2 can be reacted with 5 as in Scheme 1b under Mitsunobu conditions (e.g., PPh₃ (triphenylphosphine) and DEAD (diethyl azodicarboxylate) to arrive at 8. The reaction can be carried out with or without the addition of an organic base or inorganic base (e.g., Na₂CO₃, K₂CO₃, NaH, CsCO₃, etc.) in a solvent such as ethanol, acetonitrile, or DMF (dimethylformamide).

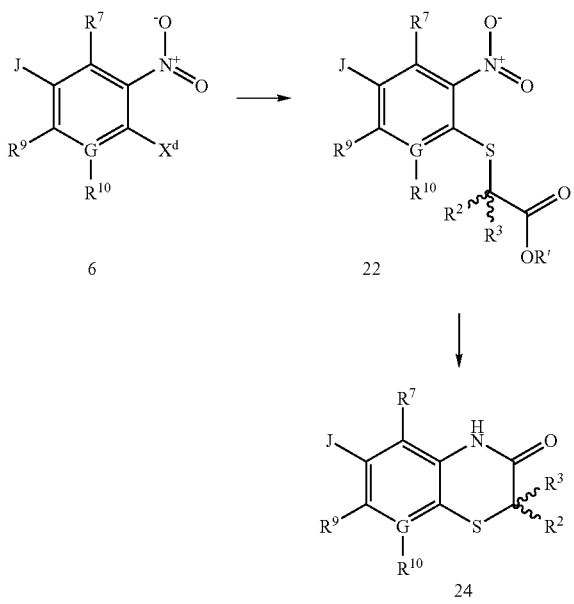

In Scheme 2, compounds of formula 22 can be generated. An appropriately substituted alpha nitrobenzene or nitropyridine 6 (e.g., 4-chloro-3-nitrobenzaldehyde) can be reacted with 21 (HS—C($R^2R^3$)—COOH) (e.g., thioglycolic acid; HS—CH₂—COOH) triethylamine and in acetonitrile to yield 22 (e.g., 4-formyl-2-nitro-phenylsulfanyl)-acetic acid). 22 in ammonium hydroxide is then treated with iron (II) sulfate heptahydrate in water and heated to 90° C. for 1 hour. The iron salts are filtered away, and the filtrate is acidified (e.g., with 6N HCl). The resulting precipitate is then refluxed in ethanol and cooled to provide 24 (e.g, 3-oxo-3,4-dihydro-2H-benzo[1,4]thiazine-6-carboxaldehyde).

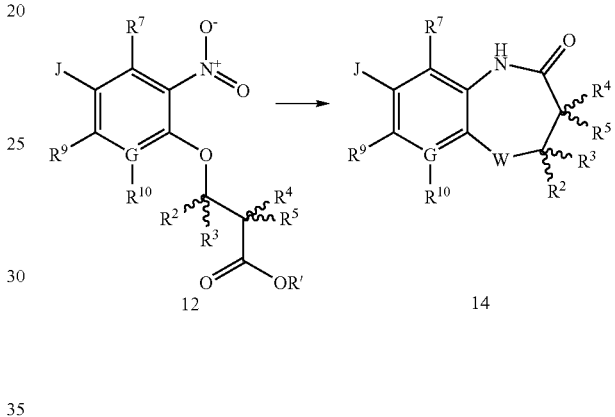

The compounds of formula 12 can be provided by reacting compounds of 2 with 13 (R'—O—C(O)—C($R^2R^3$)—C($R^4R^5$)-Halo) instead of 3 under the same conditions as Scheme 1. R' of 13 is typically a $C_1$-$C_6$alkyl (e.g., CH₃, CH₂CH₃, t-butyl, etc.). Also, 6 (e.g., 5-bromo-2-chloro-3-nitropyridine) can be reacted with a compound 15 (R'—O—C(O)—C($R^2R^3$)—C($R^4R^5$)—R'') (e.g., 3-hydroxy-propionic acid methyl ester), as in Scheme 2 to provide 12. 12 can then be reduced as in Scheme 1 to provide 14. 14 can also be provided by carrying out Scheme 2 using 2 and 15 as starting materials.

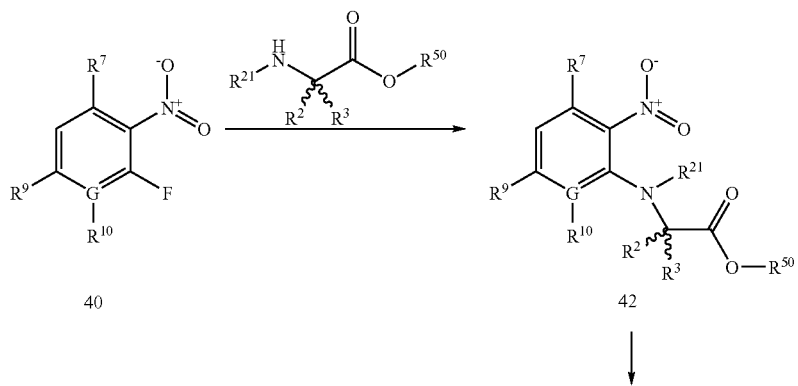

-continued

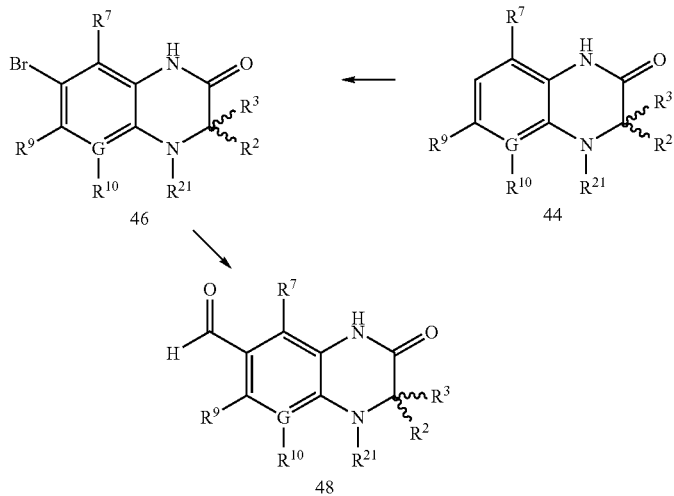

The dihydro-quinoxalin-2-ones or pyrido[2,3-b]pyrazine-2-ones of formula 48 can be synthesized according to Scheme 4. 41 ($R^{21}HN—C(R^2R^3)—C(O)—O—R^{50}$ (e.g., sarcosine t-butyl ester) in acetonitrile with triethylamine is reacted with a 2-halonitrobenzene 40 (e.g., 2-fluoronitrobenzene) to yield 42 (e.g., methyl-(2-nitrophenyl)-amino]acetic acid tert-butylester). $R^{50}$ typically is a $C_1$–$C_6$alkyl (e.g., t-butyl). 42 in methanol is then treated with 20% Pd/C and subjected to a hydrogen atmosphere at a suitable pressure (e.g., 45 psi) to give 44 (e.g., 4-methyl-3,4-dihydro-1H-quinoxalin-2-one). 44 in acetic acid is then contacted with bromine in acetic acid to yield 46 (e.g., 6-bromo-4-methyl-3,4-dihydro-1H-quinoxalin-2-one). 46 is then reacted in DMF with sodium formate and bis(triphenylphosphine)palladium (II) dichloride in the presence of carbon monoxide to give 48 (e.g., 1-methyl-3-oxo-1,2,3,4-tetrahydroquinoxaline-6-carbaldehyde). Alternatively, a compound of formula 43 ($R^{21}HN—C(R^2R^3)—C(R^4R^5)—C(O)—O—R^{50}$) can be reacted in a similar fashion with 40 to arrive at the corresponding benzo[b] [1,4]diazepin-2-one or pyrido[3,4-b][1,4]diazepin-2-one.

When the J group is Br (e.g., 46 or 50), the bromo group can be further reacted as in Scheme 5 with either an alkyl lithium reagent (e.g., t-butyl-Li) at a very low temperature (e.g., −70° C.) in a nonprotic solvent (e.g., THF, ether, etc.) to elicit a bromine-lithium exchange to yield 52 in situ. 52 is then reacted with a dialkylformamide such as DMF (dimethylformamide) to give 54. Alternatively, 50 can be reacted with CO(g) and a palladium catalyst to give 54 directly The conversion of 50 to 54 can also be carried out using sodium formate and bis(triphenylphosphine)palladium (II) dichloride in the presence of carbon monoxide gas.

Scheme 5

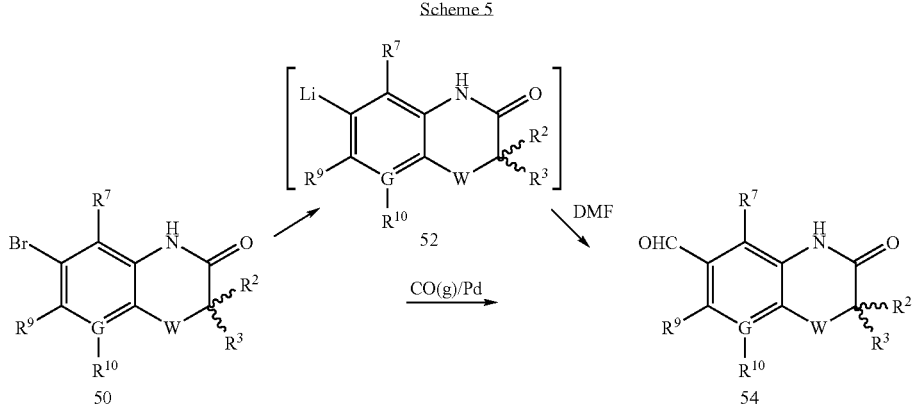

Scheme 6

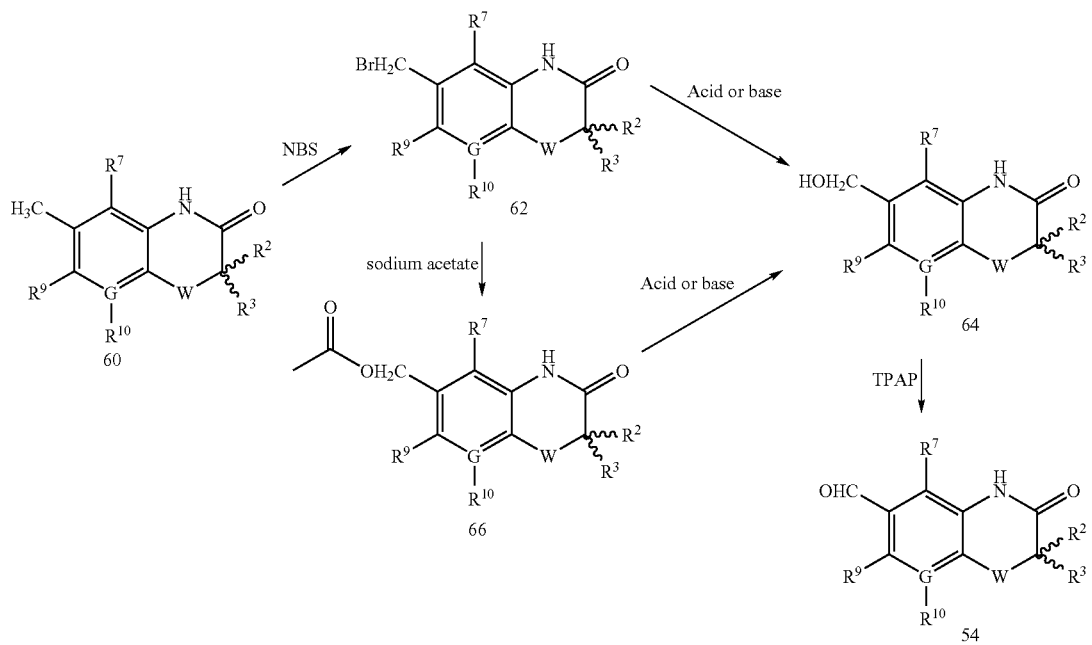

When the J group is methyl (e.g., 60), the methyl group can be halogenated as in Scheme 6 using a reagent such as NBS (N-Bromosuccinimide), NCS(N-chlorosuccinimide), or pyridinium bromide perbromide to yield the bromomethyl intermediate 62. 62 can then be converted to the hydroxymethyl intermediate 64 by treatment with either aqueous acid or aqueous base.

Alternatively, 62 can be reacted with sodium or potassium acetate to give the intermediate acetoxy derivative 66, which can in turn be hydrolyzed with aqueous acid (e.g., acetic acid) or aqueous base to yield 64. Compounds 64 can then be oxidized to the corresponding aldehydes, 54, with an oxidizing reagent such as TPAP (tetrapropylammonium perruthenate), PCC (pyridinium chlorochromate), or PDC (pyridinium dichromate), or under conventional Moffatt oxidation conditions (e.g., DCC(N,N'-Dicyclohexylcarbodiimide) and DMSO), or Swern oxidation conditions (e.g., oxalyl chloride and DMSO).

Scheme 7

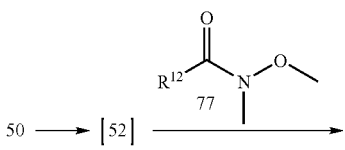

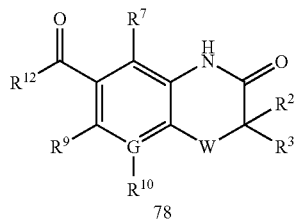

-continued

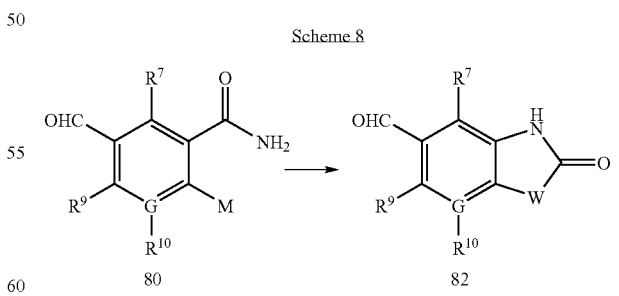

In Scheme 7, the compound 52 is reacted with 77 ($R^{12}$—C(O)—N(OMe)(Me)) and then worked up with acid (e.g., HCl or citric acid, etc.) to arrive at 78. An example of 77 is N-methoxy-N-methyl-acetamide. For the purposes of Scheme 7, $R^{12}$ is a $C_1$–$C_6$alkyl.

Scheme 8

In Scheme 8, an appropriately substituted 80 (e.g., 5-formyl-2-hydroxy-benzamide (Reich et al. *J. Med. Chem.*, 2000;43(9):1670–1683)) can be cyclized in a Hofmann reaction using a base (e.g., potassium hydroxide) and iodobenzene diacetate according to procedures such as those described in Prakash et al. *Synthesis*, 2000;4:541–543 to yield 82. The M group of 80 can be OH, SH, or NR²¹.

Scheme 9

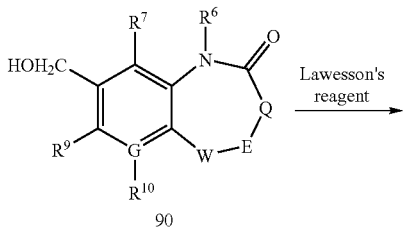

90

Compounds of formula 90 can then be transformed into the corresponding thione 92 as in Scheme 9 with Lawesson's reagent using procedures such as those described in Zhang et al. *Bioorg. & Med. Chem. Lett.*, 2001;11:2747–2750 or with $P_4S_{10}$ using methods that are known in the art. The hydroxymethyl group of 92 can be transformed into the corresponding aldehyde using the methods set out in Scheme 6.

Scheme 10

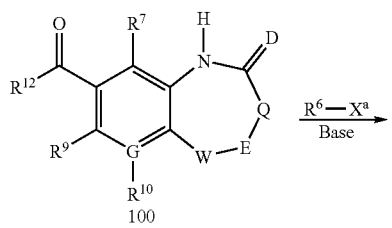

100

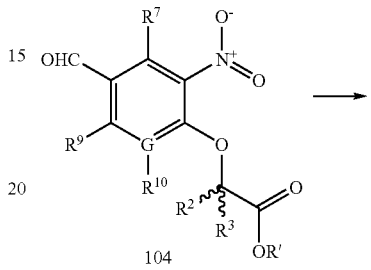

102

In Scheme 10, compounds such as 48, 54, or 100 can then be substituted with a compound of $R^6$—$X^a$, where $X^a$ is Halo, Cl, F, Br, or I, in the presence of a base such as potassium carbonate, cesium carbonate or 2-tert-butylimino-2-diethylamino-1,3-dimethyl-perhydro-1,3,2-diazo-phos-phorine on polystyrene in an organic solvent such as THF, DMF, or acetonitrile to yield intermediate 102. Examples of compounds of $R^6$—$X^a$ include, but are not limited to, iodomethane, phenylethylbromide, methyl 3-(bromomethyl)benzoate, 2-(3,4-dichlorophenyl)ethyl bromide, cyclohexylmethyl bromide, 1-iodo-3-methyl butane, and 3-bromomethyl thiophene.

Scheme 11

104

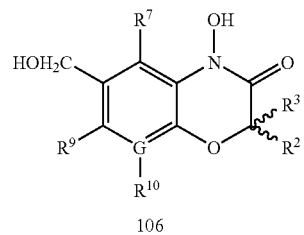

106

108

Compounds of formula 108 can be synthesized using Scheme 11. A compound of 104 is reacted with $NaBH_4$ in a suspension of Pd/C to provide 106. 106 is then reacted with $R^{60}$—$X^a$ (where $X^a$ is a halogen) in the presence of $K_2CO_3$ in acetone to yield 108. The hydroxymethyl group of 108 can be oxidized to the corresponding aldehyde using a reagent such as TPAP as in Scheme 6. Examples of $R^{60}$ include, but are not limited to a $C_1$–$C_6$alkyl, an aryl, a heteroaryl, a cycloalkyl, heterocycloalkyl, etc. Thus, examples of $R^{60}$—$X^a$ include, but are not limited to, iodomethane, phenylethylbromide, methyl 3-(bromomethyl)benzoate, 2-(3,4-dichlorophenyl)ethyl bromide, cyclohexylmethyl bromide, 1-iodo-3-methyl butane, and 3-bromomethyl thiophene. A flouro group as $X^a$ is preferred in $R^{60}$—$X^a$, if $R^{60}$ is a heteroaryl or aryl that is directly attached to $X^a$.

Scheme 12

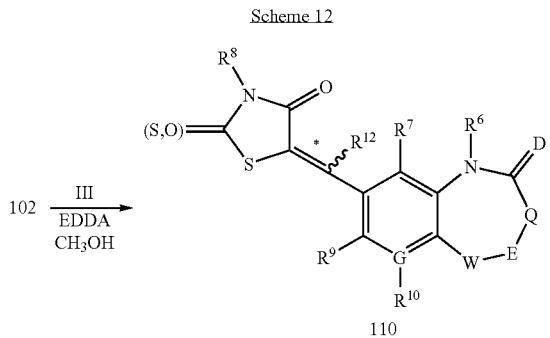

110

In Scheme 12, 102, is reacted with a compound of Formula III containing an activated methylene group, for example: a rhodanine (e.g., rhodanine, rhodanine-3-acetic acid, 3-phenyl rhodanine, etc.) or a thiazolidinedione (e.g., thiazolidinedione, etc.), in the presence of an organic base, such as ethylenediamine diacetate (EDDA), diisopropylethylamine, sodium acetate or pyridine, in the presence of acetic acid and methanol to form a compound 110. Compounds of Formula III are defined herein as a compound having the following structure:

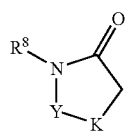

where Y is C(O) or C(S), and K is S. Examples of compounds of Formula III include rhodanine and rhodanine derivatives:

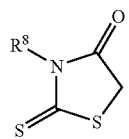

and thiazolidine dione and thiazolidine dione derivatives:

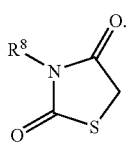

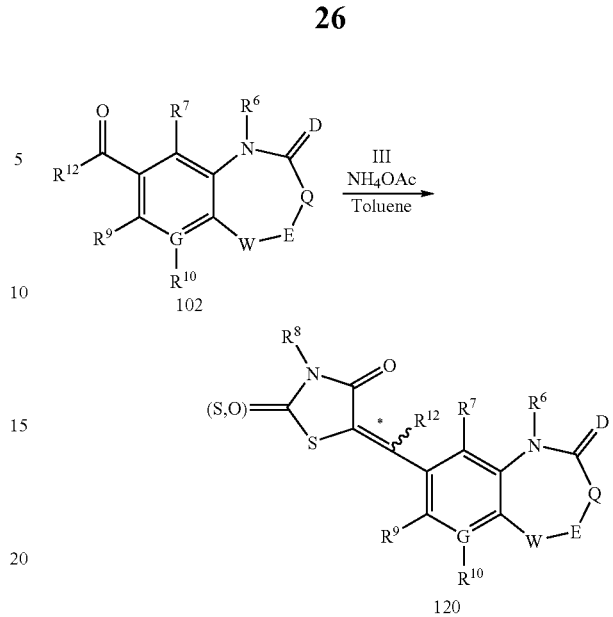

120

Alternatively, in Scheme 13 a Knoevenagel condensation of the active methylene of Formula III with 102 can be carried out to yield 110, using ammonium acetate in toluene and heating to a high temperature (e.g., 110° C.), according to procedures such as those described in Lee and Sun. *Tetrahedron Lett.*, 2000;41:5729–5732. When $R^{12}$ of 102 is H, then the reaction generally can proceed without ammonium acetate (see Zhang and Sun, supra, 2000).

Scheme 14

130

In Scheme 14, 102 is reacted with a compound of Formula IV, such as a imidazolidine-2,4-dione or a 2-thioxo-oxazolidin-4-one, or a 2-thioxo-imidazolidin-4-one in the presence of titanium tetrachloride (TiCl$_4$) and pyridine in THF to form a compound of formula 130. Compounds of Formula IV are defined herein in a compound having the following structure:

where Y is C(O) or C(S), and K is O or NH. Examples of compounds of Formula IV include imidazolidine-2,4-dione and imidazolidine-2,4-dione derivatives:

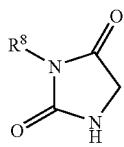

and 2-thioxo-oxazolidin-4-one and 2-thioxo-oxazolidin-4-one derivatives:

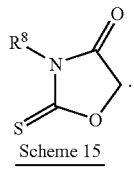

Scheme 15

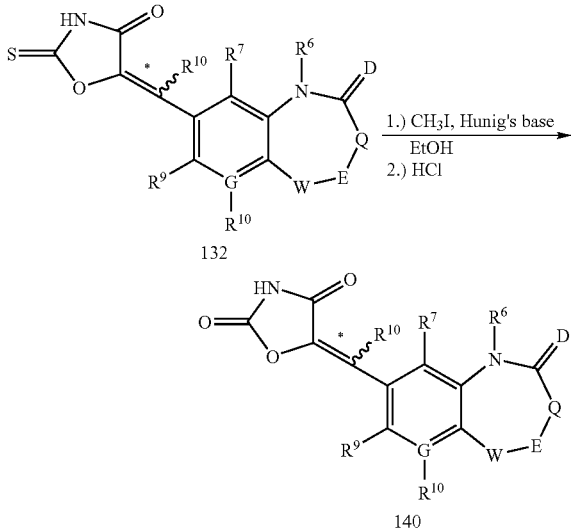

A 2-thioxo-oxazolidin-4-one derivative 132 obtained using Scheme 14 can be converted to an oxazolidine-2,4-dione 140 with iodomethane and Hunig's base in ethanol, followed by concentrated HCl as depicted in Scheme 15.

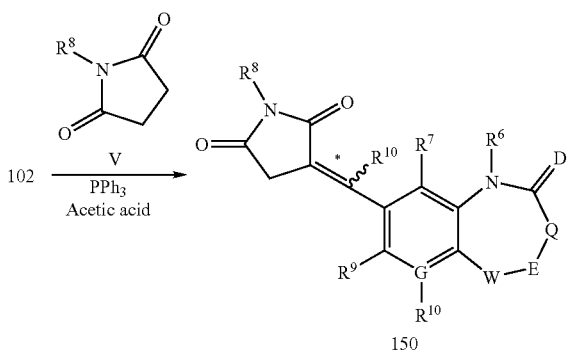

In Scheme 16, 102 is reacted with a compound of Formula V, such as a pyrrolidine-2,5-dione in the presence of triphenylphosphine (PPh$_3$) and acetic acid (AcOH) to form a compound of the formula 150. Compounds of Formula V are defined herein in a compound having the following structure:

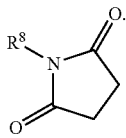

III. Evaluation of Compounds

Compounds of the present invention (e.g., compounds of Formula I and pharmaceutically acceptable salts thereof) can be assayed for their ability to inhibit a PI3K. Examples of these assays are set out below and include in vitro and in vivo assays of PI3K activity.

In certain embodiments of the present invention are compounds that selectively inhibit one or more PI3Ks as compared to one or more enzymes including, but not limited to, a cyclic nucleotide dependent protein kinase, PDGF, a tyrosine kinase, a MAP kinase, a MAP kinase kinase, a MEKK, a cyclin-dependent protein kinase. In other embodiments of the invention are compounds that selectively inhibit one PI3K as compared to another PI3K. For example, in certain embodiments, compounds of the present invention display the ability to selectively inhibit PI3Kγ as compared to PI3Kα or PI3Kβ. A compound selectively inhibits a first enzyme as compared to a second enzyme, when the IC$_{50}$ of the compound towards the first enzyme is less than the IC$_{50}$ of the compound towards the second compound. The IC$_{50}$ can be measured, for example, in an in vitro PI3K assay.

In presently preferred embodiments, compounds of the present invention can be assessed for their ability to inhibit PI3K activity in an in vitro or an in vivo assay (see below).

PI3K assays are carried out in the presence or absence of a PI3K inhibitory compound, and the amount of enzyme activity is compared for a determination of inhibitory activity of the PI3K inhibitory compound.

Samples that do not contain a PI3K inhibitory compound are assigned a relative PI3K activity value of 100. Inhibition of PI3K activity is achieved when the PI3K activity in the presence of a PI3K inhibitory compound is less than the control sample (i.e., no inhibitory compound). The IC$_{50}$ of a compound is the concentration of compound that exhibits 50% of the control sample activity. In certain embodiments, compounds of the present invention have an IC$_{50}$ of less than about 100 μM. In other embodiments, compounds of the present invention have an IC$_{50}$ of about 1 μM or less. In still other embodiments, compounds of the present invention have an IC$_{50}$ of about 200 nM or less.

PI3Kγ assays have been described in the art (see e.g., Leopoldt et al. *J. Biol. Chem.*, 1998;273:7024–7029). Typically, a sample containing a complex of p101 and p110γ protein are combined with Gβ and Gγ proteins (e.g., G protein β$_1$/γ$_2$ subunits). Radiolabeled ATP (e.g., γ-$^{32}$P-ATP) is then added to this mixture. The lipid substrates are formed by creating PIP$_2$ containing lipid micelles. The reactions are then started by adding the lipid and enzyme mixtures and are stopped with the addition of H$_3$PO$_4$. The lipid products are then transferred to a glass fiber filter plate, and washed with H$_3$PO$_4$ several times. The presence of radioactive lipid product (PIP$_3$) can be measured using radiometric methods that are well-known in the art.

The activity of growth factor regulated PI3Ks can also be measured using a lipid kinase assay. For example, PI3Kα can be assayed using samples that contain a regulatory and a catalytic subunit. An activating peptide (e.g., pY peptide, SynPep Corp.) is added to the sample with radiolabeled ATP. $PIP_2$ containing lipid micelles are then added to the sample to start the reaction. The reactions are worked up and analyzed as described for the PI3Kγ assay just described. Assays can also be carried out using cellular extracts (Susa et al. *J. Biol. Chem.*, 1992;267:22951–22956).

IV. Pharmaceutical Compositions

The present invention also provides pharmaceutical compositions comprising a pharmaceutically acceptable carrier or excipient and a compound of the present invention (e.g., a compound of Formula I, or a pharmaceutically acceptable salt thereof). A compound of the present invention can be formulated as a pharmaceutical composition in the form of a syrup, an elixir, a suspension, a powder, a granule, a tablet, a capsule, a lozenge, a troche, an aqueous solution, a cream, an ointment, a lotion, a gel, an emulsion, etc. Preferably, a compound of the present invention will cause a decrease in symptoms or a disease indicia associated with a PI3K-mediated disorder as measured quantitatively or qualitatively.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component. In tablets, the active component is mixed with the carrier having the necessary binding properties in suitable proportions and compacted in the shape and size desired.

The powders and tablets contain from 1% to 95% (w/w) of the active compound. In certain embodiments, the active compound ranges from 5% to 70% (w/w). Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 1000 mg, preferably 1.0 mg to 100 mg, or from 1% to 95% (w/w) of a unit dose, according to the particular application and the potency of the active component. The composition can, if desired, also contain other compatible therapeutic agents.

Pharmaceutically acceptable carriers are determined in part by the particular composition being administered, as well as by the particular method used to administer the composition. Accordingly, there is a wide variety of suitable formulations of pharmaceutical compositions of the present invention (see, e.g., *Remington: The Science and Practice of Pharmacy*, 20th ed., Gennaro et al. Eds., Lippincott Williams and Wilkins, 2000).

A compound of the present invention, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane nitrogen, and the like.

Formulations suitable for parenteral administration, such as, for example, by intravenous, intramuscular, intradermal, and subcutaneous routes, include aqueous and non-aqueous isotonic sterile injection solutions, which can contain antioxidants, buffers, bacteriostats, and solutes that render the formulation isotonic with the blood of the intended recipient, and aqueous and nonaqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. The formulations of compounds can be presented in unit-dose or multi-dose sealed containers, such as ampules and vials. Injection solutions and suspensions can be prepared from sterile powders, granules, and tablets of the kind previously described.

The dose administered to a subject, in the context of the present invention should be sufficient to effect a beneficial therapeutic response in the subject over time. The dose will be determined by the efficacy of the particular compound employed and the condition of the subject, as well as the body weight or surface area of the subject to be treated. The size of the dose also will be determined by the existence, nature, and extent of any adverse side-effects that accompany the administration of a particular compound in a particular subject. In determining the effective amount of the compound to be administered in the treatment or prophylaxis of the disorder being treated, the physician can evaluate factors such as the circulating plasma levels of the compound, compound toxicities, and/or the progression of the disease, etc. In general, the dose equivalent of a compound is from about 1 µg/kg to 10 mg/kg for a typical subject. Many different administration methods are known to those of skill in the art.

For administration, compounds of the present invention can be administered at a rate determined by factors that can include, but are not limited to, the $LD_{50}$ of the compound, the pharmacokinetic profile of the compound, contraindicated drugs, and the side-effects of the compound at various concentrations, as applied to the mass and overall health of the subject. Administration can be accomplished via single or divided doses.

V. Methods for Treating or Preventing PI3K-Mediated Disorders and Conditions

The compounds of the present invention and pharmaceutical compositions comprising a compound of the present invention can be administered to a subject suffering from a PI3K-mediated disorder or condition. PI3K-mediated disorders and conditions can be treated prophylactically, acutely, and chronically using compounds of the present invention, depending on the nature of the disorder or condition. Typically, the host or subject in each of these methods is human, although other mammals can also benefit from the administration of a compound of the present invention.

In therapeutic applications, the compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds described herein can be administered by inhalation, for example, intranasally. Additionally, the compounds of the present invention can be administered transdermally. In certain embodiments, the compounds of the present invention are delivered orally. The compounds can also be delivered rectally, bucally or by insufflation.

The compounds utilized in the pharmaceutical method of the invention can be administered at the initial dosage of about 0.001 mg/kg to about 100 mg/kg daily. In certain embodiments, the daily dose range is from about 0.1 mg/kg to about 10 mg/kg. The dosages, however, may be varied depending upon the requirements of the subject, the severity of the condition being treated, and the compound being employed. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. For convenience, the total daily dosage may be divided and administered in portions during the day, if desired.

The compounds of the invention can also be combined in a pharmacetical composition with compounds that are useful for the treatment of cancer (e.g., cytotoxic drugs such as TAXOL®, taxotere, GLEEVEC® (Imatinib Mesylate), adriamycin, daunomycin, cisplatin, etoposide, a vinca alkaloid, vinblastine, vincristine, methotrexate, or adriamycin, daunomycin, cis-platinum, etoposide, and alkaloids, such as vincristine, farnesyl transferase inhibitors, endostatin and angiostatin, VEGF inhibitors, and antimetabolites such as methotrexate. The compounds of the present invention may also be used in combination with a taxane derivative, a platinum coordination complex, a nucleoside analog, an anthracycline, a topoisomerase inhibitor, or an aromatase inhibitor).

The compounds of the invention can also be combined in a pharmacetical composition with compounds that are useful for the treatment of a thrombolytic disease, heart disease, stroke, etc., (e.g., aspirin, streptokinase, tissue plasminogen activator, urokinase, anticoagulants, antiplatelet drugs (e.g., PLAVIX®; clopidogrel bisulfate), a statin (e.g., LIPITOR® (Atorvastatin calcium), ZOCOR® (Simvastatin), CRESTOR® (Rosuvastatin), etc.), a Beta blocker (e.g, Atenolol), NORVASC® (amlodipine besylate), and an ACE inhibitor (e.g., lisinopril)).

The compounds of the invention can also be combined in a pharmacetical composition with compounds that are useful for the treatment of antihypertension agents such as, ACE inhibitors, lipid lowering agents such as statins, LIPITOR® (Atorvastatin calcium), calcium channel blockers such as NORVASC® (amlodipine besylate). The compounds of the present invention may also be used in combination with fibrates, beta-blockers, NEPI inhibitors, Angiotensin-2 receptor antagonists and platelet aggregation inhibitors.

For the treatment of inflammatory diseases, including rheumatoid arthritis, the compounds of the invention may be combined with agents such as TNF-α inhibitors such as anti-TNFα monoclonal antibodies (such as REMICADE®, CDP-870 and D2E7 (HUMIRA®) and TNF receptor immunoglobulin fusion molecules (such as ENBREL®), IL-1 inhibitors, receptor antagonists or soluble IL-1Rα (e.g. KINERET™ or ICE inhibitors), nonsteroidal anti-inflammatory agents (NSAIDS), piroxicam, diclofenac, naproxen, flurbiprofen, fenoprofen, ketoprofen ibuprofen, fenamates, mefenamic acid, indomethacin, sulindac, apazone, pyrazolones, phenylbutazone, aspirin,COX-2 inhibitors (such as CELEBREX® (celecoxib), VIOXX® (rofecoxib), BEXTRA® (valdecoxib and etoricoxib), metalloprotease inhibitors (preferably MMP-13 selective inhibitors), p2×7 inhibitors, α2δ inhibitors, NEUROTIN®, pregabalin, low dose methotrexate, leflunomide, hydroxychloroquine, d-penicillamine, auranofin or parenteral or oral gold.

The compounds of the invention can also be used in combination with existing therapeutic agents for the treatment of osteoarthritis. Suitable agents to be used in combination include standard non-steroidal anti-inflammatory agents (hereinafter NSAID's) such as piroxicam, diclofenac, propionic acids such as naproxen, flurbiprofen, fenoprofen, ketoprofen and ibuprofen, fenamates such as mefenamic acid, indomethacin, sulindac, apazone, pyrazolones such as phenylbutazone, salicylates such as aspirin, COX-2 inhibitors such as celecoxib, valdecoxib, rofecoxib and etoricoxib, analgesics and intraarticular therapies such as corticosteroids and hyaluronic acids such as hyalgan and synvisc.

The compounds of the invention may also be used in combination with antiviral agents such as Viracept, AZT, aciclovir and famciclovir, and antisepsis compounds such as Valant.

The compounds of the present invention may also be used in combination with CNS agents such as antidepressants (such as sertraline), anti-Parkinsonian drugs (such as deprenyl, L-dopa, Requip, Mirapex, MAOB inhibitors such as selegine and rasagiline, comP inhibitors such as Tasmar, A-2 inhibitors, dopamine reuptake inhibitors, NMDA antagonists, Nicotine agonists, Dopamine agonists and inhibitors of neuronal nitric oxide synthase), and anti-Alzheimer's drugs such as donepezil, tacrine, α2δ inhibitors, NEUROTIN®, pregabalin, COX-2 inhibitors, propentofylline or metryfonate.

The compounds of the present invention may also be used in combination with osteoporosis agents such as EVISTA® (raloxifene hydrochloride) droloxifene, lasofoxifene or fosomax and immunosuppressant agents such as FK-506 and rapamycin.

It is understood that the examples and embodiments described herein are for illustrative purposes only and that various modifications or changes in light thereof will be suggested to persons skilled in the art and are to be included within the spirit and purview of this application and scope of the appended claims.

EXAMPLES

Intermediate 1: (4-Formyl-2-nitro-phenoxy)-acetic acid ethyl ester. To a solution of 4-hydroxy-3-nitrobenzaldehyde (10.0 g, 59.8 mmol) in tetrahydrofuran (600 mL)) and DMF (240 mL) was added dry sodium hydride (1.58 g, 65.82 mmol) and ethyl bromoacetate (7.30 mL, 65.82 mmol). The reaction was refluxed for 24 hours. The reaction was then concentrated and diluted with ethyl acetate (500 mL) and acidified to pH 2 with 1N HCl. The organic layer was then washed with saturated sodium bicarbonate (2×200 mL), sodium chloride (2×200 mL), dried over magnesium sulfate, filtered, and concentrated under reduced pressure to yield a dark red oil. The oil was used in the next step without purification. $^1$H NMR (d$_6$-DMSO) δ 1.18 (t, 3H), 4.15 (q, 2H), 5.14 (s, 2H), 7.49 (d, 1H), 8.11 (dd, 1H), 8.41 (s, 1H), 9.93 (s, 1H). MS: M$^+$−1=252.1 Da.

Intermediate 2: 6-Hydroxymethyl-4H-1,4-benzoxazin-3-one. To a solution of intermediate 1 (6.40 g, 1.67 mmol) in methanol (100 mL) was added Raney nickel (3.0 g). The reaction was then pressurized under an atmosphere of hydrogen to 48 psi for 23 hours. The solution was then filtered through a pad of celite. The celite cake was washed with methanol (200 mL) and concentrated under reduced pressure to yield a brown solid. $^1$H NMR (d$_6$-DMSO) δ 4.36 (s, 2H), 4.50 (s, 2H), 5.12 (s, 1H), 6.62–6.86 (m, 3H). MS: M$^+$−1=178.1 Da.

Intermediate 3: 3-Oxo-3,4-dihydro-2H-benzo[1,4]oxazine-6-carbaldehyde. To a solution of intermediate 2 (2.0 g, 11.2 mmol) in dichloromethane (80 mL) at room temperature was added pyridinium dichromate (6.31 g, 16.8 mmol). The reaction was stirred for 24 hours. The reaction mixture was then filtered through a pad of celite. The celite cake was washed with ethyl ether (100 mL) and ethyl acetate (100 mL). The solution was then concentrated under reduced pressure to yield a dark red solid. $^1$H NMR (d$_6$-DMSO) δ 4.67 (s, 2H), 7.09 (d, 1H), 7.33 (s, 1H), 7.49 (d, 1H), 9.79 (s, 1H). MS: M$^+$−1=175.9 Da.

Example 1

6-(4-Oxo-2-thioxo-thiazolidin-5-ylidenemethyl)-4H-1,4-benzoxazin-3-one.

To a solution of intermediate 3 (0.100 g, 0.565 mmol) in 30 mL of methanol was added ethylenediamine diacetate (EDDA) (0.101 g, 0.565 mmol) followed by rhodanine (0.075 g, 0.565 mmol). The solution was stirred at room temperature for 14 hours, and the resulting yellow precipitate was isolated by filtration, washed with methanol (50 mL) and diethyl ether (50 mL). The solid was air dried to provide the title compound. Microanalysis (C$_{12}$H$_8$N$_2$O$_3$S$_2$): calculated: C=49.30, H=2.76, N=9.58; found: C=47.96, H=2.80, N=9.17. MS: M$^+$−1=291.0 Da.

Intermediate 4: 4-Methyl-3-oxo-3,4-dihydro-2H-1,4-benzoxazine-6-carbaldehyde. To an acetonitrile (20 mL) solution of intermediate 3 (0.202 g, 1.7 mmol) was added iodomethane (0.127 mL, 20.5 mmol), potassium carbonate (0.587 g, 4.25 mmol) followed by benzyltriethylammonium chloride (0.193 g, 0.847 mmol). The reaction was heated to reflux for 4 hours then cooled. The solvent was removed under reduced pressure, and the resulting residue was diluted with ethyl acetate (50 mL) and 1N hydrochloric acid (50 mL). The layers were separated and the organic layer was washed with 1N hydrochloric acid (25 mL), saturated NaHCO$_3$ (25 mL), brine (25 mL), dried over MgSO$_4$, and concentrated under reduced pressure to yield a white solid. $^1$H NMR (CDCl$_3$) δ 3.42 (s, 3H), 4.72 (s, 2H), 7.11 (d, 1H), 7.52–7.55 (m, 2H), 9.91 (s, 1H) ppm. MS: M$^+$−1=191.1 Da.

Example 2

4-Methyl-6-(4-oxo-2-thioxo-thiazolidin-5-ylidenemethyl)-4H-1,4-benzoxazin-3-one.

The title compound was synthesized in a manner analogous to Example 1, from intermediate 4. $^1$H NMR (d$_6$-DMSO) δ 2.48 (s, 3H), 4.73 (s, 2H), 7.12 (d, 1H), 7.21 (d, 1H), 7.37 (s, 1H), 7.61 (s, 1H). MS: M$^+$−1=305.0 Da.

Unless otherwise noted, the following examples were synthesized in a manner analogous to Example 2.

Intermediate 5: (6-Formyl-3-oxo-2,3-dihydro-1,4-benzoxazin-4-yl)-acetic acid tert-butyl ester. The title compound was synthesized in a manner analogous to intermediate 4 using intermediate 3 and tert-butyl bromoacetate. MS: M$^+$−1=291.2 Da.

Intermediate 6: [3-Oxo-6-(4-oxo-thioxox-thiazolidin-5-ylidenemethyl)-2,3-dihydr-benzo[1,4]oxazin-4-yl]-acetic acid tert-butyl ester. The title compound was synthesized in a manner analogous to Example 1, from intermediate 5. MS: M$^+$−1=405.1 Da.

Example 3

[3-Oxo-6-(4-oxo-2-thioxo-thiazolidin-5-ylidenemethyl)-2,3-dihydro-1,4-benzoxazin-4-yl]-acetic acid To solution of intermediate 6 (0.150 g, 0.369 mmol) in dichloromethane (18 mL) at room temperature was added trifluoroacetic acid (6 mL). The solution was stirred for 4.5 hours. The yellow precipitate was isolated by filtration, washed with methanol (50 mL) and diethyl ether (50 mL). The solid was air dried to provide the title compound.

$^1$H NMR (d$_6$-DMSO) δ 4.65 (s, 2H), 4.80 (s, 2H), 7.16 (d, 1H), 7.22 (d, 1H), 7.32 (dd, 1H), 7.58 (s, 1H). MS: M$^+$−1=349.0 Da.

Example 4

4-Benzyl-6-(4-oxo-2-thioxo-thiazolidin-5-ylidenemethyl)-4H-1,4-benzoxazin-3-one

Microanalysis (C$_{19}$H$_{14}$N$_2$O$_3$S$_2$): calculated: C=59.67, H=3.69, N=7.32; found: C=59.07, H=3.92, N=7.25. MS: M$^+$−1=381.1 Da.

Example 5

6-(4-Oxo-2-thioxo-thiazolidin-5-ylidenemethyl)-4-phenethyl-4H-1,4-benzoxazin-3-one Microanalysis ($C_{20}H_{16}N_2O_3S_2$): calculated: C=60.59, H=4.07, N=7.07; found: C=60.02, H=4.16, N=6.86. MS: $M^+-1=395.1$ Da.

Intermediate 7: (4-Formyl-2-methoxy-6-nitro-phenoxy)-acetic acid ethyl ester. To a room temperature solution of 5-nitrovanillin (2.00 g, 10.11 mmol) in tetrahydrofuran (100 mL) was added ethyl glycolate (0.960 mL, 10.11 mmol), triphenylphosphine (3.84 g, 14.65 mmol), and dropwise addition of diethyl azodicarboxylate (2.70 mL, 17.10 mmol). The reaction was stirred overnight at room temperature. The solution was then concentrated in under reduced pressure to yield a crude oil. Purification of the residue by silica gel flash chromatography (20% ethyl acetate/hexane to 40% ethyl acetate/hexane) afforded the title compound. $^1$H NMR ($d_6$-DMSO) δ 1.15 (t, 3H), 3.94 (s, 3H), 4.10 (q, 2H), 4.93 (s, 2H), 7.79 (d, 1H), 8.02 (d, 1H), 9.94 (s, 1H). MS: $M^++1=284.2$ Da.

Intermediate 8: 8-methoxy-3-oxo-3,4-dihydro-2H-1,4-benzoxazine-6-carbaldehyde. The title compound was synthesized in a manner analogous to intermediate 2 and intermediate 3 using intermediate 7. MS: $M^+-1=206.1$ Da.

Example 6

8-Methoxy-6-(4-oxo-2-thioxo-thiazolidin-5-ylidenemethyl)-4H-1,4-benzoxazin-3-one The title compound was synthesized in a manner analogous to Example 1 using intermediate 8. $^1$H NMR ($d_6$-DMSO) δ 3.80 (s, 3H), 4.62 (s, 2H), 6.74 (d, 1H), 7.01 (s, 1H), 7.49 (s, 1H), 10.82 (s, 1H). MS: $M^+-1=321.1$ Da.

Example 7

[3-Oxo-6-(4-oxo-2-thioxo-thiazolidin-5-ylidenemethyl)-2,3-dihydro-1,4-benzoxazin-4-yl]-acetic acid methyl ester $^1$H NMR ($d_6$-DMSO) δ 3.71 (s, 3H), 4.78 (s, 2H), 4.82 (s, 2H), 7.17–7.23 (m, 2H), 7.34 (d, 1H), 7.60(s, 1H). MS: $M^+-1=362.9$ Da.

Example 8

3-[3-Oxo-6-(4-oxo-2-thioxo-thiazolidin-5-ylidenemethyl)-2,3-dihydro-1,4-benzoxazin-4-ylmethyl]-benzoic acid methyl ester $^1$H NMR ($d_6$-DMSO) δ 3.82 (s, 3H), 4.94 (s, 2H), 5.27 (s, 2H), 7.10 (s, 1H), 7.15–7.26 (m, 2H), 7.46–7.55 (m, 3H), 7.86 (d, 1H), 7.98 (s, 1H). MS: $M^+-1=440.0$ Da.

Example 9

4-Biphenyl-4-ylmethyl-6-(4-oxo-2-thioxo-thiazolidin-5-ylidenemethyl)-4H-1,4-benzoxazin-3-one Microanalysis ($C_{25}H_{18}N_2O_3S_2$): calculated: C=65.48, H=3.96, N=6.11; found: C=66.04, H=4.36, N=5.98. MS: $M^+-1=457.1$ Da.

Example 10

[4-Oxo-5-(3-oxo-3,4-dihydro-2H-1,4-benzoxazin-6-ylmethylene)-2-thioxo-thiazolidin-3-yl]-acetic acid; compound with trifluoro-acetic acid The title compound was synthesized in a manner analogous to Example 1 using intermediate 3 and substituting rhodanine-3-acetic acid for rhodanine. $^1$H NMR ($d_6$-DMSO) δ 4.69 (s, 2H), 4.72 (s, 2H), 7.10 (d, 1H), 7.16 (s, 1H), 7.31–7.34 (m, 1H), 7.79 (s, 1H), 10.90 (s, 1H), 13.45 (bs, 1H). MS: $M^+-1=457.1$ Da.

Example 11

4-Naphthalen-2-ylmethyl-6-(4-oxo-2-thioxo-thiazolidin-5-ylidenemethyl)-4H-1,4-benzoxazin-3-one $^1$H NMR ($d_6$-DMSO) δ 4.97 (s, 2H), 5.35 (s, 2H), 7.105–7.23 (m, 3H), 7.43–7.47 (m, 4H), 7.84–7.91 (m, 4H), 13.68 (bs, 1H). MS: $M^+-1=431.1$ Da.

Example 12

6-(4-Oxo-2-thioxo-thiazolidin-5-ylidenemethyl)-4-pyridin-3-ylmethyl-4H-1,4-benzoxazin-3-one $^1$H NMR ($d_6$-DMSO) δ 4.92 (s, 2H), 5.21 (s, 2H), 7.08–7.22 (m, 3H), 7.34–7.37 (m, 1H), 7.52 (s, 1H), 7.71 (d, 1H), 8.47 (d, 1H), 8.59 (s, 1H). MS: $M^+-1=383.2$ Da.

Intermediate 9: (S)-2-(4-Formyl-2-nitro-phenoxy)-propionic acid methyl ester. The title compound was synthesized in a manner analogous to intermediate 7 using 4-hydroxy-3-nitrobenzaldehyde and methyl (R)-(+)-lactate instead of 5-nitrovanillin and ethyl glycolate. MS: $M+-87=166.1$ Da.

Intermediate 10: (S) 2-Methyl-3-oxo-3,4-dihydro-2H-1,4-benzoxazine-6-carbaldehyde. The title compound was synthesized in a manner analogous to intermediate 2 and intermediate 3 using intermediate 9 as starting material.

Example 13

(S)-2-Methyl-6-(4-oxo-2-thioxo-thiazolidin-5-ylidenemethyl)-4H-1,4-benzoxazin-3-one The title compound was synthesized in a manner analogous to Example 1 from intermediate 10. $^1$H NMR ($d_6$-DMSO) δ 1.42 (d, 3H), 4.76–4.81 (q, 1H), 7.08 (m, 2H), 7.23–7.26 (m, 1H), 7.53 (s, 1H). MS: $M^+-1=305.1$ Da.

Example 14

4-(3,5-Dimethyl-benzyl)-6-(4-oxo-2-thioxo-thiazolidin-5-ylidenemethyl)-4H-1,4-benzoxazin-3-one.

$^1$H NMR ($d_6$-DMSO) δ 2.20 (s, 6H), 4.89 (s, 2H), 5.06 (s, 2H), 6.86 (d, 3H), 6.96 (s, 1H), 7.10 (d, 1H), 7.23 (d, 1H), 7.43 (s, 1H). MS: $M^+-1=409.0$ Da.

Example 15

4-(3-Benzyloxy-benzyl)-6-(4-oxo-2-thioxo-thiazolidin-5-ylidenemethyl)-4H-1,4-benzoxazin-3-one Microanalysis ($C_{26}H_{20}N_2O_4S_2$): calculated: C=63.92, H=4.13, N=5.73; found: C=63.88, H=4.14, N=5.74. MS: $M^+-1=487.2$ Da.

Intermediate 11: 4-Hydroxy-2,5-dimethyl-3-nitro-benzaldehyde. To a −10° C. (ice and sodium chloride) solution of 4-hydroxy-2,5-dimethylbenzaldehyde (1.0 g, 6.65 mmol) in concentrated sulfuric acid (10 mL) was added dropwise 70% (concentrated) nitric acid (0.598 g, 6.65 mmol) in 2 mL concentrated sulfuric acid. The reaction stirred for approximately 30 minutes. The reaction was then poured onto crushed ice. The precipitate was collected and washed with water. The solid was then dried on a high vacuum pump to yield a white solid. Microanalysis ($C_9H_9N_1O_4$): calculated: C=55.39, H=4.65, N=7.18; found: C=55.60, H=4.65, N=7.02. MS: $M^+-1$=194.1 Da.

Intermediate 12: (4-Formyl-3,6-dimethyl-2-nitro-phenoxy)-acetic acid ethyl ester. The title compound was synthesized in a manner analogous to intermediate 7 using intermediate 11. Microanalysis ($C_{13}H_{15}N_1O_6$): calculated: C=55.51, H=5.38, N=4.98; found: C=55.60, H=5.30, N=4.94. MS: $M^++1$=282.2 Da.

Intermediate 13: 5,8-Dimethyl-3-oxo-3,4-dihydro-2H-benzo[1,4]oxazine-6-carbaldehyde. The title compound was synthesized in a manner analogous to intermediate 10 using intermediate 12. MS: $M^++1$=204.1 Da.

Example 16

5,8-Dimethyl-6-(4-oxo-2-thioxo-thiazolidin-5-ylidenemethyl)-4H-benzo[1,4]oxazin-3-one.

The title compound was synthesized in a manner analogous to Example 1 starting from intermediate 13. $^1$H NMR ($d_6$-DMSO) δ 2.17 (s, 3H), 2.23 (s, 3H), 4.59 (s, 2H), 6.87 (s, 1H), 7.65 (s, 1H), 10.33 (s, 1H). MS: $M^+-1$=319.1 Da.

Intermediate 14: 3-(6-Formyl-3-oxo-2,3-dihydro-benzo[1,4]oxazine-4-ylmethyl)-benzoic acid methyl ester. The title compound was synthesized in a manner analogous to intermediate 4 using intermediate 3 and methyl 3-(bromomethyl)benzoate. MS: $M^+-1$=325.1 Da.

Intermediate 15: 3-(6-Formyl-3-oxo-2,3-dihydro-1,4-benzoxazin-4-ylmethyl)-benzoic acid. To a tetrahydrofuran solution (25 mL) of intermediate 14 was added 1N lithium hydroxide (2.67 mL, 2.67 mmol). The solution was stirred at room temperature for 7 hours. The reaction was concentrated under reduced pressure and then diluted with ethyl acetate (200 mL) and 1 M hydrochloric acid (25 mL). The layers were separated and the organic layer was washed with saturated sodium chloride (25 mL), dried over $MgSO_4$ and concentrated under reduced pressure to yield the crude product. Purification of the residue by silica gel flash chromatography (50% ethyl acetate/hexane 1% acetic acid) afforded the title compound as a solid. Microanalysis ($C_{17}H_{13}N_1O_5$): calculated: C=65.59, H=4.21, N=4.50; found: C=65.14, H=4.36, N=4.13. MS: $M^+-1$=310.2 Da.

Example 17

3-[3-Oxo-6-(4-oxo-2-thioxo-thiazolidin-5-ylidenemethyl)-2,3-dihydro-1,4-benzoxazin-4-ylmethyl]-benzoic acid The title compound was synthesized in a manner analogous to Example 1 using intermediate 15. Microanalysis ($C_{20}H_{14}N_2O_5S_2$): calculated: C=56.33, H=3.31, N=6.57; found: C=55.33, H=3.22, N=6.54. $^1$H NMR ($d_6$-DMSO) δ 4.94 (s, 1H), 5.25 (s, 1H), 7.14–7.22 (m, 3H), 7.43–7.56 (m, 3H), 7.82 (d, 2H), 7.88 (s, 1H), 12.96 (bs, 1H).

Example 18

(S)-4-Benzyl-2-methyl-6-(4-oxo-2-thioxo-thiazolidin-5-ylidenemethyl)-4H-1,4-benzoxazin-3-one The title compound was synthesized in a manner analogous to Example 2 using intermediate 10. Microanalysis ($C_{20}H_{16}N_2O_3S_2$): calculated: C=60.59, H=4.07, N=7.07; found: C=60.61, H=4.29, N=6.72. MS: $M^+-1$=396.2 Da.

Intermediate 16: 3-Oxo-4-(bromomethyl-benzyl)-3,4-dihydro-2H-benzo[1,4]oxazine-6-carbaldehyde. Cesium carbonate (3.66 g, 11.23 mmol, 2 equiv) was added to a solution of intermediate 3 (0.984 g, 5.56 mmol) and α,α'-dibromo-p-xylene (11.89 g, 45.03 mmol, 8.1 equiv) in dimethylformamide (135 mL). The resulting suspension was stirred at room temperature for 15 hours. The reaction was filtered, the solids were rinsed with DMF, and the resulting filtrate was concentrated to a yellow solid. The residue was dissolved in ethyl acetate and 1 M HCl. The organic layer was separated, washed with $H_2O$ and brine, dried over $MgSO_4$, and concentrated to a pale yellow solid. Flash chromatography of the crude product ($SiO_2$, dichloromethane then 5% diethyl ether in dichloromethane) provided the title compound. $^1$H NMR (DMSO-$d_6$) δ 4.66 (s, 2H), 4.93 (s, 2H), 5.20 (s, 2H) 7.21 (d, 1H), 7.29 (d, 2H), 7.40 (d, 2H) 7.46 (d, 1H), 7.58 (dd, 1H), 9.78 (s, 1H).

Intermediate 17: 3-Oxo-4-(4-piperidin-1-ylmethyl-benzyl)-3,4-dihydro-2H-benzo[1,4]oxazine-6-carbaldehyde. Piperidine (0.200 mL, 2.02 mmol, 2 equiv) was added to a solution intermediate 16 (0.396 g, 1.00 mmol) in $CH_2Cl_2$ (50 mL). The reaction was stirred 18 hours then concentrated to a yellow residue that was partitioned between $Et_2O$ and $H_2O$. The organic layer was washed with brine, dried over $MgSO_4$, and concentrated to a clear, colorless oil which was used without further purification.

Example 19

4-(4-Piperidin-1-ylmethyl-benzyl)-6-(4-oxo-2-thioxo-thiazolidin-5-ylidenemethyl)-4H-1,4-benzoxazin-3-one The title compound was synthesized in a manner analogous to Example 1 starting from intermediate 17.

$^1$H NMR (DMF-$d_7$) δ 1.05–1.15 (m, 2H), 1.25–1.32 (m, 4H), 2.40–2.60 (m, 4H), 3.69 (bs, 2H), 4.54 (s, 2H), 4.92 (s, 2H), 6.71–6.74 (m, 2H), 6.81–6.82 (m, 2H), 7.06 (s, 4H). MS: $M^++1$=480.3 Da.

Example 20

4-(4-Morpholin-4-ylmethyl-benzyl)-6-(4-oxo-2-thioxo-thiazolidin-5-ylidenemethyl)-4H-1,4-benzoxazin-3-one The title compound was synthesized in a manner analogous to Example 19. $^1$H NMR (DMF-$d_7$) δ 2.42 (s, 4H), 3.55 (s, 2H), 3.58 (s, 4H), 4.98 (s, 2H), 5.30 (s, 2H), 7.17–7.19 (m, 2H), 7.28–7.40 (m, 5H), 7.47 (s, 1H). MS: $M^+-1$=480.1 Da.

Example 21

4-(4-Diethylaminomethyl-benzyl)-6-(4-oxo-2-thioxo-thiazolidin-5-ylidenemethyl)-4H-1,4-benzoxazin-3-one The title compound was synthesized in a manner analogous to Example 19. $^1$H NMR (DMF-d$_7$) δ 1.12 (t, 6H), 3.02–3.03 (m, 4H), 4.20 (s, 2H), 4.94 (s, 2H), 5.31 (s, 2H), 7.11–7.14 (m, 2H), 7.20–7.22 (m, 2H), 7.47 (d, 2H), 7.52 (d, 2H). MS: M$^+$−1=466.1 Da.

Example 22

Acetic acid 2-[3-oxo-6-(4-oxo-2-thioxo-thiazolidin-5-ylidenemethyl)-2,3-dihydro-1,4-benzoxazin-4-ylmethyl]-benzyl ester.

$^1$H NMR (DMSO-d$_6$) δ 2.06 (s, 3H), 4.95 (s, 2H), 5.22 (s, 2H), 5.27 (s, 2H) 7.27 (m, 6H), 7.45 (s, 2H). MS: M$^+$−1=453.0 Da.

Example 23

4-(4-Benzyloxy-benzyl)-6-(4-oxo-2-thioxo-thiazolidin-5-ylidenemethyl)-4H-1,4-benzoxazin-3-one $^1$H NMR (DMSO-d$_6$) δ 4.89 (s, 2H), 5.05 (s, 2H), 5.10 (s, 21H), 6.96 (d, 2H), 7.12–7.40 (m, 10H), 7.51 (s, 1H). MS: M$^+$−1=487.1 Da.

Intermediate 18: Acetic acid 2-(6-formyl-3-oxo-2,3-dihydro-benzo[1,4]oxazin-4-ylmethyl)-benzyl ester. The title compound was synthesized in a manner analogous to intermediate 4 using intermediate 3 and acetic acid 2-bromomethyl-benzyl bromide. MS: M$^+$−1=339.1 Da.

Example 24

4-(2-Hydroxymethyl-benzyl)-6-(4-oxo-2-thioxo-thiazolidin-5-ylidenemethyl)-4H-1,4-benzoxazin-3-one To a room temperature tetrahydrofuran solution (50 mL) of intermediate 18 was added 1N lithium hydroxide (0.58 mL), 0.58 mmol). The reaction was stirred overnight at room temperature. The solution was then diluted with ethyl acetate (200 mL) and acidified to pH 2 with 1N hydrochloric acid. The organic layer was separated and washed with H$_2$O (50 mL) and saturated sodium chloride (50 mL). The organic layer was then dried over magnesium sulfate and concentrated under reduced pressure to the crude product. Purification of the residue by silica gel flash chromatography (45% ethyl acetate/hexane) afforded 4-(2-hydroxymethyl-benzyl)-4H-benzo[1,4]oxazine-3-one. MS: M$^+$−1=297.1 Da. The title compound was synthesized in a manner analogous to Example 1 using the above intermediate. Microanalysis (C$_{20}$H$_{16}$N$_2$O$_4$S$_2$): calculated: C=58.24, H=3.91, N=6.79; found: C=57.89, H=4.10, N=6.70. MS: M$^+$−1=412.0 Da.

Example 25

4-[4-(Naphthalen-1-yloxy)-benzyl]-6-(4-oxo-2-thioxo-thiazolidin-5-ylidenemethyl)-4H-1,4-benzoxazin-3-one Microanalysis (C$_{29}$H$_{20}$N$_2$O$_4$S$_2$): calculated: C=66.40, H=3.84, N=5.34; found: C=66.24, H=3.74, N=5.15. MS: M$^+$−1=523.1 Da.

Example 26

4-(3,5-Dimethoxy-benzyl)-6-(4-oxo-2-thioxo-thiazolidin-5-ylidenemethyl)-4H-1,4-benzoxazin-3-one Microanalysis (C$_{21}$H$_{18}$N$_2$O$_5$S$_2$): calculated: C=57.00, H=4.10, N=6.33; found: C=57.08, H=4.00, N=6.09. MS: M$^+$−1=441.0 Da.

Example 27

4-[4-((2S, 6R)-2,6-Dimethyl-piperidin-1-ylmethyl)-benzyl]-6-(4-oxo-2-thioxo-thiazolidin-5-ylidenemethyl)-4H-1,4-benzoxazin-3-one The title compound was synthesized in a manner analogous to Example 19. $^1$H NMR (DMSO-d$_6$) δ 1.29–2.94 (m, 12H), 4.29 (bs, 2H), 4.87 (bs, 2H), 5.19 (bs, 2H), 6.97–7.14 (m, 4H), 7.36–7.48 (m, 4H). MS: M$^+$−1=506.1 Da.

Intermediate 19: (4-Formyl-2-methyl-6-nitro-phenoxy)-acetic acid ethyl ester. 4-Hydroxy-3-methyl-5-nitro-benzaldehyde was synthesized in a manner analogous to intermediate 11 by using 4-hydroxy-3-methylbenzaldehyde instead of 4-hydroxy-2,5-dimethylbenzaldehyde. The title compound was synthesized in a manner analogous to intermediate 9 using 4-hydroxy-3-methyl-5-nitro-benzaldehyde instead of 5-nitrovanillin. MS: M$^+$+1=268.2 Da.

Intermediate 20: 8-Methyl-3-oxo-3,4-dihydro-2H-1,4-benzoxazine-6-carbaldehyde. The title compound was synthesized in a manner analogous to intermediate 2 and intermediate 3 using intermediate 19 as starting material. MS: M$^+$−1=190.1 Da.

Intermediate 21: 4-(3,5-Dimethyl-benzyl)-8-methyl-3-oxo-3,4-dihydro-2H-1,4-benzoxazine-6-carbaldehyde. The title compound was synthesized in a manner analogous to intermediate 4 using intermediate 20 and 3,5-dimethylbenzyl bromide. MS: M$^+$−1=308.1 Da.

Example 28

4-(3,5-Dimethyl-benzyl)-8-methyl-6-(4-oxo-2-thioxo-thiazolidin-5-ylidenemethyl)-4H-1,4-benzoxazin-3-one The title compound was synthesized in a manner analogous to Example 1 using intermediate 21. Microanalysis (C$_{22}$H$_{20}$N$_2$O$_3$S$_2$): calculated: C=62.24, H=4.75, N=6.60; found: C=62.22, H=4.83, N=6.48. MS: M$^+$−1=423.1 Da.

Example 29

4-(3,5-Bis-trifluoromethyl-benzyl)-6-(4-oxo-2-thioxo-thiazolidin-5-ylidenemethyl)-4H-1,4-benzoxazin-3-one Microanalysis (C$_{21}$H$_{12}$N$_2$F$_6$O$_3$S$_2$): calculated: C=48.65, H=2.33, N=5.40; found: C=48.52, H=2.43, N=5.21. MS: M$^+$−1=517.0 Da.

Example 30

4-[2-(3,5-Dimethylphenyl)-ethyl]-6-(4-oxo-2-thioxo-thiazolidin-5-ylidenemethyl)-4H-1,4-benzoxazin-3-one Microanalysis ($C_{22}H_{20}N_2O_3S_2$): calculated: C=62.24, H=4.75, N=6.60; found: C=62.03, H=4.61, N=6.54. MS: $M^+-1$=423.0 Da.

Example 31

4-(2,6-Dimethyl-benzyl)-6-(4-oxo-2-thioxo-thiazolidin-5-ylidenemethyl)-4H-1,4-benzoxazin-3-one Microanalysis ($C_{21}H_{18}N_2O_3S_2$): calculated: C=61.44, H=4.42, N=6.82; found: C=61.01, H=4.27, N=6.70. MS: $M^+-1$=409.0 Da.

Example 32

4-(3,5-Di-tert-butyl-benzyl)-6-(4-oxo-2-thioxo-thiazolidin-5-ylidenemethyl)-4H-1,4-benzoxazin-3-one $^1$H NMR (DMSO-$d_6$) δ 1.20 (s, 18H), 4.90 (s, 2H), 5.15 (s, 2H), 7.11–7.27 (m, 6H), 7.50 (s, 1H), 13.71 (bs, 1H). MS: $M^+-1$=494.1 Da.

Example 33

4-[4-(4-Methyl-piperazin-1-ylmethyl)-benzyl]-6-(4-oxo-2-thioxo-thiazolidin-5-ylidenemethyl)-4H-1,4-benzoxazin-3-one The title product was synthesized in a manner analogous to Example 19. $^1$H NMR (DMSO-$d_6$) δ 2.47 (s, 3H), 2.62–3.31 (m, 4H), 3.53 (bs, 2H), 4.85 (s, 2H), 5.15 (s, 2H), 7.07–7.13 (m, 4H), 7.28 (bs, 4H). MS: $M^+-1$=494.1 Da.

Example 34

6-(4-Oxo-2-thioxo-thiazolidin-5-ylidenemethyl)-4-(3-phenyl-propyl)-4H-1,4-benzoxazin-3-one Microanalysis ($C_{21}H_{18}N_2O_3S_2$): calculated: C=61.44, H=4.42, N=6.82; found: C=61.35, H=4.24, N=6.62. MS: $M^+-1$=410.0 Da.

Example 35

6-(4-Oxo-2-thioxo-thiazolidin-5-ylidenemethyl)-4-[4-(4-phenyl-piperazin-1-ylmethyl)-benzyl]-4H-1,4-benzoxazin-3-one The title compound was synthesized in a manner analogous to Example 19. Microanalysis ($C_{30}H_{28}N_4O_3S_2$): calculated: C=64.73, H=5.07, N=10.06; found: C=64.05, H=4.91, N=10.00. MS: $M^+-1$=556.1 Da.

Example 36

4-(4-tert-Butyl-benzyl)-6-(4-oxo-2-thioxo-thiazolidin-5-ylidenemethyl)-4H-1,4-benzoxazin-3-one Microanalysis ($C_{23}H_{22}N_2O_3S_2$): calculated: C=62.99, H=5.06, N=6.39; found: C=62.88, H=4.90, N=6.21. MS: $M^+-1$=437.0 Da.

Example 37

(S)-4-(3,5-Di-tert-butyl-benzyl)-2-methyl-6-(4-oxo-2-thioxo-thiazolidin-5-ylidenemethyl)-4H-1,4-benzoxazin-3-one The title compound was synthesized in a manner analogous to Example 18. $^1$H NMR (DMSO-$d_6$) δ 1.20 (s, 18H), 1.50 (d, 3H), 5.02–5.20 (m, 3H), 7.07 (s, 2H), 7.16–7.25 (m, 4H), 7.52 (s, 1H). MS: $M^+-1$=508.1 Da.

Intermediate 22: 4-Biphenyl-3-ylmethyl-3-oxo-3,4-dihydro-2H-1,4-benzoxazine-6-carbaldehyde. To a room temperature solution of intermediate 3 in N,N-dimethylformamide (30 mL) was added 2-tert-butylimino-2-diethylamino-1,3-dimethyl-perhydro-1,3,2-diazaphosphorine (BEMP) on polystyrene resin (2.69 g, 5.92 mmol, 2.2 mole/g) followed by 3-phenylbenzyl bromide (0.767 g, 3.10 mmol). The reaction was stirred for 3 hours. The resin was then filtered off, and the reaction was washed with dichloromethane. The solution was concentrated under reduced pressure to yield the crude oil. Purification of the residue by silica gel flash chromatography (25% ethyl acetate/hexane) afforded the title compound as an oil. $^1$H NMR (DMSO-$d_6$) δ 4.96 (s, 2H), 5.27 (s, 2H), 7.19–7.63 (m, 12H), 9.78 (s, 1H). MS: $M^++1$=343.1 Da.

Example 38

4-Biphenyl-3-ylmethyl-6-(4-oxo-2-thioxo-thiazolidin-5-ylidenemethyl)-4H-1,4-benzoxazin-3-one The title compound was synthesized in a manner analogous to Example 1 using intermediate 22. Microanalysis ($C_{25}H_{18}N_2O_3S_2$): calculated: C=65.48, H=3.96, N=6.11; found: C=65.37, H=4.01, N=6.20. MS: $M^+-1$=458.0 Da.

Example 39

4-(3,5-Dimethyl-4-morpholin-4-ylmethyl-benzyl)-6-(4-oxo-2-thioxo-thiazolidin-5-ylidenemethyl)-4H-1,4-benzoxazin-3-one The title compound was synthesized in a manner analogous to Example 19, using 2-tert-butylimino-2-diethylamino-1,3-dimethyl-perhydro-1,3,2-diazaphosphorine on polystyrene resin as in Example 38, instead of cesium carbonate. $^1$H NMR (DMSO-$d_6$) δ 2.26 (s, 6H), 2.47–2.51 (m, 2H), 2.98–3.37 (m, 2H), 3.44–3.55 (m, 6H), 4.75 (s, 2H), 5.19 (s, 2H), 6.89 (d, 1H), 6.96 (s, 2H), 7.12–7.21 (m, 3H). MS: $M^+-1$=509.1 Da.

Example 40

4-(3-Iodo-benzyl)-6-(4-oxo-2-thioxo-thiazolidin-5-ylidenemethyl)-4H-1,4-benzoxazin-3-one The title compound was synthesized in a manner analogous to Example 38. $^1$H NMR (DMSO-$d_6$) δ 4.91 (s, 2H), 5.14 (s, 2H), 7.13–7.16 (m, 2H), 7.23 (d, 1H), 7.31 (d, 1H), 7.49 (s, 1H), 7.62 (d, 2H), 7.72 (s, 1H). MS: $M^+-1$=507.9 Da.

Example 41

4-(3-Bromo-5-iodo-benzyl)-6-(4-oxo-2-thioxo-thia-zolidin-5-ylidenemethyl)-4H-1,4-benzoxazin-3-one The title compound was synthesized in a manner analogous to Example 38. $^1$H NMR (DMSO-$d_6$) δ 4.93 (s, 2H), 5.13 (s, 2H), 7.08 (s, 1H), 7.25 (dd, 2H), 7.52 (d, 1H), 7.71 (s, 1H), 7.84 (s, 1H). MS: $M^+$−1=587.8 Da.

Example 42

4-(3-Methyl-5-morpholin-4-ylmethyl-benzyl)-6-(4-oxo-2-thioxo-thiazolidin-5-ylidenemethyl)-4H-1,4-benzoxazin-3-one The title compound was synthesized in a manner analogous to Example 19. $^1$H NMR (DMSO-$d_6$) δ 2.26 (s, 3H), 2.46 (bs, 6H), 3.52 (bs, 4H), 3.61 (s, 2H), 4.89 (s, 2H), 5.14 (s, 2H), 7.00–7.12 (m, 5H), 7.21 (d, 1H), 7.33 (s, 1H). MS: $M^+$+1=495.1 Da.

Example 43

6-(4-Oxo-2-thioxo-thiazolidin-5-ylidenemethyl)-4-1,1',3',1''-terphenyl-5'-ylmethyl-4H-1,4-benzoxazin-3-one The title compound was synthesized in a manner analogous to Example 38. $^1$H NMR (DMSO-$d_6$) δ 4.94 (s, 2H), 5.29 (s, 2H), 7.11–7.74 (m, 14H).

Example 44

Trifluoro-methanesulfonic acid 3-[3-oxo-6-(4-oxo-2-thioxo-thiazolidin-5-ylidenemethyl)-2,3-dihydro-1,4-benzoxazin-4-ylmethyl]-5-trifluoromethanesulfonyloxy-phenyl ester The title compound was synthesized in a manner analogous to Example 38. Microanalysis ($C_{21}H_{12}F_6N_2O_9S_4$): calculated: C=37.17, H=1.78, N=4.13; found: C=36.73, H=1.64, N=4.04. MS: $M^+$−1=676.9 Da.

Example 45

4-(2,6-Di-tert-butyl-pyridin-4-ylmethyl)-6-(4-oxo-2-thioxo-thiazolidin-5-ylidenemethyl)-4H-1,4-benzoxazin-3-one The title compound was synthesized in a manner analogous to Example 38. Microanalysis ($C_{26}H_{29}N_3O_3S_2$): calculated: C=63.00, H=5.90, N=8.48; found: C=62.85, H=4.84, N=7.71. MS: $M^+$−1=495.1 Da.

Intermediate 23: (2-Fluoro-4-formyl-6-nitro-phenoxy)-acetic acid ethyl ester. 3-fluoro-4-hydroxy-5-nitro-benzaldehyde was synthesized in a manner analogous to intermediate 11 by using 3-fluoro-4-hydroxy-benzaldehyde instead of 4-hydroxy-2,5-dimethylbenzaldehyde. The title compound was synthesized in a manner analogous to intermediate 7 using 3-fluoro-4-hydroxy-5-nitro-benzaldehyde instead of 5-nitrovanillin. MS: $M^+$+1=268.2 Da.

Intermediate 24: 8-Fluoro-3-oxo-3,4-dihydro-2H-1,4-benzoxazine-6-carbaldehyde. Intermediate 23 was reacted to form 8-fluoro-6-hydroxymethyl-4H-benzo[1,4]oxazin-3-one in an analogous manner to intermediate 3. $^1$H NMR (DMSO-$d_6$) δ 4.34 (s, 2H), 4.59 (s, 2H), 6.66 (s, 1H), 6.74 (s, 1H), 6.7 (s, 1H), 10.86 (bs, 1H). To a solution of 8-fluoro-6-hydroxymethyl-4H-benzo[1,4]oxazin-3-one (4.75 g, 24.09 mmol) in dichloromethane (250 mL) at room temperature was added 4-methylmorpholine-N-oxide (4.23 g, 36.1 mmol), TPAP (tetraproplyammonium perruthenate) (0.042 g, 1.2 mmol), and 4A molecular sieves (0.500 g). The reaction was stirred for overnight. The reaction mixture was then filtered through a pad of celite. The celite cake was washed with dichloromethane (100 mL). The solution was then concentrated under reduced pressure to yield a dark oil. This solution was then filtered through $SiO_2$ and washed with ethyl acetate to remove final traces of the TPAP catalyst to yield the title compound. MS: $M^+$−1=194.1 Da.

Example 46

4-Benzyl-8-fluoro-6-(4-oxo-2-thioxo-thiazolidin-5-ylidenemethyl)-4H-1,4-benzoxazin-3-one The title compound was synthesized in a manner analogous to Example 38 using intermediate 24. $^1$H NMR (DMSO-$d_6$) δ 4.97 (s, 2H), 5.15 (s, 2H), 6.87 (s, 1H), 7.20–7.29 (m, 6H), 7.38 (s, 1H). MS: $M^+$−1=400.1 Da.

Intermediate 25: (2-Chloro-4-formyl-6-nitro-phenoxy)-acetic acid ethyl ester. 3-Chloro-4-hydroxy-5-nitro-benzaldehyde was synthesized in a manner analogous to intermediate 11 by using 3-chloro-4-hydroxybenzaldehyde instead of 4-hydroxy-2,5-dimethylbenzaldehyde. The title compound was synthesized in a manner analogous to intermediate 7 using (2-chloro-4-formyl-6-nitro-phenoxy)-acetic acid ethyl ester instead of 5-nitrovanillin. Microanalysis ($C_{11}H_{10}Cl_1N_1O_6$): calculated: C=45.93, H=3.50, N=4.87; found: C=46.07, H=3.52, N=4.85.

Intermediate 26: 8-Chloro-3-oxo-3,4-dihydro-2H-1,4-benzoxazine-6-carbaldehyde. The title compound was synthesized in a manner analogous to intermediate 2 and intermediate 3 using intermediate 25. MS: $M^+$−1=210.1 Da.

Example 47

8-Chloro-4-(3,5-di-tert-butyl-benzyl)-6-(4-oxo-2-thioxo-thiazolidin-5-ylidenemethyl)-4H-1,4-benzoxazin-3-one. The title compound was synthesized in a manner analogous to Example 38 using intermediate 26. $^1$H NMR (DMF-$d_7$) δ 1.24 (s, 18H), 5.14 (s, 2H), 5.30 (s, 2H), 7.14 (s, 1H), 7.24 (s, 2H), 7.36 (s, 1H), 7.46 (s, 1H), 7.51 (s, 1H). MS: $M^+$−1=528.2 Da.

Example 48

4-[3-(4-Methyl-piperazin-1-ylmethyl)-benzyl]-6-(4-oxo-2-thioxo-thiazolidin-5-ylidenemethyl)-4H-1,4-benzoxazin-3-one The title compound was synthesized in a manner analogous to Example 19. $^1$H NMR (DMSO-$d_6$) δ 2.62 (m, 3H), 2.74–3.30 (m, 8H), 3.57 (bs, 2H), 4.84 (s, 2H), 5.14 (s, 2H), 7.03–7.17 (m, 6H), 7.26 (t, 1H), 7.35 (s, 1H). MS: $M^+$−1=494.2 Da.

Example 49

8-Chloro-6-(4-oxo-2-thioxo-thiazolidin-5-ylidenemethyl)-4H-1,4-benzoxazin-3-one

The title compound was synthesized in a manner analogous to Example 47. Microanalysis ($C_{12}H_{13}Cl_1N_2O_3S_2$): calculated: C=44.11, H=2.16, N=8.57; found: C=44.20, H=2.04, N=7.56. MS: $M^+-1=325.0$ Da.

Example 50

4-Benzyl-8-chloro-6-(4-oxo-2-thioxo-thiazolidin-5-ylidenemethyl)-4H-1,4-benzoxazin-3-one The title compound was synthesized in a manner analogous to Example 47. Microanalysis ($C_{19}H_{13}Cl_1N_2O_3S_2$): calculated: C=54.74, H=3.14, N=6.72; found: C=54.64, H=3.62, N=5.70. MS: $M^+-1=416.1$ Da.

Example 51

4-(3,5-Di-tert-butyl-benzyl)-8-methoxy-6-(4-oxo-2-thioxo-thiazolidin-5-ylidenemethyl)-4H-1,4-benzoxazin-3-one The title compound was synthesized in a manner analogous to Example 6 using BEMP resin as in intermediate 22. Microanalysis ($C_{28}H_{32}N_2O_4S_2$): calculated: C=64.10, H=6.15, N=5.34; found: C=63.64, H=5.79, N=4.88. MS: $M^+-1=524.2$ Da.

Example 52

4-(3-tert-Butyl-5-iodo-benzyl)-6-(4-oxo-2-thioxo-thiazolidin-5-ylidenemethyl)-4H-1,4-benzoxazin-3-one The title compound was synthesized in a manner analogous to Example 38. $^1$H NMR (DMSO-$d_6$) δ 1.20 (s, 18H), 4.90 (s, 2H), 5.12 (s, 2H), 7.10 (s, 1H), 7.20 (dd, 2H), 7.36 (s, 1H), 7.41 (s, 1H), 7.48 (s, 1H), 7.55 (s, 1H). MS: $M^+-1=564.0$ Da.

Example 53

8-Fluoro-6-(4-oxo-2-thioxo-thiazolidin-5-ylidenemethyl)-4H-1,4-benzoxazin-3-one

The title compound was synthesized in a manner analogous to Example 1 using intermediate 24. $^1$H NMR (DMSO-$d_6$) δ 4.70 (s, 2H), 6.87 (s, 2H), 7.24 (d, 1H), 7.45 (s, 1H). MS: $M^+-1=309.0$ Da.

Example 54

4-(3,5-Di-tert-butyl-benzyl)-8-fluoro-6-(4-oxo-2-thioxo-thiazolidin-5-ylidenemethyl)-4H-1,4-benzoxazin-3-one The title compound was synthesized in a manner analogous to Example 46. Microanalysis ($C_{27}H_{29}F_1N_2O_3S_2$): calculated: C=63.26, H=5.70, N=5.46; found: C=62.96, H=5.74, N=5.40. MS: $M^+-1=512.2$ Da.

Intermediate 27: 4-(3-tert-Butyl-5-iodo-benzyl)-3-oxo-3,4-dihydro-2H-1,4-benzoxazine-6-carbaldehyde. The title compound was synthesized in a manner analogous to intermediate 22 using intermediate 3 and 1-bromomethyl-3-tert-butyl-5-iodo-benzene. MS: $M^+-1=449.0$ Da.

Intermediate 28: 3-tert-Butyl-5-(6-formyl-3-oxo-2,3-dihydro-1,4-benzoxazin-4-ylmethyl)-benzonitrile. To a N,N-dimethylformamide (10 mL) solution of intermediate 27 (0.500 g, 1.11 mmol) was added zinc cyanide (0.078 g, 0.66 mmol) and tetrakis(triphenylphosphine)palladium (0) (0.051 g, 0.04 mmol). The reaction was heated to 80° C. for 5.5 hours. The reaction was cooled to room temperature, filtered through a pad of celite, and diluted with ethyl acetate. The organic layer was washed with 10% ammonium hydroxide (1×20 mL) and brine (1×20 mL). The organic layer was dried over MgSO$_4$, filtered and then concentrated in under reduced pressure to yield a crude oil. This material was chromatographed using 20% ethyl acetate/hexane to yield the title compound MS: $M^+-1=348.2$ Da.

Example 55

3-tert-Butyl-5-[3-oxo-6-(4-oxo-2-thioxo-thiazolidin-5-ylidenemethyl)-2,3-dihydro-1,4-benzoxazin-4-ylmethyl]-benzonitrile The title compound was synthesized in a manner analogous to Example 1 using intermediate 28. Microanalysis ($C_{24}H_{21}N_3O_3S_2$): calculated: C=62.18, H=4.57, N=9.06; found: C=61.64, H=4.73, N=8.99. MS: $M^+-1=463.1$ Da.

Intermediate 29: 4-(3-tert-Butyl-5-vinyl-benzyl)-3-oxo-3,4-dihydro-2H-1,4-benzoxazine-6-carbaldehyde. To a toluene solution of intermediate 27 (0.500 g, 1.11 mmol) was added vinyl tributyl tin (0.387 g, 1.22 mmol) followed by bis-triphenylphoshine palladium dichloride (0.031 g, 0.04 mmol). The reaction was heated to reflux for 5 hours. This material was chromatographed using 25% ethyl acetate/hexane to yield the title compound as a solid. MS: $M^+-1=349.2$ Da.

Example 56

4-(3-tert-Butyl-5-vinyl-benzyl)-6-(4-oxo-2-thioxo-thiazolidin-5-ylidenemethyl)-4H-1,4-benzoxazin-3-one The title compound was synthesized in a manner analogous to Example 1 using intermediate 29. Microanalysis ($C_{25}H_{24}N_2O_3S_2$): calculated: C=64.63, H=5.21, N=6.03; found: C=64.41, H=5.07, N=5.64. MS: $M^+-1=464.1$ Da.

Example 57

3-tert-Butyl-5-[3-oxo-6-(4-oxo-2-thioxo-thiazolidin-5-ylidenemethyl)-2,3-dihydro-1,4-benzoxazin-4-ylmethyl]-benzoic acid methyl ester The title compound was synthesized in a manner analogous to Example 38. Microanalysis ($C_{25}H_{24}N_2O_5S_2$): calculated: C=60.47, H=4.87, N=5.64; found: C=60.29, H=4.97, N=5.60. MS: $M^+-1=496.1$ Da.

Intermediate 30: 3-tert-Butyl-5-(6-formyl-3-oxo-2,3-dihydro-1,4-benzoxazin-4-ylmethyl)-benzoic acid methyl ester. The title compound was synthesized in a manner analogous to intermediate 22 using intermediate 3 and 3-bromomethyl-5-tert-butyl-benzoic acid methyl ester. MS: $M^+-1=381.3$ Da.

Intermediate 31: 3-tert-Butyl-5-(6-formyl-3-oxo-2,3-dihydro-1,4-benzoxazin-4-ylmethyl)-benzoic acid. The title compound was synthesized in a manner analogous to intermediate 23 using intermediate 30. MS: $M^+-1=367.2$ Da.

Example 58

3-tert-Butyl-5-[3-oxo-6-(4-oxo-2-thioxo-thiazolidin-5-ylidenemethyl)-2,3-dihydro-1,4-benzoxazin-4-ylmethyl]-benzoic acid The title compound was synthesized in a manner analogous to Example 1 using intermediate 31. $^1$H NMR (DMSO-$d_6$) δ 1.25 (s, 9H), 4.85 (s, 2H), 5.21 (s, 2H), 7.08–7.20 (m, 4H), 7.53 (s, 1H), 7.70 (s, 1H), 7.79 (s, 1H). MS: $M^+-1=482.1$ Da.

Intermediate 32: [3-tert-Butyl-5-(6-formyl-3-oxo-2,3-dihydro-1,4-benzoxazin-4-ylmethyl)-benzoylamino]-acetic acid tert-butyl ester. To a 0° C. tetrahydrofuran (50 mL) solution of intermediate 31 (0.172 g, 0.47 mmol) was added L-alanine tert-butyl ester hydrochloride (0.078 g, 0.47 mmol), 4-methylmorpholine (0.11 mL, 1.17 mmol), 1-hydroxybenzotriazole (0.094 g, 0.702 mmol), and 1-[3-dimethylamino)propyl]-3-ethylcarbodiimide hydrochloride (0.13 g, 0.70 mmol). The reaction was allowed to warm slowly to room temperature and then stirred overnight. The reaction was then diluted with ethyl acetate (150 mL). The organic layer was washed in succession with 5% citric acid (2×50 mL), saturated sodium bicarbonate (2×50 mL), and brine (1×50 mL). The organic layer was dried over $MgSO_4$, filtered and then concentrated under reduced pressure to yield the title compound. MS: $M^+-1=480.2$ Da.

Example 59

{3-tert-Butyl-5-[3-oxo-6-(4-oxo-2-thioxo-thiazolidin-5-ylidenemethyl)-2,3-dihydro-1,4-benzoxazin-4-ylmethyl]-benzoylamino}-acetic acid tert-butyl ester The title compound was synthesized in a manner analogous to Example 1 using intermediate 32. $^1$H NMR (DMSO-$d_6$) δ 1.28 (s, 9H), 1.35 (s, 9H), 3.80 (d, 2H), 4.90 (s, 2H), 5.22 (s, 2H), 7.13–7.23 (m, 3H), 7.39 (s, 1H), 7.49 (s, 1H), 7.64 (s, 1H), 7.75 (s, 1H), 7.80 (t, 1H). MS: $M^+-1=595.2$ Da.

Example 60

{3-tert-Butyl-5-[3-oxo-6-(4-oxo-2-thioxo-thiazolidin-5-ylidenemethyl)-2,3-dihydro-1,4-benzoxazin-4-ylmethyl]-benzoylamino}-acetic acid The title compound was synthesized in a manner analogous to intermediate 6 using Example 59. $^1$H NMR (DMSO-$d_6$) δ 1.27 (s, 18H), 3.82 (d, 2H), 4.91 (s, 2H), 5.22 (s, 2H), 7.13–7.23 (m, 3H), 7.41 (s, 1H), 7.49 (s, 1H), 7.64 (s, 1H), 7.76 (s, 1H), 8.79 (t, 1H), 13.70 (bs, 1H). MS: $M^+-1=539.1$ Da.

Example 61

4-(3,5-Di-tert-butyl-benzyl)-8-methyl-6-(4-oxo-2-thioxo-thiazolidin-5-ylidenemethyl)-4H-1,4-benzoxazin-3-one. The title compound was synthesized in a manner analogous to Example 35 using BEMP resin as in intermediate 22. Microanalysis ($C_{28}H_{32}N_2O_3S_2$): calculated: C=66.11, H=6.34, N=5.51; found: C=66.13, H=6.32, N=5.21. MS: $M^+-1=507.3$ Da.

Example 62

4-[1-(3,5-Di-tert-butyl-phenyl)-ethyl]-6-(4-oxo-2-thioxo-thiazolidin-5-ylidenemethyl)-4H-1,4-benzoxazin-3-one The title compound was synthesized in a manner analogous to Example 38. Microanalysis ($C_{28}H_{32}N_2O_3S_2$): calculated: C=66.11, H=6.34, N=5.51; found: C=65.69, H=6.25, N=5.39. MS: $M^+-1=508.3$ Da.

Intermediate 33: 4-(3-tert-Butyl-5-ethyl-benzyl)-6-hydroxymethyl-4H-benzo[1,4]oxazin-3-one. To a methanol solution (50 mL) solution of intermediate 29 (0.16 g, 0.45 mmol) was added platinum oxide (0.025 g). The solution was then pressurized with hydrogen for 36 hours. The reaction was then filtered through a pad of celite and washed with methanol. The methanol solution was concentrated under reduced pressure to yield the title compound. MS: $M^+-1=351.2$ Da.

Intermediate 34: 4-(3-tert-Butyl-5-ethyl-benzyl)-3-oxo-3,4-dihydro-2H-benzo[1,4]oxazine-6-carbaldehyde. Intermediate 33 was oxidized to the title compound using TPAP in a manner analogous to that described for intermediate 24. MS: $M^+-1=351.3$ Da.

Example 63

4-(3-tert-Butyl-5-ethyl-benzyl)-6-(4-oxo-2-thioxo-thiazolidin-5-ylidenemethyl)-4H-1,4-benzoxazin-3-one The title compound was synthesized in a manner analogous to Example 1 using intermediate 34. $^1$H NMR (DMSO-$d_6$) δ 1.06 (t, 3H), 1.17 (s, 9H), 2.48 (q, 2H), 4.87 (s, 2H), 5.10 (s, 2H), 6.85 (s, 1H), 7.05–7.21 (m, 5H), 7.45 (s, 1H). MS: $M^+-1=465.2$ Da.

Example 64

4-(3-Acetyl-5-tert-butyl-benzyl)-6-(4-oxo-2-thioxo-thiazolidin-5-ylidenemethyl)-4H-1,4-benzoxazin-3-one The title compound was synthesized in a manner analogous to Example 56. $^1$H NMR (DMSO-$d_6$) δ 1.26 (s, 9H), 2.53 (s, 3H), 4.94 (s, 2H), 5.26 (s, 2H), 7.15–7.26 (m, 3H), 7.51 (s, 1H), 7.63 (d, 2H), 7.81 (s, 1H). MS: $M^+-1=480.2$ Da.

Example 65

4-(5-tert-Butyl-biphenyl-3-ylmethyl)-6-(4-oxo-2-thioxo-thiazolidin-5-ylidenemethyl)-4H-1,4-benzoxazin-3-one The title compound was synthesized in a manner analogous to Example 56. $^1$H NMR (DMSO-$d_6$) δ 1.29 (s, 9H), 4.94 (s, 2H), 5.24 (s, 2H), 7.14–7.56 (m, 12H). MS: $M^+-1=514.2$ Da.

Example 66

5-[4-(2,6-Di-tert-butyl-pyridin-4-ylmethyl)-3-oxo-3,4-dihydro-2H-1,4-benzoxazin-6-ylmethylene]-thiazolidine-2,4-dione The title compound was synthesized in a manner analogous to Example 38 using thiazoladinedione instead of rhodanine. $^1$H NMR (DMSO-$d_6$) δ 1.23 (s, 18H), 4.92 (s, 2H), 5.16 (s, 2H), 7.06 (s, 3H), 7.15–7.27 (m, 2H), 7.65 (s, 1H). MS: $M^+-1=478.3$ Da.

Example 67

8-Chloro-4-(3,5-dimethyl-benzyl)-6-(4-oxo-2-thioxo-thiazolidin-5-ylidenemethyl)-4H-1,4-benzoxazin-3-one The title compound was synthesized in a manner analogous to Example 47. $^1$H NMR (DMSO-$d_6$) δ 2.22 (s, 6H), 5.04 (s, 2H), 5.08 (s, 2H), 6.87 (s, 2H), 6.90 (s, 2H), 7.42 (s, 1H), 7.47 (s, 1H). MS: $M^+-1=443.2$ Da.

Example 68

5-[8-Chloro-4-(3,5-dimethyl-benzyl)-3-oxo-3,4-dihydro-2H-1,4-benzoxazin-6-ylmethylene]-thiazolidine-2,4-dione The title compound was synthesized in a manner analogous to Example 47 using thiazoladinedione instead of rhodanine. $^1$H NMR (DMSO-$d_6$) δ 2.20 (s, 6H), 5.03 s, 2H), 5.07 (s, 2H), 6.89 (t, 3H), 7.44 (s, 1H), 7.58 (s, 1H). MS: $M^+-1=427.2$ Da.

Example 69

4-(3,5-Dimethyl-benzyl)-8-fluoro-6-(4-oxo-2-thioxo-thiazolidin-5-ylidenemethyl)-4H-1,4-benzoxazin-3-one The title compound was synthesized in a manner analogous to Example 46. Microanalysis ($C_{21}H_{17}F_1N_2O_3S_2$): calculated: C=58.86, H=4.00, N=6.54; found: C=58.98, H=3.97, N=6.51. MS: $M^+-1=427.2$ Da.

Intermediate 35: 4-(3-Bromomethyl-5-tert-butyl-benzyl)-3-oxo-3,4-dihydro-2H[1,4]oxazine-6-carbaldehyde. The title compound was synthesized in a manner analogous to intermediate 16 using intermediate 3 and 1,3-bis-bromomethyl-5-tert-benzene. MS: $M^++1=416.2$ Da.

Intermediate 36: Acetic acid 3-tert-butyl-5-(6-formyl-3-oxo-2,3-dihydro-benzo[1,4]oxazin-4-ylmethyl)-benzyl ester. To an acetic acid (10 mL) solution of intermediate 35 (0.567 g, 1.36 mmol) was added silver acetate (0.375 g). The reaction was heated to reflux for 1.5 hours. The reaction was cooled to room temperature, and the precipitate was filtered off and washed with ethyl acetate (15 mL). The filtrate was concentrated under reduced pressure to yield a crude oil. This material was chromatographed using 25% ethyl acetate/hexane to yield the title product. MS: $M^+-1=395.3$ Da.

Example 70

Acetic acid 3-tert-butyl-5-[3-oxo-6-(4-oxo-2-thioxo-thiazolidin-5-ylidenemethyl)-2,3-dihydro-1,4-benzoxazin-4-ylmethyl]-benzyl ester The title compound was synthesized in a manner analogous to Example 66 using intermediate 36. $^1$H NMR (DMSO-$d_6$) δ 1.23 (s, 9H), 1.98 (s, 3H), 4.91 (s, 2H), 4.99 (s, 2H), 5.18 (s, 2H), 7.04 (s, 1H), 7.15–7.25 (m, 4H), 7.36 (s, 1H), 7.50 (s, 1H). MS: $M^+-1=509.3$ Da.

Example 71

8-Fluoro-4-(4-morpholin-4-ylmethyl-benzyl)-6-(4-oxo-2-thioxo-thiazolidin-5-ylidenemethyl)-4H-1,4-benzoxazin-3-one The title compound was synthesized in a manner analogous to Example 19 using intermediate 24, 1,4-dibromomethylbenzene, and morpholine. $^1$H NMR (DMSO-$d_6$) δ 2.61 (bs, 4H), 3.59 (bs, 4H), 3.75 (bs, 2H), 4.99 (s, 2H), 5.19 (s, 2H), 6.85 (s, 1H), 7.22 (d, 1H), 7.26 (s, 1H), 7.34 (s, 4H). MS: $M^++1=500.1$ Da.

Example 72

4-(4-Diethylaminomethyl-benzyl)-8-fluoro-6-(4-oxo-2-thioxo-thiazolidin-5-ylidenemethyl)-4H-1,4-benzoxazin-3-one The title compound was synthesized in a manner analogous to Example 71. 1H N (DMSO-$d_6$) δ 1.13–1.16 (m, 6H), 2.85–3.06 (m, 4H), 4.10–4.28 (bs, 2H), 4.97 (s, 2H), 5.21 (s, 2H), 6.80 (s, 1H), 6.99 (s, 1H), 7.13 (dd, 1H), 7.40 (d, 1H), 7.46 (d, 1H). MS: $M^++1=86.2$ Da.

Example 73

8-Fluoro-6-(4-oxo-2-thioxo-thiazolidin-5-ylidenemethyl)-4-(4-piperidin-1-ylmethyl-benzyl)-4H-1,4-benzoxazin-3-one The title compound was synthesized in a manner analogous to Example 71. $^1$H NMR (DMSO-$d_6$) δ 1.25–1.80 (m, 6H), 2.75–3.05 (m, 4H), 4.14 (bs, 2H), 4.96 (s, 2H), 5.21 (s, 2H), 6.80 (s, 1H), 7.00 (s, 1H), 7.14 (d, 1H), 7.39–7.45 (m, 4H). MS: $M^++1=498.1$ Da.

Example 74

4-{4-[3-Oxo-6-(4-oxo-2-thioxo-thiazolidin-5-ylidenemethyl)-2,3-dihydro-1,4-benzoxazin-4-ylmethyl]-benzyl}-piperazine-1-carboxylic acid tert-butyl ester The title compound was synthesized in a manner analogous to Example 19. $^1$H NMR (DMSO-$d_6$) δ 1.36 (s, 9H), 2.45 (bs, 4H), 3.31 (bs, 4H), 3.63 (s, 2H), 4.91 (s, 2H), 5.17 (s, 2H), 7.07 (d, 1H), 7.14 (d, 1H), 7.31 (dd, 1H), 7.31 (s, 4H), 7.39 (s, 1H). MS: $M^++1=581.2$ Da.

Example 75

4-{4-[6-(2,4-dioxo-thiazolidin-5-ylidenemethyl)-3-oxo-2,3-dihydro-1,4-benzoxazin-4-ylmethyl]-benzyl}-piperazine-1-carboxylic acid tert-butyl ester The title compound was synthesized in a manner analogous to Example 19 using thiazoladinedione instead of rhodanine. $^1$H NMR (DMSO-$d_6$) δ 1.35 (s, 9H), 2.28–2.30 (m, 4H), 3.26–3.30 (m, 4H), 3.46 (s, 2H), 4.90 (s, 2H), 5.16 (s, 2H), 7.11–7.15 (m, 2H), 7.22–7.27 (m, 5H), 7.61 (s, 1H). MS: M$^+$+1=565.2 Da.

Example 76

5-[8-Fluoro-3-oxo-4-(4-piperidin-1-ylmethyl-benzyl)-3,4-dihydro-2H-1,4-benzoxazin-6-ylmethylene]-thiazolidine-2,4-dione The title compound was synthesized in a manner analogous to Example 71, using diethylamine and 1,4-dibromomethylbenzene, and substituting thiazoladinedione for rhodanine. $^1$H NMR (DMSO-$d_6$) δ 1.42 (bs, 2H), 1.58 (bs, 4H), 2.78 (bs, 4H), 3.94 (bs, 2H), 4.97 (s, 2H), 5.19 (s, 2H), 6.90 (s, 1H), 7.17 (d, 1H), 7.30 (s, 1H), 7.34–7.40 (m, 4H). MS: M$^+$+1=482.1 Da.

Example 77

4-[4-(4-Butyl-piperazin-1-ylmethyl)-benzyl]-6-(4-oxo-2-thioxo-thiazolidin-5-ylidenemethyl)-4H-1,4-benzoxazin-3-one The title compound was synthesized in a manner analogous to Example 19. $^1$H NMR (DMF-$d_7$) δ 0.87 (t, 3H), 1.26–1.35 (m, 2H), 1.53–1.61 (m, 2H), 2.60–2.95 (m 4H), 3.58 (s, 2H), 4.94 (s, 2H), 5.29 (s, 2H), 7.12–7.22 (m, 4H), 7.32 (d, 2H), 7.39 (d, 2H). MS: M$^+$+1=537.2 Da.

Intermediate 37: 4-(4-Bromomethyl-benzyl)-8-chloro-3-oxo-3,4-dihydro-2H-1,4-benzoxazine-6-carbaldehyde. The title compound was synthesized in a manner analogous to intermediate 16 using intermediate 26 and 1,4-dibromomethylbenzene.

Intermediate 38: 8-Chloro-4-(4-dimethylaminomethyl-benzyl)-3-oxo-3,4-dihydro-2H-benzo[1,4]oxazine-6-carbaldehyde. The title compound was synthesized in a manner analogous to intermediate 17 using intermediate 37 and dimethylamine.

Example 78

8-Chloro-4-(4-diethylaminomethyl-benzyl)-6-(4-oxo-2-thioxo-thiazolidin-5-ylidenemethyl)-4H-1,4-benzoxazin-3-one The title compound was synthesized in a manner analogous to Example 1 using intermediate 38. $^1$H NMR (DMSO-$d_6$) δ 1.15 (t, 6H), 2.98 (bs, 4H), 4.19 (bs, 2H), 5.01 (s, 2H), 5.21 (s, 2H), 6.92 (s, 1H), 6.98 (s, 1H), 7.28 (s, 1H), 7.40 (d, 2H), 7.46 (d, 2H). MS: M$^+$+1=502.1 Da.

Example 79

8-Chloro-6-(4-oxo-2-thioxo-thiazolidin-5-ylidenemethyl)-4-(4-piperidin-1-ylmethyl-benzyl)-4H-1,4-benzoxazin-3-one; compound with Toluene-4-sulfonic acid The title compound was synthesized in a manner analogous to Example 78 using piperidine instead of dimethylamine. To a suspension of crude product in benzene was added p-toluenesulfonic acid monohydrate (0.190 g, 1.05 equiv) and mixture heated to reflux for 18 hours. The reaction was concentrated to a yellow residue that was dissolved in CH$_2$Cl$_2$ with heat. Upon cooling a yellow precipitate resulted which was filtered and dried. $^1$H NMR (DMSO-$d_6$) δ 1.25–1.40 (m, 1H), 1.50–1.70 (m, 3H), 1.75–1.80 (m, 2H), 2.27 (s, 3H), 2.78–2.90 (m, 2H), 3.25–3.35 (m, 2H), 4.26 (bs, 2H), 5.08 (s, 2H), 5.24 (bs, 2H), 6.89 (s, 1H), 7.09 (d, 2H), 7.40–7.52 (m, 4H), 9.14 (bs, 1H). MS: M$^+$+1=514.1 Da.

Example 80

8-Chloro-4-(4-morpholin-4-ylmethyl-benzyl)-6-(4-oxo-2-thioxo-thiazolidin-5-ylidenemethyl)-4H-1,4-benzoxazin-3-one The title compound was synthesized in a manner analogous to Example 78 using morpholine instead of dimethylamine. $^1$H NMR (DMSO-$d_6$) δ 2.64 (bs, 4H), 3.30 (bs, 4H), 3.78 (bs, 2H), 5.03 (s, 2H), 5.19 (s, 2H), 6.94 (s, 1H), 7.27–7.38 (m, 7H). MS:M$^+$+1=516.0 Da.

Intermediate 39: 4-Formyl-2-nitrophenylsulfanyl acetic acid. In acetonitrile (150 mL) was stirred 4-chloro-3-nitrobenzaldehyde (7.42 g, 40 mmol), thioglycolic acid (4.6 g, 50 mmol), and triethylamine (1.01 g, 100 mmol). The mixture stirred at room temperature overnight. The mixture was evaporated free of solvent and the residue partitioned between water (200 mL) and ethyl acetate (200 mL). The organic phase was discarded and the aqueous phase made acidic with concentrated HCl. The mixture was allowed to stand overnight to precipitate. The solid was collected by filtration, washed with water (2×200 mL) and then dried in vacuo at 65° C. for 3 hours. MS: M$^+$−1=240.

Intermediate 40: 3-oxo-3,4-dihydro-2H-benzo[1,4]thiazine-6-carboxaldehyde. In ammonium hydroxide (20 mL) was suspended the intermediate 39 (1.91 g, 7.91 mmol). To this was added dropwise a solution of iron (II) sulfate heptahydrate (22 g) in water (48 mL). The mixture warmed to 90° C. for 1 hour and then filtered through celite to remove the iron salts. The filtrate was treated with 6N HCl and allowed to precipitate. The solid was collected by filtration and warmed to reflux in ethanol (100 mL). The solution was allowed to cool and then filtered to collect the solid. MS:M$^+$+1=194.1.

Intermediate 41: 4-Benzyl-3-oxo-3,4-dihydro-2H-benzo[1,4]thiazine-6-carboxaldehyde. The title compound was synthesized in a manner analogous to Example 19 using intermediate 40. MS:M$^+$+1=84.1.

Example 81

4-Benzyl-6-(4-oxo-2-thioxo-thiazolidin-5-ylidenemethyl)-4H-1,4-benzothiazin-3-one The title compound was synthesized in a manner analogous to Example 1 using intermediate 41. MS:M$^+$+1=399.1.

Example 82

4-(3,5-Di-tert-butyl-benzyl)-6-(4-oxo-2-thioxo-thiazolidin-5-ylidenemethyl)-4H-1,4-benzothiazin-3-one The title compound was synthesized in a manner analogous to Example 81. MS:M$^+$+1=511.1. Microanalysis (C$_{27}$H$_{30}$N$_2$O$_2$S$_3$ 0.7 Et$_2$O): calculated: C=63.61, H=6.63, N=4.98; found: C=63.65, H=6.93, N=4.61.

Example 83

6-(4-Oxo-2-thioxo-thiazolidin-5-ylidenemethyl)-4H-1,4-benzothiazin-3-one

The title compound was synthesized in a manner analogous to Example 81. MS:M$^+$+1=309.0. Microanalysis (C$_{12}$H$_8$N$_2$O$_2$S$_3$.0.2H$_2$O): calculated: C=46.19, H=2.72, N=8.98, S=30.83; found: C=46.47, H=2.79, N=8.58, S=30.08.

Example 84

6-(4-Oxo-2-thioxo-oxazolidin-5-ylidenemethyl)-4H-benzo[1,4]oxazin-3-one

To 20 mL of anhydrous tetrahydrofuran at −78° C. was added dropwise 5.6 mL of TiCl$_4$ (1.0 M in dichloromethane, 5.6 mM). A mixture of intermediate 3 (0.5 g, 2.8 mmol) and 2-thiooxazolid-4-one (0.5 g, 4.9 mmol) was added all at once, and the resulting mixture was stirred. The reaction was allowed to warm to 0° C. and anhydrous pyridine (0.9 mL, 11.1 mmol) was added to the stirring mixture dropwise. Upon addition of the pyridine, the mixture was warmed to room temperature, then heated to 50° C. and stirred overnight. The reaction was diluted with water, resulting in a precipitate. The precipitate was collected by filtration and triturated with hot methanol. MS (APCI$^-$): M$^+$−1=275.0. Microanalysis (C$_{12}$H$_8$N$_2$O$_4$S): found: C=52.07; H=2.92; N=9.84; theory, C=52.17; H=3.02; N=10.14.

Example 85

5-[4-(3,5-Di-tert-butyl-benzyl)-3-oxo-3,4-dihydro-2H-1,4-benzoxazin-6-ylmethylene]-thiazolidine-2,4-dione The title compound was synthesized in a manner analogous to Example 2, using cesium carbonate as in intermediate 16, and using thiazolidine dione in place of rhodanine. MS (APCI$^+$):M$^+$+1=479.1. Microanalysis (C$_{27}$H$_{30}$N$_2$O$_4$S): calculated: C=67.76; H=6.32; N=5.85; found: C=67.53; H=6.38; N=5.83.

Example 86

3-(3-Oxo-3,4-dihydro-2H-benzo[1,4]oxazin-6-ylmethylene)-pyrrolidine-2,5-dione. Maleimide (1.0 g, 10.3 mmol) and triphenylphosphine (0.96 g, 9.9 mmol) were stirred in 20 mL of glacial acetic acid The mixture was heated to 100° C. and stirred at this temperature for 0.5 hour. The acetic acid was removed in vacuo and the resulting pink oil was triturated with ether to obtain a solid. The ether was decanted, and the solid was triturated with acetone to give a white solid. The white solid was collected by filtration and dried under vacuum. To a solution of intermediate 3 (0.5 g, 2.8 mmol) in anhydrous methyl sulfoxide was added the solid phosphine from above (0.5 g, 1.4 mmol); the resulting solution was stirred overnight. Another equivalent of phosphine intermediate was added, and the mixture was stirred another 24 hours. The mixture was diluted with water and the resulting brown solid was collected by filtration. The solid was rinsed with water and ether, then dried under vacuum. MS (APCI$^-$): M$^+$−1=257.1. Microanalysis (C$_{13}$H$_{10}$N$_2$O$_4$.0.72H$_2$O): calculated: C=57.58; H=4.06; N=10.14; found: C=57.57; H=4.25; N=10.33.

Example 87

5-(3-Oxo-3,4-dihydro-2H-benzo[1,4]oxazin-6-ylmethylene)-imidazolidine-2,4-dione

The title compound was synthesized in a manner analogous to Example 84, except that hydantoin was substituted for 2-thiooxazolid-4-one. MS (APCI$^-$): M$^+$−1=258.0. Microanalysis (C$_{12}$H$_9$N$_3$O$_4$.0.85H$_2$O): found: C=52.50; H=3.79; N=15.10; calculated, C=52.50; H=3.93; N=15.31.

Intermediate 42: (4-Formyl-2-nitro-phenoxy)acetic acid ethyl ester. To a solution of 4-hydroxy-3-nitrobenzaldehyde (5.00 g, 29.9 mmol) in tetrahydrofuran/DMF (300 mL/120 mL) was added NaH (60%, 1.32 g, 32.9 mmol), followed by ethyl bromoacetate (5.49 g, 3.65 mL, 32.9 mmol). The mixture was heated at reflux for 20 hours, cooled to room temperature, and concentrated under reduced pressure. The residue was dissolved in ethyl acetate (200 mL), acidified to pH 2 with 1N HCl, and the layers were separated. The aqueous layer was extracted with ethyl acetate (2×50 mL), the organic extracts were combined and washed with saturated NaHCO$_3$ (2×50 mL), brine (1×50 mL), dried over MgSO$_4$, and concentrated to an amber oil. Purification of the residue by silica gel flash chromatography (25% ethyl acetate/hexanes) afforded the title compound. $^1$H NMR (DMSO-d$_6$) δ 1.91 (t, J=7.08 Hz, 3H), 4.16 (q, J=7.08 Hz, 2H), 5.15 (s, 2H), 7.50 (d, J=8.79 Hz, 1H), 8.12–8.14 (m, 1H), 8.42 (d, J=1.95 Hz, 1H), 9.93 (s, 1H) ppm. MS: M$^+$−1=252.1 Da.

Intermediate 43: 4-Hydroxy-6-hydroxymethyl-4H-benzo[1,4]oxazin-3-one. To a solution of NaBH$_4$ (1.00 g, 26.4 mmol) in H$_2$O (10 mL) was carefully added a suspension of Pd/C (10%, 0.200 g, 0.187 mmol) in H$_2$O (10 mL). The suspension was diluted with 20 mL of dioxane and saturated with N$_2$ gas for 5 minutes. A solution of intermediate 42 (1.00 g, 3.74 mmol) in dioxane (20 mL) was added dropwise over 15 minutes, while N$_2$ was bubbled through the mixture. After the addition was complete, the reaction was continued for 25 minutes with N$_2$ bubbling through. The mixture was then filtered through a pad of celite, the filtrate was acidified with 10% HCl, diluted with 100 mL of H$_2$O, and the organic solvent was removed under reduced pressure, resulting a solid precipitate. The pure solid was isolated by filtration. $^1$H NMR (DMSO-d$_6$) δ 4.43 (dd, J=5.62, 2.44 Hz, 2H), 4.71 (d, J=2.93 Hz, 2H), 5.16–5.20 (m, 1H), 6.90 (s, 2H), 7.20 (s, 1H)ppm. MS: M$^+$−1=194.2Da.

Intermediate 44: 4-(3,4-Dichloro-benzyloxy)-6-hydroxymethyl-4H-benzo[1,4]oxazin-3-one. To a mixture of intermediate 43 (0.200 g, 1.03 mmol) in 10 mL of acetone were added K$_2$CO$_3$ (0.283 g, 2.05 mmol), and 3,4-dichlorobenzylbromide (0.270 g, 1.13 mmol). The mixture was

Microanalysis (C$_{19}$H$_{14}$N$_2$O$_2$S$_3$.0.05H$_2$O): calculated: C=57.13, H=3.56, N=7.02, S=24.08, KF(H$_2$O)=0.23; found: C=56.97, H=3.62, N=6.98, S=23.87, KF(H$_2$O)=0.25.

heated at reflux for 2 hours, cooled to room temperature, and H$_2$O (5 mL) and 1N HCl (5 mL were added. The organic solvents were removed under reduced pressure, and the residue was stirred with ethyl acetate (20 mL) and 1N HCl (10 mL). A white precipitate was isolated by filtration and dried in vacuo to provide the title compound. $^1$H NMR (DMSO-d$_6$) δ 4.44 (d, J=5.13 Hz, 2H), 4.74 (s, 2H), 5.09 (s, 2H), 5.19–5.21 (m, 1H), 6.95 (s, 2H), 7.14 (s, 1H), 7.53 (d, J=8.30 Hz, 1H), 7.67 (d, J=8.06 Hz, 1H), 7.83 (s, 1H) ppm. MS: M$^+$+1=336.0 Da.

Intermediate 45: 4-(3,4-Dichloro-benzyloxy)-3-oxo-3,4-dihydro-2H-benzo[1,4]oxazine-6-carbaldehyde. Intermediate 44 was reduced to the title compound using TPAP in a manner analogous to that described for intermediate 24. $^1$H NMR (DMSO-d$_6$) δ 4.93 (s, 2H), 5.15 (s, 2H), 7.19 (d, J=8.79 Hz, 1H), 7.54–7.56 (m, 1H), 7.60–7.62 (m, 2H), 7.67 (d, J=8.06 Hz, 1H), 7.85 (d, J=1.47 Hz, 1H), 9.90 (s, 1H) ppm. MS: M$^+$+1=352.0 Da.

Example 88

4-(3,4-Dichloro-benzyloxy)-6-(4-oxo-2-thioxo-thiazolidin-5-ylidenemethyl)-4H-benzo[1,4]oxazin-3-one The title compound was 15' synthesized in a manner analogous to Example 1 from intermediate 45. MP>300° C. MS: M$^+$−1=465.0 Da.

Example 89

4-(3,5-Dimethyl-benzyloxy)-6-(4-oxo-2-thioxo-thiazolidin-5-ylidenemethyl)-4H-benzo[1,4]oxazin-3-one The title compound was synthesized in a manner analogous to Example 88. MP>300° C. MS: M$^+$+1=427.1 Da.

Intermediate 46: (4-Bromo-2-nitro-phenoxy)-acetic acid ethyl ester. The title compound was prepared in a manner analogous to intermediate 42 from 4-bromo-2-nitrophenol. $^1$H NMR (DMSO-d$_6$) δ 1.18 (t, J=7.08 Hz, 3H), 4.14 (q, J=7.08 Hz, 2H), 5.02 (s, 2H), 7.27 (d, J=9.03 Hz, 1H), 7.78–7.81 (m, 1H), 8.12 (d, J=2.44 Hz, 1H) ppm. MS: M+-C$_2$H$_5$=288.0 Da.

Intermediate 47: 6-Bromo-4-hydroxy-4H-benzo[1,4]oxazin-3-one. The title compound was prepared in a manner analogous to intermediate 43 from intermediate 46. MP=201–204° C. MS: M$^+$−1=243.9 Da.

Intermediate 48: 4-Benzyloxy-6-bromo-4H-benzo[1,4]oxazin-3-one. The title compound was prepared in a manner analogous to intermediate 43 from intermediate 47 (0.500 g, 2.05 mmol) and purified by silica gel flash column chromatography (10% ethyl acetate/hexanes). $^1$H NMR (DMSO-d$_6$) δ 4.81 (s, 2H), 5.10 (s, 2H), 6.95 (d, J=3.91 Hz, 1H), 7.14 (d, J=2.44 Hz, 1H), 7.17 (s, 1H), 7.38–7.42 (m, 3H), 7.51 (d, J=1.95 Hz, 1H), 7.53 (d, J=2.93 Hz, 1H) ppm. MS: M$^+$−1=334.0 Da.

Intermediate 49: 4-Benzyloxy-3-oxo-3,4-dihydro-2H-benzo[1,4]oxazine-6-carbaldehyde. To a 3-neck 50 mL round bottom flask equipped with a reflux condenser and glass gas inlet tube was added PdCl$_2$(PPh$_3$)$_2$ (10.5 mg, 0.150 mmol), intermediate 48 (0.250 g, 0.748 mmol), and sodium formate (0.101 g, 1.50 mmol). The atmosphere was replaced with carbon monoxide, 2 mL of DMF was added via syringe, and a slow stream of carbon monoxide was bubbled into the vigorously stirred suspension as it was heated to 1 10° C. for 3.5 hours. The reaction was cooled to room temperature, diluted with ethyl acetate (20 mL), and saturated NaHCO$_3$ (20 mL). The mixture was filtered through a pad of celite. The layers of the filtrate were separated, and the aqueous layer was extracted with ethyl acetate (3×20 mL). The combined organic extracts were washed with water (2×10 mL), brine (1×10 mL), dried over MgSO$_4$, filtered and concentrated. $^1$H NMR (DMSO-d$_6$) δ 4.94 (s, 2H), 5.13 (s, 2H), 7.19 (d, J=8.79 Hz, 1H), 7.40–7.42 (m, 3H), 7.54–7.55 (m, 2H), 7.59–7.61 (m, 2H), 9.89 (s, 1H) ppm. MS: M$^+$−1=282.1 Da.

Example 90

4-Benzyloxy-6-(4-oxo-2-thioxo-thiazolidin-5-ylidenemethyl)-4H-benzo[1,4]oxazin-3-one The title compound was synthesized in a manner analogous to Example 1 using intermediate 49. MP>300° C. MS: M$^+$−1=397.1 Da.

Example 91

8-Methyl-6-(4-oxo-2-thioxo-thiazolidin-5-ylidenemethyl)-4-(4-piperidin-1-ylmethyl-benzyl)-4H-benzo[1,4]oxazin-3-one The title compound was prepared in a manner analogous to Example 71 using 1,4-dibromomethyl benzene and piperidine. MP=277–278° C. MS: M$^+$−1=493.2 Da.

Example 92

4-(4-Diethylaminomethyl-benzyl)-8-methyl-6-(4-oxo-2-thioxo-thiazolidin-5-ylidenemethyl)-4H-benzo[1,4]oxazin-3-one The title compound was prepared in a manner analogous to Example 71 using 1,4-dibromomethyl benzene and diethylamine. MP=250–252° C. MS: M$^+$−1=481.2 Da.

Example 93

5-[4-(4-Diethylaminomethyl-benzyl)-3-oxo-3,4-dihydro-2H-benzo[1,4]oxazin-6-ylmethylene]-thiazolidine-2,4-dione The title compound was synthesized in a manner analogous to Example 19, using thiazoladinedione instead of rhodanine. MP=244–246° C. MS: M$^+$+1=452.3 Da.

Example 94

4-(3,5-Diisopropoxy-benzyl)-6-(4-oxo-2-thioxo-thiazolidin-5-ylidenemethyl)-4H-benzo[1,4]oxazin-3-one MP=245–247° C. MS: M$^+$−1=498.1 Da.

Example 95

4-(5-tert-Butyl-2-methoxy-benzyl)-6-(4-oxo-2-thioxo-thiazolidin-5-ylidenemethyl)-4H-1,4-benzoxazin-3-one MP=255–257° C. MS: M$^+$−1=468.0 Da.

Example 96

6-(4-Oxo-2-thioxo-thiazolidin-5-ylidenemethyl)-4-(2,3,5,6-tetramethyl-benzyl)-4H-1,4-benzoxazin-3-one MP=277–280° C. MS: M$^+$−1=438.0 Da.

Example 97

4-(3,4-Dimethyl-benzyl)-6-(4-oxo-2-thioxo-thiazolidin-5-ylidenemethyl)-4H-1,4-benzoxazin-3-one MP>300° C. MS: M$^+$−1=410.0 Da.

Example 98

4-(2,3-Dimethyl-benzyl)-6-(4-oxo-2-thioxo-thiazolidin-5-ylidenemethyl)-4H-benzo[1,4]oxazin-3-one MP>300° C. MS: M$^+$−1=410.0 Da.

Example 99

4-(2,5-Dimethyl-benzyl)-6-(4-oxo-2-thioxo-thiazolidin-5-ylidenemethyl)-4H-1,4-benzoxazin-3-one MP>300° C. MS: M$^+$−1=410.0 Da.

Example 100

4-(2,4-Dimethyl-benzyl)-6-(4-oxo-2-thioxo-thiazolidin-5-ylidenemethyl)-4H-1,4-benzoxazin-3-one $^1$H NMR (DMSO-d$_6$) δ 2.22 (s, 3H), 2.35 (s, 3H), 4.94 (s, 2H), 5.05 (s, 2H), 6.79 (d, J=7.81 Hz, 1H), 6.87 (s, 2H), 7.06 (s, 1H), 7.16 (d, J=8.30 Hz, 1H), 7.25 (dd, J=8.55, 1.71 Hz, 1H), 7.47 (s, 1H), 13.69 (bs, 1H) ppm. MS: M$^+$−1=410.0 Da.

Example 101

6-(4-Oxo-2-thioxo-thiazolidin-5-ylidenmethyl)-4-[2-m-tolyl-ethyl]-4H-benzo[1,4]oxazin-3-one $^1$H NMR (DMSO-d$_6$) δ (s, 3H) 2.26–2.83 (t, 2H), 4.089 (t, 2H), 4.71 (s, 2H), 7.00–7.05 (d, 1H), 7.15–7.16 (d, 1H), 7.18–7.20 (m, 4H), 7.44 (s, 1H), 7.69 (s, 1H) ppm. MS: M$^+$+1=411 Da.

Example 102

4-[2-(4-Bromo-phenyl)-ethyl]-6-(4-oxo-2-thioxo-thiazolidin-5-ylidenmethyl)-4H-benzo[1,4]oxazin-3-one MS: M$^+$+1=475 Da. MP=274–276° C.

Example 103

4-[2-(3,4-Dichloro-phenyl)-ethyl]-6-(4-oxo-2-thioxo-thiazolidin-5-ylidenmethyl)-4H-benzo[1,4]oxazin-3-one MS: M$^+$+1=464 Da. MP=267–269° C.

Example 104

6-(Oxo-2-thioxo-thiazolidin-5-ylidenmethyl)-4-[2-(4-trifluoromethyl-phenyl)-ethyl]-4H-benzo[1,4]oxazin-3-one MS: M$^+$+1=465 Da. MP=253–255° C.

Example 105

4-[2-(2,4-Dichloro-phenyl)-ethyl]-6-(4-oxo-2-thioxo-thiazolidin-5-ylidenmethyl)-4H-benzo[1,4]oxazin-3-one MS: M$^+$+1=464 Da. MP=267–269° C.

Example 106

6-(Oxo-2-thioxo-thiazolidin-5-ylidenmethyl)-4-[2-(3-trifluoromethyl-phenyl)-ethyl]-4H-benzo[1,4]oxazin-3-one MS: M$^+$+1=465 Da. MP=241–243° C.

Example 107

8-Chloro-6-(oxo-2-thioxo-thiazolidin-5-ylidenmethyl)-4-[2-(4-trifluoromethyl-phenyl)-ethyl]-4H-benzo[1,4]oxazin-3-one The title compound was synthesized in a manner analogous to Example 47. MS: M$^+$+1=499 Da. MP=275–277° C.

Example 108

6-(Oxo-2-thioxo-thiazolidin-5-ylidenmethyl)-4-[2-(2-trifluoromethyl-phenyl)-ethyl]-4H-benzo[1,4]oxazin-3-one MS: M$^+$+1=465 Da. MP=283–286° C.

Example 109

(S)-4-[2-(3,4-Dichloro-phenyl)-ethyl]-2-methyl-6-(4-oxo-2-thioxo-thiazolidin-5-ylidenmethyl)-4H-benzo[1,4]oxazin-3-one The title compound was synthesized in a manner analogous to Example 18. $^1$H NMR (DMSO-d$_6$) δ 1.35–1.37 (d, 3H), 2.89 (t, 3H), 4.05–4.20 (m, 2H), 4.70–4.80 (m, 1H), 7.19–7.21 (m, 3H), 7.40–7.60 (m, 3H), 7.70 (s, 1H) ppm. MS: M$^+$+1=478 Da.

Example 110

8-Chloro-4-[2-(3,4-dichloro-phenyl)-ethyl]-6-(4-oxo-2-thioxo-thiazolidin-5-ylidenmethyl)-4H-benzo[1,4]oxazin-3-one The title compound was synthesized in a manner analogous to Example 47. $^1$H NMR (DMSO-d$_6$) δ 2.88 (t, 2H), 4.05–4.20 (t, 2H), 4.81 (s, 2H), 7.19–7.21 (d, 2H), 7.30 (s, 1H), 7.41 (s, 1H), 7.50–7.52 (d, 1H), 7.56 (s, 1H), 7.64 (s, 1H) ppm. MS: M$^+$+1=500 Da.

Example 111

4-[2-(3,4-dichloro-phenyl)-ethyl]-8-fluoro-6-(4-oxo-2-thioxo-thiazolidin-5-ylidenmethyl)-4H-benzo[1,4]oxazin-3-one The title compound was synthesized in a manner analogous to Example 46. $^1$H NMR (DMSO-d$_6$) δ 2.88 (t, 2H), 4.12–4.16 (m, 2H), 4.78 (s, 2H), 7.19–7.21 (m, 1H), 7.31 (s, 1H), 7.47–7.49 (d, 1H), 7.56 (s, 1H), 7.65 (s, 1H) ppm. MS: M$^+$+1=482 Da.

Example 112

4-[2-(3,4-dichloro-phenyl)-ethyl]-8-methyl-6-(4-oxo-2-thioxo-thiazolidin-5-ylidenmethyl)-4H-benzo[1,4]oxazin-3-one The title compound was synthesized in a manner analogous to Example 35. $^1$H NMR (DMSO-d$_6$) δ 2.21 (s, 3H), 2.87 (t, 2H), 4.12 (t, 2H), 4.79–4.81 (s, 2H), 7.06 (s, 1H), 7.19–7.21 (d, 1H), 7.38 (s, 1H), 7.48–7.58 (m, 1H), 7.64 (s, 1H) ppm. MS: M$^+$+1=478 Da.

Example 113

4-[2-(Bis-trifluromethyl-phenyl)-ethyl]-6-(4-oxo-2-thioxo-thiazolidin-5-ylidenmethyl)-4H-benzo[1,4]oxazin-3-one MS: M$^+$+1=531 Da. MP=261–263° C.

Intermediate 50: 3-Oxo-4-(3-pyridin-4-yl-benzyl)-3,4-dihydro-2H-benzo[1,4]oxazine-6-carbaldehyde. To a solution of 4-(3-iodo-benzyl)-3-oxo-3,4-dihydro-2H-benzo[1,4]oxazine-6-carbaldehyde (0.100 g, 0.254 mmol) and Pd(PPh$_3$)$_4$ (0.015 g, 0.01 mmol) in DMF (20.0 mL) was added pyridine-4-boronic acid (0.034 g, 0.279 mmol) followed by the addition of Na$_2$CO$_3$ (2 mL, 2.0 M solution). The solution was heated to reflux overnight with good stirring. The heat was turned off, the solution was poured into H$_2$O (30 mL), and the organic phase was extracted with CH$_2$Cl$_2$ (3×40 mL). The organic phase was than dried over MgSO$_4$, filtered, and concentrated down under reduced pressure. The product was chromatographed with CH$_2$Cl$_2$/MeOH (9:1).

Example 114

6-(4-Oxo-2-thioxo-thiazolidin-5-ylidenemethyl)-4-(3-pyridin-4-yl-benzyl)-4H-benzo[1,4]-oxazin-3-one The title compound was synthesized in a manner analogous to Example 1 from intermediate 50. MS: M$^+$+1=460 Da. MP=297–299° C.

Intermediate 51: 4-(3-Iodo-5-methyl-benzyl)-3-oxo-3,4-dihydro-2H-benzo[1,4]oxazine-6-carbaldehyde. The title compound was synthesized in a manner analogous to intermediate 4 using intermediate 3 and 1-bromomethyl-3-iodo-5-methyl-benzene. $^1$H NMR (DMSO-d$_6$) δ 2.20 (s, 3H), 4.95 (s, 2H), 5.15 (s, 2H), 7.10 (s, 1H),7.19–7.21, (d, 1H), 7.43–7.47 (m, 3H), 7.58–7.59 (d, 1H) ppm. MS: M$^+$+1=408 Da.

Intermediate 52: 4-(Furan-3-yl-5-methyl-benzyl)-3-oxo-3,4-dihydro-2H-benzo[1,4]-oxazine-6-carbaldehyde. To a solution of intermediate 51 (0.15 g, 0.368 mmol) and Pd(PPh$_3$)$_4$ (0.017 g, 0.014 mmol) was added furan-3-boronic acid (0.045 g, 0.405 mmol) followed by Na$_2$CO$_3$ (2.0 mL, 2.0 M solution). The solution was then heated to reflux overnight with good stirring. The heat was turned off, the solution was poured into H$_2$O (30 mL), and the aqueous phase was extracted with CH$_2$Cl$_2$ (3×40 mL). The organic phase was then dried over MgSO$_4$, filtered, and concentrated down under reduced pressure. The product was chromatographed with ethyl acetate/hexane (1:3). $^1$H NMR (DMSO-d$_6$) δ 2.24 (s, 3H), 4.95 (s, 2H), 5.15, (s, 2H), 6.87 (s, 1H), 6.94 (s, 1H), 7.19–7.20 (d, 1H), 7.30–7.32, (d, 1H), 7.47 (s, 1H), 7.69 (s, 1H), 7.55–7.56 (d, 1H), 8.10 (s, 1H), 9.76 (s, 1H) ppm. MS: M$^+$+1=348 Da.

Example 115

4-(3-Furan-3-yl-5-methyl-benzyl)-6-(4-oxo-2-thioxo-thiazolidin-5-ylidenemethyl)-4H-benzo[1,4]oxazin-3-one The title compound was synthesized in a manner analogous to Example 1 from intermediate 52. $^1$H NMR (DMSO-d$_6$) δ 2.20–2.25 (s, 3H), 4.90–5.00 (s, 2H), 5.15–5.20 (s, 2H), 6.85–6.90 (s, 1H), 7.00–7.15 (d, 1H) 7.19–7.20, (d, 1H), 7.20–7.35 (m, 3H), 7.42–7.45 (s, 1H), 7.65–7.79 (s, 1H), 8.10–8.15 (s, 1H) ppm. MS: M$^+$+1=463 Da.

Intermediate 53: 4-(3-Methyl-5-thiophene-3-yl-benzyl)-3-oxo-3,4-dihydro-2H-benzo[1,4]-oxazine-6-carbaldehyde. The title compound was synthesized in a manner similar to intermediate 52 from intermediate 51 and thiophene-3-boronic acid.

Example 116

4-(3-Methyl-5-thiophene-3-yl-benzyl)-6-(4-oxo-2-thioxo-thiazolidin-5-ylidenemethyl)-4H-benzo[1,4]oxazin-3-one The compound was synthesized in a manner analogous to Example 1 from intermediate 53. $^1$H NMR (DMSO-d$_6$) δ 2.32 (s, 3H), 4.95 (s, 2H), 5.16(s, 2H), 7.05–7.08 (d, 1H), 7.12–7.14 (d, 2H), 7.23–7.25, (d, 1H), 7.39–7.41 (d, 1H), 7.46–7.47 (d, 3H), 7.55–7.56 (s, 1H), 7.77 (s, 1H) ppm. MS: M$^+$+1=479 Da.

Intermediate 54: 4-[3-(3,5-Dimethyl-isoxazol-4-yl)-5-methyl-benzyl)-3-oxo-3,4-dihydro-2H-benzo[1,4]-oxazine-6-carbaldehyde. The title compound was synthesized in a manner similar to intermediate 52 from intermediate 51 and 3,5-dimethylisoxazol-4-boronic acid.

Example 117

4-[3-(3,5-Dimethyl-isoxazol-4-yl)-5-methyl-benzyl]-6-(4-oxo-2-thioxo-thiazolidin-5-ylidenemethyl)-4H-benzo[1,4]oxazin-3-one The title compound was synthesized in a manner analogous to Example 1 from intermediate 54. $^1$H NMR (DMSO-d$_6$) δ 2.07 (s, 3H), 2.25 (s, 3H), 2.34 (s, 3H), 4.92 (s, 2H), 5.18 (s, 2H), 7.01–7.16, (m, 5H), 7.22–7.24 (d, 1H), 7.47 (s, 1H) ppm. MS: M$^+$+1=492 Da.

Example 118

3-Methyl-5-[3-oxo-6-(4-oxo-2-thioxo-thiazolidin-5-ylidenemethyl)-2,3-dihydro-benzo[1,4]oxazin-4-ylmethyl-benzoic acid methyl ester $^1$H NMR (DMSO-d$_6$) δ 2.35 (s, 3H), 3.80 (s, 3H), 4.94 (s, 2H), 5.22 (s, 2H), 7.05 (s, 1H), 7.15–7.17 (d, 1H), 7.26–7.28 (d, 1H), 7.41 (s, 1H), 7.50 (s, 1H), 7.68 (d, 1H) ppm. MS: M$^+$+1=455 Da.

Intermediate 55: 4-(3-Methyl-5-thiazol-2-yl-benzyl)-3-oxo-3,4-dihydro-2H-benzo[1,4]-oxazine-6-carbaldehyde. The title compound was synthesized in a manner similar to intermediate 52 from intermediate 51 and 2-tributyltinthiazole.

Example 119

4-(3-Methyl-5-thiazol-2-yl-benzyl)-6-(4-oxo-2-thioxo-thiazolidin-5-ylidenemethyl)-4H-benzo[1,4]oxzain-3-one The title compound was synthesized in a manner analogous to Example 1 from intermediate 55. $^1$H NMR (DMSO-$d_6$) δ 2.36 (s, 3H), 4.94 (s, 2H), 5.23 (s, 2H), 7.13–7.16 (d, 2H), 7.25 (s, 2H), 7.40–7.50, (b, 1H), 7.70 (t, 3H), 7.86 (s, 1H) ppm. MS: $M^+$+1=480 Da.

Intermediate 56: 3-(6-Formyl-3-oxo-2,3-dihydro-benzo[1,4]oxazin-4-ylmethyl)-5-methyl-benzonitrile. The title compound was synthesized in a manner similar to intermediate 28 from intermediate 51 and zinc cyanide.

Example 120

3-Methyl-5-[3-oxo-6-(4-oxo-2-thioxo-thiazolidin-5-ylidenemethyl)-2,3-dihydro-benzo[1,4]oxazin-4-ylmethyl-benzonitrile The title compound was synthesized in a manner analogous to Example 1 from intermediate 56. $^1$H NMR (DMSO-$d_6$) δ 2.37 (s, 3H), 4.96 (s, 2H), 5.18 (s, 2H), 6.94 (s, 1H), 7.14–7.16, (d, 1H), 7.25–7.26 (d, 1H), 7.50 (s, 1H), 7.54–7.57 (d, 3H) ppm. MS: $M^+$+1=422 Da.

Intermediate 57: 4-(3-Methyl-5-pyrazin-2-yl-benzyl)-3-oxo-3,4-dihydro-2H-benzo[1,4]-oxazine-6-carbaldehyde. To a solution of intermediate 51 (0.150 g, 0.368 mmol) and Pd(PPh$_3$)$_4$ in dry DMF (15 mL) was added 2-tributylstannylpyrazine (0.025 g, 0.04 mmol) followed by CuI (0.014 g, 0.07 mmol). The solution was heated to reflux and monitored by TLC. The heat was turned off and the solution was filtered through celite. The solution was then concentrated down under reduced pressure, dissolved in CH$_3$CN and extracted with hexane (5×30 mL). The organic phase was dried over MgSO$_4$, filtered, and concentrated down under reduced pressure. The product was chromatographed with ethyl acetate/hexane (1:3). $^1$H NMR (DMSO-$d_6$) δ 2.35 (s, 3H), 4.98 (s, 2H), 5.26 (s, 2H), 7.20–7.22 (d, 2H), 7.52–7.56 (m, 2H), 7.84–7.90 (d, 2H), 8.59 (s, 1H), 8.68 (s, 1H), 9.19 (s, 1H), 9.78 (s, 1H) ppm. MS: $M^+$+1=360 Da.

Example 121

4-(3-Methyl-5-pyrazin-2-yl-benzyl)-6-(4-oxo-2-thioxo-thiazolidin-5-ylidenemethyl)-4H-benzo[1,4]oxazin-3-one The title compound was synthesized in a manner analogous to Example 1 from intermediate 57. $^1$H NMR (DMSO-$d_6$) δ 2.38 (s, 3H), 4.97 (s, 2H), 5.25 (s, 2H), 7.08 (s, 1H), 7.14–7.16 (s, 2H), 7.26 (s, 2H), 7.47 (s, 1H), 7.88–7.91(d, 1H), 8.57 (s, 1H), 8.67 (s, 1H), 9.20 (s, 1H) ppm. MS: $M^+$+1=475 Da.

Intermediate 58: 4-[3-(4-Methoxy-phenyl)-propyl]-3-oxo-chrom-6-carbaldehyde. The title compound was synthesized in a manner analogous to intermediate 4 using intermediate 3 and 1-(3-iodo-propyl)-4-methoxy-benzene.

Example 122

4-[3-(4-Methoxy-phenyl)-propyl]-6-(4-oxo-2-thioxo-thiazolidin-5-ylidenemethyl)-4H-benzo[1,4]oxazin-3-one $^1$H NMR (DMSO-$d_6$) δ 1.85 (t, 2H), 2.60 (t, 2H), 3.91, (t, 2H), 4.72 (s, 2H), 6.81–6.83 (d, 2H), 7.12, (t, 3H), 7.13–7.14 (d, 1H), 7.35 (s, 1H), 7.66 (s, 1H) ppm. MS: $M^+$+1=441 Da.

Example 123

5-{4-[3-(4-Methoxy-phenyl)-propyl]-3-oxo-3,4-dihydro-2H-benzo[1,4]oxazin-6-ylmethylene}-thiazolidine-2,4-dione The title compound was synthesized in a manner analogous to Example 66. $^1$H NMR (DMSO-$d_6$) δ 1.84 (t, 2H), 2.448 (t, 2H), 3.69, (t, 3H), 3.90 (s, 2H), 4.70 (s, 2H), 6.81–6.83 (d, 2H), 7.11–7.13 (m, 4H), 7.20, (s, 1H), 7.34 (s, 1H), 7.80 (s, 1H) ppm. MS: $M^+$+1=425 Da.

Example 124

6-(4-Oxo-2-thioxo-thiazolidin-5-ylidenemethyl)-4-[3-(3,4,5-trimethoxy-phenyl)-propyl]-4H-benzo[1,4]oxazin-3-one $^1$H NMR (DMSO-$d_6$) δ 1.92 (t, 2H), 2.62 (t, 2H), 3.58, (s, 3H), 3.71 (s, 6H), 3.97 (t, 2H), 4.71 (s, 2H), 6.49 (s, 1H), 7.11–7.13 (d, 2H), 7.21–7.22 (d, 1H), 7.44 (s, 1H), 7.66 (s, 1H) ppm. MS: $M^+$+1=501 Da.

Example 125

5-{4-[3-(4-Methoxy-phenyl)-propyl]-3-oxo-3,4-dihydro-2H-benzo[1,4]oxazin-6-ylmethylene}-thiazolidine-2,4-dione The title compound was synthesized in a manner analgous to Example 66. $^1$H NMR (DMSO-$d_6$) δ 1.92 (t, 2H), 2.61 (t, 2H), 3.58 (s, 3H), 3.71 (s, 6H), 3.95 (t, 2H), 4.70 (s, 2H), 6.49 (s, 2H), 7.12–7.14 (d, 1H), 7.22–7.23 (d, 1H), 7.43 (s, 1H), 7.82 (s, 1H) ppm. MS: $M^+$+1=485 Da.

Example 126

Acetic acid 2,6-dimethyl-4-{3-[3-oxo-6-(4-oxo-2-thioxo-thiazolidin-5-ylidenemethyl)-2,3-dihydro-benzo[1,4]oxazin-4-yl]-methyl}-phenyl ester $^1$H NMR (DMSO-$d_6$) δ 2.06 (s, 6H), 2.28 (s, 3H), 4.93 (s, 2H), 5.10 (s, 2H), 7.05–7.08 (d, 3H), 7.15 (d, 1H), 7.25–7.29 (d, 1H), 7.51 (s, 1H) ppm. MS: $M^+$+1=469 Da.

Example 127

4-[3-(2,3-Dichloro-phenyl)-propyl]-6-(4-oxo-2-thioxo-thiazolidin-5-ylidenemethyl)-4H-benzo[1,4]oxazin-3-one $^1$H NMR (DMSO-$d_6$) δ 1.89 (t, 2H), 2.68 (t, 2H), 3.93 (t, 2H), 4.71 (s, 2H), 7.12–7.13 (d, 1H), 7.21 (t, 2H), 7.41 (s, 1H), 7.50 (s, 2H), 7.69 (s, 1H) ppm. MS: $M^+$+1=480 Da.

Example 128

4-(5-tert-Butyl-2-methyl-2H-pyrazol-3-ylmethyl)-6-(4-oxo-2-thioxo-thiazolidin-5-ylidenemethyl)-4H-benzo[1,4]oxazin-3-one $^1$H NMR (DMSO-$d_6$) δ 1.15 (s, 9H), 3.79 (s, 3H), 4.88 (s, 2H), 5.18 (s, 2H), 5.97 (s, 2H), 7.17–7.19 (d, 1H), 7.22–7.23 (d, 1H), 7.32 (s, 1H), 7.60 (s, 1H) ppm. MS: M$^+$+1=443 Da.

Example 129

6-(4-Oxo-2-thioxo-thiazolidin-5-ylidenemethyl)-4-[2-(4-phenoxy-phenyl)-ethyl]-4H-1,4-benzoxazin-3-one MP=220–224° C. MS: M$^+$−1=487.1 Da.

Example 130

4-[2-(3,5-Dimethoxy-phenyl)-ethyl]-6-(4-oxo-2-thioxo-thiazolidin-5-ylidenemethyl)-4H-benzo[1,4]oxazin-3-one MP=267–269° C. MS: M$^+$+1=457.0 Da.

Intermediate 59: 4-[2-(4-tert-Butyl-phenyl)-ethyl]-3-oxo-3,4-dihydro-2H-benzo[1,4]oxazine-6-carbaldehyde. The title compound was synthesized in a manner analogous to intermediate 4 using intermediate 3, potassium iodide, and 1-(4-t-butyl-phenyl)-2-bromoethane.

Example 131

4-[2-(4-tert-Butyl-phenyl)-ethyl]-6-(4-oxo-2-thioxo-thiazolidin-5-ylidenemethyl)-4H-benzo[1,4]-oxazin-3-one The title compound was prepared in a manner analogous to Example 1 from intermediate 59. MP=283–285° C. MS: M$^+$+1=453.2Da.

Example 132

4-[2-(4-Dimethylaniino-phenyl)-ethyl]-6-(4-oxo-2-thioxo-thiazolidin-5-ylidenemethyl)-4H-benzo[1,4]-oxazin-3-one MP=266–268° C. MS: M$^+$+1=440.1 Da.

Intermediate 60: Methanesulfonic acid 2-(3,4-difluorophenyl)-ethyl ester. To a solution of 2-(3,4-difluoro-phenyl)-ethanol (1.00 g, 6.33 mmol) in tetrahydrofuran (63.0 mL) at 0° C. was added triethylamine (1.95 mL, 13.9 mmol) followed by methanesulfonyl chloride (0.538 mL, 6.96 mmol). The solution was allowed to warm to room temperature overnight, quenched with water (20 mL), and diluted with ethyl acetate (100 mL). The layers were separated and the aqueous phase was extracted with ethyl acetate (3×25 mL). The combined organic extracts were washed with saturated NaHCO$_3$ (1×20 mL), brine (1×20 mL), dried over MgSO$_4$, filtered, and concentrated to give the title compound. $^1$H NMR (CDCl$_3$) δ 2.92 (s, 3H), 3.01 (t, J=6.59 Hz, 2H), 4.37–4.40 (m, 2H), 6.94–6.97 (m, 1H), 7.03–7.06 (m, 1H), 7.07–7.15 (m, 1H) ppm. $^{19}$F NMR (CDCl$_3$) δ −140.48–, 137.71 ppm.

Intermediate 61: 4-[2-(3,4-Difluoro-phenyl)-ethyl]-3-oxo-3,4-dihydro-2H-benzo[1,4]oxazine-6-carbaldehyde. To a solution of intermediate 3 (0.500 g, 2.82 mmol) in dry DMF (28.0 mL) at 0° C. was added dropwise potassium bis(trimethylsilyl)amide (5.64 mL, 2.82 mmol). After 25 minutes, a solution of intermediate 60 (1.48 g, 6.26 mmol) in DMF (2 mL) was added dropwise. The solution was warmed to room temperature over 18 hours, diluted with water (30 mL), ethyl acetate (50 mL), and acidified with 1N HCl. The layers were separated and the aqueous phase was extracted with ethyl acetate (3×20 mL). The combined organic extracts were washed with brine (1×20 mL), dried over MgSO$_4$, filtered, and concentrated to give the title compound. The compound was purified by silica gel flash column chromatography (25% ethyl acetate/hexanes, then 20% acetone/hexanes) to afford a white solid. $^1$H NMR (DMSO-$d_6$) δ 2.84–2.88 (m, 2H), 4.17–4.20 (m, 2H), 4.71 (s, 2H), 7.16 (d, J=8.06 Hz), 7.24–7.40 (m, 3H), 7.55–7.66 (m, 1H), 9.89 (s, 1H) ppm. $^{19}$F NMR (CDCl$_3$) δ 142.55, −139.55 ppm. MS: M$^+$+1=318.1 Da.

Example 133

4-[2-(3,4-Difluoro-phenyl)-ethyl]-6-(4-oxo-2-thioxo-thiazolidin-5-ylidenemethyl)-4H-benzo[1,4]oxazin-3-one The title compound was synthesized in a manner analogous to Example 1 from intermediate 61. MP=263–266° C. MS: M$^+$−1=432.1 Da.

Example 134

4-[2-(4-Chloro-phenyl)-ethyl]-6-(4-oxo-2-thioxo-thiazolidin-5-ylidenemethyl)-4H-1,4-benzoxazin-3-one MP=278–280° C. MS: M$^+$−1=430.0 Da.

Example 135

4-[2-(3-Chloro-phenyl)-ethyl]-6-(4-oxo-2-thioxo-thiazolidin-5-ylidenemethyl)-4H-1,4-benzoxazin-3-one The title compound was synthesized in a manner analogous to Example 131. MP=280–282° C. MS: M$^+$−1=430.0 Da.

Example 136

4-[2-(4-Methoxy-phenyl)-ethyl]-6-(4-oxo-2-thioxo-thiazolidin-5-ylidenemethyl)-4H-1,4-benzoxazin-3-one The title compound was synthesized in a manner analogous to Example 131. $^1$H NMR (DMSO-$d_6$) δ 2.79–2.83 (m, 2H), 3.69 (s, 3H), 4.05–4.09 (m, 2H), 4.70 (s, 2H), 6.83 (d, J=8.55 Hz, 1H), 7.16 (d, J=8.55 Hz, 1H), 7.19 (d, J=8.79 Hz, 2H), 7.21–7.24 (m, 1H), 7.45 (d, J=1.71 Hz, 1H), 7.69 (s, 1H), 13.80 (bs, 1H) ppm. MS: M$^+$+1=427.0 Da.

Example 137

4-[2-(3-Methoxy-phenyl)-ethyl]-6-(4-oxo-2-thioxo-thiazolidin-5-ylidenemethyl)-4H-1,4-benzoxazin-3-one The title compound was synthesized in a manner analogous to Example 131. MP=233–236° C. MS: M$^+$−1=426.1 Da.

Example 138

6-(4-Oxo-2-thioxo-thiazolidin-5-ylidenemethyl)-4-(2-p-tolyl-ethyl)-4H-1,4-benzoxazin-3-one The title compound was synthesized in a manner analogous to Example 131. MP=267–269° C. MS: M$^+$−1=410.2 Da.

Example 139

4-Ethyl-6-(4-oxo-2-thioxo-thiazolidin-5-ylidenemethyl)-4H-benzo[1,4]oxazin-3-one.

MS: M$^+$+1=383.0.

Example 140

4-(4-Methyl-benzyl)-6-(4-oxo-2-thioxo-thiazolidin-5-ylidenemethyl)-4H-benzo[1,4]oxazin-3-one Microanalysis ($C_{20}H_{16}N_2O_3S_2$): calculated: C=60.59%, H=4.07%, N=7.07%, O=12.11%, S=16.17%; found: C=60.30%, H=4.16%, N=6.91%. MS: M$^+$−1=395.1 Da.

Intermediate 62: 2-(6-Formyl-3-oxo-2,3-dihydro-benzo[1,4]oxazin-4-yl)-acetamide. The title compound was synthesized as in intermediate 4 using intermediate 3 (0.200 g, 1.13 mmol), and 2-bromoacetamide (0.233 g, 1.69 mmol) and a catalytic amount of sodium iodide. MS: M$^+$+1=235.1 Da.

Example 141

2-[3-Oxo-6-(4-oxo-2-thioxo-thiazolidin-5-ylidenemethyl)-2,3-dihydro benzo[1,4]oxazin-4-yl]-acetamide The title compound was synthesized in a manner analogous to Example 1 using intermediate 62. MS: M$^+$+1=348.1 Da.

Example 142

4-(3-Methyl-benzyl)-6-(4-oxo-2-thioxo-thiazolidin-5-ylidenemethyl)-4H-benzo[1,4]oxazin-3-one The title compound was synthesized in a manner analogous to Example 141. Microanalysis ($C_{20}H_{16}N_2O_3S_2$): calculated: C=60.59%, H=4.07%, N=7.07%, O=12.11%, S=16.17%; found: C=60.35%, H=4.36%, N=6.70%. MS: M$^+$−1=395.1 Da.

Example 143

4-Cyclohexylmethyl-6-(4-oxo-2-thioxo-thiazolidin-5-ylidenemethyl)-4H-benzo[1,4]oxazin-3-one The title compound was synthesized in a manner analogous to Example 141. Microanalysis ($C_{19}H_{20}N_2O_3S_2$): calculated: C=58.74%, H=5.19%, N=7.21%, O=12.35%, S=16.51%; found: C=58.49%, H=5.27%, N=7.13%. MS: M$^+$+1=389.2 Da.

Example 144

4-(3-Methyl-butyl)-6-(4-oxo-2-thioxo-thiazolidin-5-ylidenemethyl)-4H-benzo[1,4]oxazin-3-one Microanalysis ($C_{17}H_{18}N_2O_3S_2$): calculated: C=56.33%, H=5.01%, N=7.73%, O=13.24%, S=17.69%; found: C=55.70%, H=4.77%, N=7.54%. MS: M$^+$−1=361.2 Da.

Example 145

4-Cyclopropylmethyl-6-(4-oxo-2-thioxo-thiazolidin-5-ylidenemethyl)-4H-benzo[1,4]oxazin-3-one MS: M$^+$−1=345.1 Da.

Example 146

6-(4-Oxo-2-thioxo-thiazolidin-5-ylidenemethyl)-4-thiophen-3-ylmethyl-4H-benzo[1,4]oxazin-3-one MS: M$^+$−1=387.1 Da.

Intermediate 63: 3-Oxo-4-pyridin-2-ylmethyl-3,4-dihydro-2H-benzo[1,4]oxazine-6-carbaldehyde. To a solution of DMF and intermediate 3 (0.300 g, 2.03 mmol) was added sodium hydride (0.085 g, 3.54 mmol) and 3-(bromomethyl)pyridine hydrobromide (0.470 g, 1.85 mmol). The reaction stirred at room temperature for 24 hours. The DMF was removed in vacuo, and the reaction mixture was diluted with ethyl acetate, washed with NaHCO$_3$, and brine. The organic layer was dried with magnesium sulfate and concentrated. MS: M$^+$+1=269.2 Da.

Example 147

6-(4-Oxo-2-thioxo-thiazolidin-5-ylidenemethyl)-4-pyridin-2-ylmethyl-4H-benzo[1,4]oxazin-3-one The title compound was synthesized as in Example 1 using intermediate 63. MS: M$^+$+1=384.2 Da.

Example 148

6-(4-Oxo-2-thioxo-thiazolidin-5-ylidenemethyl)-4-pyridin-4-ylmethyl-4H-benzo[1,4]oxazin-3-one MS: M$^+$+1=384.2 Da.

Example 149

3-[3-Oxo-6-(4-oxo-2-thioxo-thiazolidin-5-ylidenemethyl)-2,3-dihydro-benzo[1,4]oxazin-4-ylmethyl]-benzonitrile MS: M$^+$−1=406.2 Da.

Example 150

4-(3,5-Dimethyl-benzyl)-6-(4-oxo-2-thioxo-thiazolidin-5-ylidenemethyl)-4H-benzo[1,4]oxazin-3-one MS: M$^+$−1=409.2 Da.

Example 151

4-Biphenyl-4-ylmethyl-6-(4-oxo-2-thioxo-thiazolidin-5-ylidenemethyl)-4H-benzo[1,4]oxazin-3-one. MS M$^+$−1=457.2 Da.

Example 152

(S)-2-Methyl-4-naphthalen-2-ylmethyl-6-(4-oxo-2-thioxo-thiazolidin-5-ylidenemethyl)-4H-benzo[1,4]oxazin-3-one The title compound was synthesized in a manner analogous to Example 18. MS: M$^+$−1=447.1 Da.

Example 153

4-Benzyl-8-methoxy-6-(4-oxo-2-thioxo-thiazolidin-5-ylidenemethyl)-4H-benzo[1,4]oxazin-3-one The title compound was synthesized as in Example 2 using intermediate 10 and rhodanine. MS: M$^+$−1=411.0 Da.

Example 154

8-Methyl-6-(4-oxo-2-thioxo-thiazolidin-5-ylidenemethlyl)-4H-benzo[1,4]oxazin-3-one The title compound was synthesized as in Example 1 using intermediate 20. MS: M$^+$−1=305.1 Da.

Examples 155–188 were synthesized in a synthesized in a manner analogous to Example 38.

Example 155

4-(3,3-Dimethyl-butyl)-6-(4-oxo-2-thioxo-thiazolidin-5-ylidenemethyl)-4H-1,4-benzoxazin-3-one MS: M$^+$+1=377.52 Da.

Example 156

6-(4-Oxo-2-thioxo-thiazolidin-5-ylidenemethyl)-4-(3-trifluoromethoxy-benzyl)-4H-1,4-benzoxazin-3-one MS :M$^+$+1=467.47 Da.

Example 157

6-(4-Oxo-2-thioxo-thiazolidin-5-ylidenemethyl)-4-(3-trifluoromethyl-benzyl)-4H-1,4-benzoxazin-3-one MS :M$^+$+1=451.47 Da.

Example 158

6-(4-Oxo-2-thioxo-thiazolidin-5-ylidenemethyl)-4-(4-trifluoromethyl-benzyl)-4H-1,4-benzoxazin-3-one MS:M$^+$+1=451.47 Da.

Example 159

4-Biphenyl-2-ylmethyl-6-(4-oxo-2-thioxo-thiazolidin-5-ylidenemethyl)-4H-1,4-benzoxazin-3-one MS: M$^+$+1=459.57 Da.

Example 160

6-(4-Oxo-2-thioxo-thiazolidin-5-ylidenemethyl)-4-(3-phenyl-propyl)-4H-1,4-benzoxazin-3-one MS: M$^+$+1=411.53 Da.

Example 161

6-(4-Oxo-2-thioxo-thiazolidin-5-ylidenemethyl)-4-(3-phenoxy-propyl)-4H-1,4-benzoxazin-3-one MS: M$^+$+1=427.53 Da.

Example 162

6-(4-Oxo-2-thioxo-thiazolidin-5-ylidenemethyl)-4-(4-styryl-benzyl)-4H-1,4-benzoxazin-3-one MS: M$^+$+1=485.61 Da.

Example 163

4-(4-Benzyloxy-benzyl)-6-(4-oxo-2-thioxo-thiazolidin-5-ylidenemethyl)-4H-1,4-benzoxazin-3-one MS: M$^+$+1=489.6 Da.

Example 164

4-(3-Difluoromethoxy-benzyl)-6-(4-oxo-2-thioxo-thiazolidin-5-ylidenemethyl)-4H-1,4-benzoxazin-3-one.

MS: M$^+$+1=449.48 Da.

Example 165

6-(4-Oxo-2-thioxo-thiazolidin-5-ylidenemethyl)-4-(3-trifluoromethylsulfanyl-benzyl)-4H-1,4-benzoxazin-3-one MS: M$^+$+1=483.53 Da.

Example 166

6-(4-Oxo-2-thioxo-thiazolidin-5-ylidenemethyl)-4-(2-trifluoromethoxy-benzyl)-4H-1,4-benzoxazin-3-one MS:M$^+$+1=467.47 Da.

Example 167

4-(4-Methoxy-3-trifluoromethyl-benzyl)-6-(4-oxo-2-thioxo-thiazolidin-5-ylidenemethyl)-4H-1,4-benzoxazin-3-one MS: M$^+$+1=481.5 Da.

Example 168

6-(4-Oxo-2-thioxo-thiazolidin-5-ylidenemethyl)-4-(4-trifluoromethylsulfanyl-benzyl)-4H-1,4-benzoxazin-3-one MS: $M^+ +1 = 483.53$ Da.

Example 169

6-(4-Oxo-2-thioxo-thiazolidin-5-ylidenemethyl)-4-(2-trifluoromethylsulfanyl-benzyl)-4H-1,4-benzoxazin-3-one MS: $M^+ +1 = 483.53$ Da.

Example 170

6-(4-Oxo-2-thioxo-thiazolidin-5-ylidenemethyl)-4-(3-phenoxy-benzyl)-4H-1,4-benzoxazin-3-one MS: $M^+ +1 = 475.57$ Da.

Example 171

4-Bicyclo[2.2.1]hept-5-en-2-ylmethyl-6-(4-oxo-2-thioxo-thiazolidin-5-ylidenemethyl)-4H-1,4-benzoxazin-3-one MS: $M^+ +1 = 399.52$ Da.

Example 172

3-[3-Oxo-6-(4-oxo-2-thioxo-thiazolidin-5-ylidenemethyl)-2,3-dihydro-1,4-benzoxazin-4-ylmethyl]-benzamide MS: $M^+ +1 = 426.5$ Da.

Example 173

6-(4-Oxo-2-thioxo-thiazolidin-5-ylidenemethyl)-4-(2-phenyl-propyl)-4H-1,4-benzoxazin-3-one MS: $M^+ +1 = 411.53$ Da.

Example 174

6-(4-Oxo-2-thioxo-thiazolidin-5-ylidenemethyl)-4-(4-phenyl-butyl)-4H-1,4-benzoxazin-3-one MS: $M^+ +1 = 425.56$ Da.

Example 175

6-(4-Oxo-2-thioxo-thiazolidin-5-ylidenemethyl)-4-(5-phenyl-pentyl)-4H-1,4-benzoxazin-3-one MS: $M^+ +1 = 439.59$ Da.

Example 176

4-[3-Oxo-6-(4-oxo-2-thioxo-thiazolidin-5-ylidenemethyl)-2,3-dihydro-1,4-benzoxazin-4-ylmethyl]-benzamide MS: $M^+ +1 = 426.5$ Da.

Example 177

N-{4-[3-Oxo-6-(4-oxo-2-thioxo-thiazolidin-5-ylidenemethyl)-2,3-dihydro-1,4-benzoxazin-4-ylmethyl]-phenyl}-acetamide MS: $M^+ +1 = 440.53$ Da.

Example 178

4-(3,4-Dichloro-benzyl)-6-(4-oxo-2-thioxo-thiazolidin-5-ylidenemethyl)-4H-1,4-benzoxazin-3-one MS: $M^+ +1 = 452.35$ Da.

Example 179

4-(4-Chloro-benzyl)-6-(4-oxo-2-thioxo-thiazolidin-5-ylidenemethyl)-4H-1,4-benzoxazin-3-one MS: $M^+ +1 = 417.91$ Da.

Example 180

4-Benzyl-6-(4-oxo-2-thioxo-thiazolidin-5-ylidenemethyl)-4H-1,4-benzoxazin-3-one

MS: $M^+ +1 = 383.47$ Da.

Example 181

4-(3,5-Dimethyl-benzyl)-6-(4-oxo-2-thioxo-thiazolidin-5-ylidenemethyl)-4H-1,4-benzoxazin-3-one MS: $M^+ +1 = 411.53$ Da.

Example 182

4-(4-Methoxy-benzyl)-6-(4-oxo-2-thioxo-thiazolidin-5-ylidenemethyl)-4H-1,4-benzoxazin-3-one MS: $M^+ +1 = 413.5$ Da.

Example 183

4-(4-Nitro-benzyl)-6-(4-oxo-2-thioxo-thiazolidin-5-ylidenemethyl)-4H-1,4-benzoxazin-3-one MS: $M^+ +1 = 428.47$ Da.

Example 184

4-(4-tert-Butyl-benzyl)-6-(4-oxo-2-thioxo-thiazolidin-5-ylidenemethyl)-4H-1,4-benzoxazin-3-one MS: $M^+ +1 = 439.59$ Da.

Example 185

4-(3,5-Bis-trifluoromethyl-benzyl)-6-(4-oxo-2-thioxo-thiazolidin-5-ylidenemethyl)-4H-1,4-benzoxazin-3-one MS: $M^+ +1 = 519.47$ Da.

Example 186

4-(2-Dibenzofuran-3-yl-2-oxo-ethyl)-6-(4-oxo-2-thioxo-thiazolidin-5-ylidenemethyl)-4H-1,4-benzoxazin-3-one MS: $M^++1=501.56$ Da.

Example 187

4-(3-Fluoro-5-trifluoromethyl-benzyl)-6-(4-oxo-2-thioxo-thiazolidin-5-ylidenemethyl)-4H-1,4-benzoxazin-3-one MS: $M^++1=469.46$ Da.

Example 188

4-Naphthalen-2-ylmethyl-6-(4-oxo-2-thioxo-thiazolidin-5-ylidenemethyl)-4H-1,4-benzoxazin-3-one MS: $M^++1=433.53$ Da.

Intermediate 64: 5-Bromo-2-chloro-3-nitropyridine. In DMF (40 mL) was stirred 5-bromo-3-nitro-2-pyridinol (8.76 g, 40 mmol) and the solution treated dropwise with phosphorus oxychloride (28 mL). The solution warmed to 80° for 5 hours. The mixture was cooled to room temperature and carefully poured into a mixture of ice and water (400 mL). This mixture was stirred overnight to precipitate. The solid was collected by filtration, washed with water (2×100 mL) and dried at 65° C. on the high vacuum line for 3 hours to give the title compound. MS: $M^+-1=237.9$ Da.

Intermediate 65: (5-Bromo-3-nitropyridin-2-yloxy)acetic acid methyl ester. A solution of methylglycolate (1.62 g, 18 mmol) in THF (30 mL) was treated with NaH (0.48 g, 20 mmol) and stirred at 0° C. for 0.5 hours. This solution was then added via syringe to a solution of intermediate 64 (3.0 g, 12.6 mmol) in THF (30 mL) and stirred at room temperature, overnight. The mixture was evaporated at reduced pressure until free of THF. The residue was partitioned between ethyl acetate (110 mL) and water (100 mL). The organic phase was separated and washed with brine (100 mL) and then dried over magnesium sulfate. The solvents were evaporated at reduced pressure to give a yellow solid which was purified by MPLC (40 g silica gel column, 7:3 [hexane/ethyl acetate]). The appropriate fractions were combined and evaporated at reduced pressure to give the title compound as a white solid. MS: $M^++1=292.9$ Da.

Intermediate 66: 7-Bromo-1H-pyrido[2,3-b][1,4]oxazin-2-one. In concentrated hydrochloric acid (8 mL) was stirred intermediate 65 (1.0 g, 3.43 mmol) which was then cooled to 0° C. This was then treated, in parts, with tin dust (0.92 g, 7.8 mmol) and then warmed to 80° C. for 1 hour. The mixture was cooled to room temperature and diluted with water (100 mL). The mixture was stirred to form a precipitate. The solid was collected by filtration, washed with water (10 mL), and dried at 65° C. for 3 hours under a vacuum to give the title compound. MS: $M^++1=230.9$ Da. Intermediate 67: 1-Benzyl-7-bromo-1H-pyrido[2,3-b][1,4]oxazin-2-one. In DMF (30 mL) was stirred intermediate 66 (650 mg, 2.83 mmol) and cesium carbonate (3.9 g, 12 mmol). To this was added, dropwise, benzyl bromide (513 mg, 3.0 mmol) and the mixture was stirred overnight at room temperature. The mixture was filtered free of insolubles and the DMF was evaporated at reduced pressure to give a crude oil which was purified by MPLC (90 g silica gel column, 9:1 (methylene chloride/ethyl acetate). The appropriate fractions were combined and evaporated at reduced pressure to give the title compound. MS: $M^++1=321.0$ Da.

Intermediate 68: 1-Benzyl-2-oxo-2,3-dihydro-1H-pyrido[2,3-b][1,4]oxazine-7-carbaldehyde. In DMF (6 mL) was stirred intermediate 67 (0.61 g, 1.9 mmol), sodium formate (272 mg, 4.0 mmol) and bis(triphenylphosphine)palladium (II) dichloride (280 mg, 0.4 mmol). The mixture was treated with a continuous stream of carbon monoxide (bubbled into the solution) and warmed to 100° C. The mixture was heated for 5 hours and then cooled to room temperature. The dark solution was treated with ethyl acetate (100 mL) and sodium bicarbonate (100 mL) and filtered through celite. The organic phase was separated and dried over magnesium sulfate. The solvents were evaporated at reduced pressure to give a dark oil which was purified by MPLC (90 g silica gel column, 9:1 [methylene chloride/ethyl acetate]). The appropriate fractions were combined and evaporated in vacuo to give the named product as a thick oil. MS: $M^+-1=268.1$ Da.

Example 189

1-Benzyl-7-(4-oxo-2-thioxo-thiazolidin-5-ylidenemethyl)-1H-pyrido[2,3-b][1,4]oxazin-2-one; compound with ethane-1,2-diamine The title compound was synthesized in a manner analogous to Example 1 using intermediate 68. Microanalysis ($C_{18}H_{13}N_3O_3S_2 \cdot 0.5$ ethylenediamine $0.5H_2O$): calculated: C=53.93, H=4.25, N=13.12, S=15.57; found: C=54.00, H=4.29, N=13.26, S=15.18. MS: $M^+-1=383$ Da.

Intermediate 69: [Methyl-(2-nitrophenyl)-amino]acetic acid tert-butylester. In acetonitrile (80 mL) was stirred sarcosine t-butyl ester•hydrochloride (10.1 g, 55.5 mmol) and triethylamine (6.57 g, 65 mmol). To this was added 2-fluoronitrobenzene (5.66 g, 40 mmol) and the mixture was stirred overnight at 50° C. The solution was evaporated at a reduced pressure until free of acetonitrile. The residue was partitioned between ether (100 m]L) and water (100 mL). The ether layer was washed with brine and dried over magnesium sulfate. The solvent was evaporated at reduced pressure to give an oil which was dried at 60° C. in vacuo to remove all traces of fluoronitrobenzene. MS: $M^++1=267.1$ Da.

Intermediate 70: 4-Methyl-3,4-dihydro-1H-quinoxalin-2-one. A solution of intermediate 69 (9.2 g, 34.5 mmol) in methanol (50 mL) was treated with 20% Pd/C (1 g) and subjected to a hydrogen atmosphere at 100 psi/mole. The mixture was filtered free of catalyst and evaporated at reduced pressure to give the title compound. MS: $M^++1=163.1$ Da.

Intermediate 71: 6-Bromo-4-methyl-3,4-dihydro-1H-quinoxalin-2-one. In acetic acid (250 mL) was dissolved intermediate 70 (5.1 g, 31.4 mmol), which was cooled to near 0° C. To this was added a solution of bromine (5.1 g, 32 mmol) in acetic acid (60 mL). The mixture was warmed to room temperature and stirred for 1 hour. The solution was then filtered to collect a dark solid. The solid was washed with water (3×150 mL) and air dried for 1 hour. The solid was stirred into concentrated ammonium hydroxide (100 mL) and filtered to collect the solid. The solid was then dried in vacuo at 65° C. for 3 hours and then recrystallized from ethanol/water. The resultant tan solid was collected by filtration and dried at 65° C. in vacuo for 3 hours. MS: $M^++1=240.9$ Da.

Intermediate 72: 1-Methyl-3-oxo-1,2,3,4-tetrahydroquinoxaline-6-carbaldehyde. The title compound was synthe-

Example 190

4-Methyl-7-(4-oxo-2-thioxo-thiazolidin-5-ylidenemethyl)-3,4-dihydro-1H-quinoxalin-2-one The title compound was synthesized in a manner analogous to Example 1 using intermediate 72. Microanalysis ($C_{13}H_{11}N_3O_2S_2.0.15H_2O$): calculated: C=50.68, H=3.70, N=13.64, $H_2O$=0.88; found: C=50.31, H=3.70, N=13.47, $H_2O$=0.68. MS: $M^+$−1=306 Da.

Example 191

4-(3,4-Dichloro-benzyl)-6-(4-oxo-2-thioxo-oxazolidin-5-ylidenemethyl)-4H-1,4-benzoxazin-3-one Microanalysis ($C_{19}H_{12}Cl_2N_2O_4S.0.3H_2O$): calculated: C=51.78, H=2.88, N=6.36, S=7.27; found: C=51.71, H=2.81, N=5.96, S=6.81. MS: $M^+$+1=436.8 Da.

Example 192

4-(4-Methanesulfonyl-benzyl)-6-(4-oxo-2-thioxo-thiazolidin-5-ylidenemethyl)-4H-1,4-benzoxazin-3-one Microanalysis ($C_{20}H_{16}N_2O_5S_3$): calculated: C=52.16, H=3.50, N=6.08, S=20.89; found: C=51.99, H=3.51, N=5.98, S=20.65. MS: $M^+$−1=459.9 Da.

Example 193

4-(4-Methanesulfonyl-benzyl)-6-(4-oxo-2-thioxo-thiazolidin-5-ylidenemethyl)-4H-1,4-benzoxazin-3-one, Potassium Salt In methanol (10 mL) was stirred Example 192 (502 mg, 1.1 mmol) and the mixture was treated with a solution of potassium hydroxide (0.498N) in methanol (2.18 m]L, 1.1 mmol). The mixture was warmed to reflux, cooled, and evaporated to dryness. The residue was then triturated with ether (50 mL) and the resultant solid collected by filtration. ($C_{20}H_{15}N_2O_5S_3K.0.1H_2O$): calculated: C=47.99, H=3.06, N=5.60, $H_2O$=0.36; found: C=47.82, H=2.78, N=5.55, $H_2O$=0.27. MS: $M^+$+1=461.0 Da.

Example 194

4-(4-Chloro-3-trifluoromethylbenzyl)-6-(4-oxo-2-thioxo-thiazolidin-5-ylidenemethyl)-4H-1,4-benzoxazin-3-one, Potassium Salt 4-(4-Chloro-3-trifluoromethylbenzyl)-6-(4-oxo-2-thioxo-thiazolidin-5-ylidenemethyl)-4H-1,4-benzoxazin-3-one was synthesized in a manner similar to that described for Example 2. The potassium salt of 4-(4-Chloro-3-trifluoromethylbenzyl)-6-(4-oxo-2-thioxo-thiazolidin-5-ylidenemethyl)-4H-1,4-benzoxazin-3-one was generated in a manner similar to that of Example 193 with methanol and KOH. Microanalysis ($C_{20}H_{12}F_3ClN_2O_3S_2$): calculated: C=49.54, H=2.49, N=5.78, S=13.22; found: C=49.60, H=2.41, N=5.74, S=13.05. MS: $M^+$+1=484.9 Da.

Example 195

7-(4-Oxo-2-thioxo-thiazolidin-5-ylidenemethyl)-1H-pyrido[2,3-b][1,4]oxazin-2-one The title compound was synthesized in an analogous manner to Example 190. Microanalysis ($Cl_{11}H_7N_3O_3S_2.0.2H_2.0.5$ MeOH): calculated: C=44.13, H=3.03, N=13.43, $H_2O$=1.15; found: C=44.00, H=3.03, N=13.05, $H_2O$=1.02. MS: $M^+$−1=292.0 Da.

Example 196

4-(4-Chloro-3-trifluoromethyl-benzyl)-6-(4-oxo-2-thioxo-oxazolidin-5-ylidenemethyl)-4H-1,4-benzoxazin-3-one The title compound was synthesized in a manner analogous to Example 84. Microanalysis ($C_{20}H_{12}F_3ClN_2O_4S.0.2H_2O$): calculated: C=50.84, H=2.64, N=5.93; found: C=50.83, H=2.43, N=5.88. MS: $M^+$+1=468.9 Da.

Example 197

1-Benzyl-4-methyl-7-(4-oxo-2-thioxo-thiazolidin-5-ylidenemethyl)-3,4-dihydro-1H-quinoxalin-2-one The title compound was synthesized in a manner analogous to Example 190. Microanalysis ($C_{20}H_{17}N_3O_2S_2$): calculated: C=60.74, H=4.33, N=10.62; found: C=60.54, H=4.21, N=10.48. MS: $M^+$−1=394.0 Da.

Example 198

4-(3,4-Dichloro-benzyl)-6-(4-oxo-2-thioxo-thiazolidin-5-ylidenemethyl)-4H-1,4-benzothiazin-3-one The title compound was synthesized in an analogous manner to Example 81. Microanalysis ($C_{19}H_{12}Cl_2N_2O_2S_3.0.15H_2O$): calculated: C=48.54, H=2.64, N=5.96, S=20.46, $H_2O$=0.57; found: C=48.41, H=2.43, N=5.80, S=20.44, $H_2O$=0.43. MS: $M^+$−1=468.9 Da.

Example 199

4-(3,4-Dichlorobenzyl)-6-(4-oxo-2-thioxo-oxazolidin-5-ylidenemethyl)-4H-benzo[1,4]thiazin-3-one The title compound was synthesized in a manner analogous to Example 84 using intermediate 94. Microanalysis ($C_{19}H_{12}Cl_2N_2O_3S_2$): calculated: C=50.56, H=2.68, N=6.21, S=14.21; found: C=50.36, H=2.85, N=5.82, S=13.95. MS: $M^+$−1=451.9 Da.

Example 200

6-(5-Oxo-2-thioxo-imidazolidin-4-ylidenemethyl)-4H-benzo[1,4]oxazin-3-one

The title product was synthesized in a manner analogous to Example 84, except that thiohydantoin was substituted for 2-thiooxazolid-4-one. Microanalysis ($C_{12}H_9N_3O_3S.0.85H_2O$): calculated: C=49.60, H=3.71, N=14.46, S=10.67; found: C=49.57, H=3.18, N=13.80, S=10.40. MS: $M^+$−1=274.0 Da.

Intermediate 73: 4-(2,6-Di-tert-butylpyridin-4-ylmethyl)-3-oxo-3,4-dihydro-2H-benzo[1,4]oxazine-6-carbaldehyde.

To a solution of intermediate 3 (1.0 g, 5.6 mmol) in N,N-dimethylformamide was added cesium carbonate (5.5 g, 16.8 mmol) and 3,5-di-tert butyl-bromomethylpyridine (1.75 g, 6.7 mmol). The resulting mixture was stirred overnight. The solids were collected by filtration and discarded. The filtrate was concentrated, and the residue was taken up in ethyl acetate. The organic layer was washed with 0.1N HCl, 50 mL water, and 25 mL of brine. The organic layer was dried with magnesium sulfate and concentrated to give a brown oil. Chromatography of the oil with 3:1 hexane/ethyl acetate results in a yellow oil, which was used as is. MS: $M^++1=381.2$ Da.

Example 201

4-(2,6-Di-tert-butyl-pyridin-4-ylmethyl)-6-(4-oxo-2-thioxo-oxazolidin-5-ylidenemethyl)-4H-1,4-benzoxazin-3-one The title compound was synthesized in a manner analogous to Example 84 using intermediate 73. MS: $M^++1=480.2$ Da. Microanalysis $(C_{26}H_{29}N_3O_4S)$: calculated: C=65.11, H=6.09, N=8.76; found: C=66.57, H=6.58, N=8.13.

Example 202

5-(4-Benzyl-3-oxo-3,4-dihydro-2H-1,4-benzoxazin-6-ylmethylene)-thiazolidine-2,4-dione The title compound was synthesized in a manner analogous to Example 201 using thiazolidinedione in place of rhodanine. MS: $M^++1=367.0$ Da. Microanalysis $(C_{19}H_{14}N_2O_4S \cdot 0.72H_2O)$: calculated: C=60.16, H=4.10, N=7.38; found: C=60.16, H=3.90, N=7.52.

Example 203

5-(3-Oxo-3,4-dihydro-2H-1,4-benzoxazin-6-ylmethylene)-oxazolidine-2,4-dione

To 20 mL of anhydrous THF at −78° was added dropwise 11.2 mL of $TiCl_4$ (1.0 M in dichloromethane, 11.2 mmol). A mixture of intermediate 3 (1.0 g, 5.6 mmol) and thiooxazolidinone (1.0 g, 8.5 mmol) was added all at once, and the resulting mixture was stirred. The reaction was allowed to warm to 0° C. and anhydrous pyridine (2.0 mL, 24.7 mmol) was added to the stirring mixture dropwise. Upon addition of the pyridine, the mixture was warmed to room temperature. The reaction was then refluxed for 3 hours, then maintained at 70° C. overnight. The reaction was cooled and diluted with water. The resulting precipitate was collected by filtration and dried under vacuum. The resulting solid was suspended in absolute ethanol and Hunig's base (0.15 mL, 0.8 mmol) and iodomethane (0.07 mL, 1.1 mmol) were added. The reaction was stirred overnight. Concentrated HCl (2 mL) was added, and the mixture was stirred for another 3 hours. The ethanol was removed under reduced pressure, and the resulting residue was partitioned between ethyl acetate and water. The organic layer was dried with magnesium sulfate and concentrated. The brown residue was triturated with ethyl ether, yielding a brown powder. MS: $M^++1=261.0$ Da. Microanalysis $(C_{12}H_8N_2O_5 \cdot 0.74H_2O)$: calculated: C=52.69, H=3.49, N=10.24; found: C=52.79, H=3.25, N=9.85.

Example 204

4-Methyl-6-(4-oxo-2-thioxo-oxazolidin-5-ylidenemethyl)-4a,8a-dihydro-4H-benzo[1,4]oxazin-3-one, Potassium Salt The title compound was prepared in a manner analogous to Example 84 using intermediate 4. The potassium salt was generated by treating 4-methyl-6-(4-oxo-2-thioxo-oxazolidin-5-ylidenemethyl)-4a,8a-dihydro-4H-benzo[1,4]oxazin-3-one in methanol with a solution of KOH in methanol (0.498N, 0.34 mL). The solution was stirred until a cloudy mixture had formed. Approximately half of the methanol was removed under reduced pressure, and the precipitate was collected by filtration and dried under vacuum. Microanalysis $(C_{13}H_9N_2O_4SK \cdot 0.96H_2O)$: calculated: C=45.17, H=3.18, N=8.10; found: C=45.16, H=3.08, N=7.91.

Example 205

4-(2-Chloro-6-methoxy-pyridin-4-ylmethyl)-6-(4-oxo-2-thioxo-thiazolidin-5-ylidenemethyl)-4H-benzo[1,4]oxazin-3-one $^1$H NMR (DMSO-$d_6$) δ 3.81 (s, 3H), 4.93 (s, 2H), 5.12 (s, 2H), 6.77 (s, 1H), 6.97 (s, 1H), 7.04 (s, 1H), 7.14–7.16, (d, 1H), 7.23–7.25 (d, 1H), 7.50–7.55 (s, 1H) ppm. MS: $M^++1=448$ Da.

Example 206

4-(2,6-Dimethoxy-pyridin-4-ylmethyl)-6-(4-oxo-2-thioxo-thiazolidin-5-ylidenemethyl)-4H-benzo[1,4]oxazine-3-one $^1$H NMR (DMSO-$d_6$) δ 3.80 (s, 6H), 4.91 (s, 2H), 5.07 (s, 2H), 6.28 (s, 2H), 6.94 (s, 1H), 7.12–7.14 (d, 1H), 7.22–7.24 (d, 1H), 7.48 (s, 1H) ppm. MS: $M^++1=444$ Da.

Example 207

6-(4-Oxo-2-thioxo-thiazolidin-5-ylidenemethyl)-4-(4-trifluoromethyl-benzyloxy)-4H-benzo[1,4]oxazin-3-one The title compound was synthesized in a manner analogous to Example 88. MP>300° C. MS: $M^+-1=465.0$ Da.

Example 208

4-Cyclohexylmethoxy-6-(4-oxo-2-thioxo-thiazolidin-5-ylidenemethyl)-4H-benzo[1,4]oxazin-3-.one The title compound was synthesized in a manner analogous to Example 88. MP=249–250° C. MS: $M^+-1=403.1$ Da.

Example 209

4-(2,6-Di-tert-butyl-pyridin-4-ylmethoxy)-6-(4-oxo-2-thioxo-thiazolidin-5-ylidenemethyl)-4H-benzo[1,4]oxazin-3-one The title compound was synthesized in a manner analogous to Example 88. MP>300° C. MS: $M^+-1=510.1$ Da.

Example 210

4-(3,5-Diisopropyl-benzyl)-6-(4-oxo-2-thioxo-thiazolidin-5-ylidenemethyl)-4H-benzo[1,4]oxazin-3-one The title compound was synthesized in a manner analogous to Example 38. $^1$H NMR (DMSO-$d_6$) δ 1.13 (d, 12H), 2.81 (m, 1H), 4.91 (s, 2H), 5.12 (s, 2H), 6.97 (s, 3H), 7.14 (d, 1H), 7.25 (d, 1H), 7.50 (s, 1H). MS: M$^+$−1=466.1 Da.

Example 211

4-(3-tert-Butyl-5-methyl-benzyl)-6-(4-oxo-2-thioxo-thiazolidin-5-ylidenemethyl)-4H-1,4-benzoxazin-3-one The title compound was synthesized in a manner analogous to Example 38. Microanalysis: $C_{24}H_{24}N_2O_3S_2$ calculated: C=63.69, H=5;34, N=6.19; found: C=63.69, H=5.34, N=6.09. MS: M$^+$−1=452.1 Da.

Intermediate 74: 4-(3-tert-Butyl-5-hydroxymethyl-benzyl)-3-oxo-3,4-dihydro-2H-1,4-benzoxazine-6-carbaldehyde. The title compound was synthesized in a manner analogous to intermediate 5 using intermediate 36. MS: M$^+$−1=353.3 Da.

Example 212

4-(3-tert-Butyl-5-hydroxymethyl-benzyl)-6-(4-oxo-2-thioxo-thiazolidin-5-ylidenemethyl)-4H-1,4-benzoxazin-3-one The title compound was synthesized in a manner analogous to Example 1 using intermediate 74. $^1$H NMR (DMSO-$d_6$) δ 1.23 (s, 9H), 4.41 (d, 2H), 4.90 (s, 2H), 5.07 (s, 1H), 5.17 (s, 2H), 6.95 (s, 1H), 7.13–7.24 (m, 4H), 7.30 (s, 1H), 7.47 (s, 1H). MS: M$^+$−1=468.1 Da.

Intermediate 75: (6-Formyl-3-oxo-2,3-dihydro-1,4-benzoxazin-4-yl)-acetic acid. The title compound was synthesized in a manner analogous to Example 3 using intermediate 5. MS: M$^+$−1=234.1 Da.

Intermediate 76: 4-[2-(3,5-Dimethyl-piperidin-1-yl)-2-oxo-ethyl]-3-oxo-3,4-dihydro-2H-benzo[1,4]oxazine-6-carbaldehyde. The title compound was synthesized in a manner analogous to intermediate 32 using intermediate 75 and 3,5-dimethyl-piperidine. MS: M$^+$−1=330.1 Da.

Example 213

4-[2-(3,5-Dimethyl-piperidin-1-yl)-2-oxo-ethyl]-6-(4-oxo-2-thioxo-thiazolidin-5-ylidenemethyl)-4H-1,4-benzoxazin-3-one The title compound was synthesized in a manner analogous to Example 1 using intermediate 76. Microanalysis: $C_{21}H_{23}N_3O_4S_2$ calculated: C=56.61, H=5.20, N=9.43; found: C=56.28, H=5.31, N=9.15. MS: M$^+$−1=444.1 Da.

Example 214

4-{2-[3-Oxo-6-(4-oxo-2-thioxo-thiazolidin-5-ylidenemethyl)-2,3-dihydro-1,4-benzoxazin-4-yl]-acetyl}-piperazine-1-carboxylic acid tert-butyl ester The title compound was synthesized in a manner analogous to Example 213. $^1$H NMR (DMSO-$d_6$) δ 1.41 (s, 9H), 3.37 (bs, 2H), 3.48–3.49 (m, 4H), 3.60 (bs, 2H), 4.80 (s, 2H), 4.91 (s, 2H), 6.98 (d, 1H), 7.15 (d, 1H), 7.29–7.32 (q, 1H), 7.58 (s, 1H), 13.79 (bs, 1H). MS: M$^+$−1=517.1 Da.

Example 215

4-(2-Oxo-2-piperazin-1-yl-ethyl)-6-(4-oxo-2-thioxo-thiazolidin-5-ylidenemethyl)-4H-1,4-benzoxazin-3-one The title compound was synthesized in a manner analogous to Example 213. $^1$H NMR (DMSO-$d_6$) δ 3.15 (bs, 2H), 3.26 (bs, 2H), 3.67 (bs, 2H), 3.81 (bs, 2H), 4.80 (s, 2H), 4.94 (s, 2H), 7.12 (s, 1H), 7.16 (d, 1H), 7.24 (d, 1H), 7.58 (s, 1H). MS: M$^+$−1=417.1 Da.

Intermediate 77: 3-tert-Butyl-5-(6-formyl-3-oxo-2,3-dihydro-benzo[1,4]oxazin-4-ylmethyl)-benzamide. The title compound was synthesized in a manner analogous to intermediate 32 using intermediate 31 and ammonium hydroxide. MS: M$^+$−1=366.2 Da.

Example 216

3-tert-Butyl-5-[3-oxo-6-(4-oxo-2-thioxo-thiazolidin-5-ylidenemethyl)-2,3-dihydro-1,4-benzoxazin-4-ylmethyl]-benzamide The title compound was synthesized in a manner analogous to Example 1 using intermediate 77. $^1$H NMR (DMSO-$d_6$) δ 1.26 (s, 9H), 4.90 (s, 2H), 5.20 (s, 2H), 7.14 (d, 2H), 7.21 (d, 1H), 7.29 (s, 1H), 7.43 (d, 2H), 7.59 (s, 1H), 7.76 (s, 1H), 7.93 (s, 1H). MS: M$^+$−1=481.2 Da.

Example 217

4-(3,5-Dibromo-benzyl)-6-(4-oxo-2-thioxo-thiazolidin-5-ylidenemethyl)-4H-1,4-benzoxazin-3-one The title compound was synthesized in a manner analogous to Example 38. Microanalysis: $C_{19}H_{12}Br_2N_2O_3S_2$ calculated: C=42.24, H=2.24, N=5.19; found: C=42.20, H=2.48, N=5.32. MS: M$^+$−1=538.9 Da.

Example 218

4-[1-(3,5-Dimethyl-phenyl)-ethyl]-6-(4-oxo-2-thioxo-thiazolidin-5-ylidenemethyl)-4H-1,4-benzoxazin-3-one The title compound was synthesized in a manner analogous to Example 38. $^1$H NMR (DMSO-$d_6$) δ 1.71 (d, 3H), 2.27 (s, 6H), 4.81–4.95 (dd, 2H), 6.24 (q, 1H), 6.74 (d, 1H), 6.90 (s, 1H), 6.97 (s, 2H), 7.15 (d, 1H), 7.29–7.32 (dd, 1H), 7.41 (s, 1H), 13.62 (bs, 1H). MS: M$^+$−1=423.1 Da.

Example 219

5-[4-(3,5-Di-tert-butyl-4-hydroxy-benzyl)-3-oxo-3,4-dihydro-2H-1,4-benzoxazin-6-ylmethylene]-thiazolidine-2,4-dione The title compound was synthesized in a manner analogous to Example 66. Microanalysis: $C_{27}H_{30}N_2O_5S_1$ calculated: C=65.57, H=6.11, N=5.66; found: C=65.28, H=6.13, N=5.51. MS: M$^+$−1=493.3 Da.

Example 220

4-(2,6-Di-tert-butyl-pyridin-4-ylmethyl)-8-fluoro-6-(4-oxo-2-thioxo-thiazolidin-5-ylidenemethyl)-4H-1,4-benzoxazin-3-one The title compound was synthesized in a manner analogous to Example 46. $^1$H NMR (DMSO-d$_6$) δ 1.26 (s, 18H), 5.04 (s, 2H), 5.18 (s, 2H), 6.86 (s, 1H), 7.07 (s, 2H), 7.32 (d, 1H), 7.50 (s, 1H). MS: M$^+$−1=513.2 Da.

Example 221

4-(2,6-Di-tert-butyl-pyridin-4-ylmethyl)-8-methyl-6-(4-oxo-2-thioxo-thiazolidin-5-ylidenemethyl)-4H-1,4-benzoxazin-3-one The title compound was synthesized in a manner analogous to Example 35 using BEMP resin as in intermediate 22. $^1$H NMR (DMSO-d$_6$) δ 1.25 (s, 8H), 2.24 (s, 3H), 4.95 (s, 2H), 5.15 (s, 2H), 6.92 (s, 1H), 7.07 (s, 2H), 7.17 (s, 1H), 7.47 (s, 1H). MS: M$^+$−1=509.2 Da.

Example 222

4-[3-tert-Butyl-5-(4-methyl-piperazin-1-ylmethyl)-benzyl]-6-(4-oxo-2-thioxo-thiazolidin-5-ylidenemethyl)-4H-1,4-benzoxazin-3-one The title compound was synthesized in a manner analogous to Example 19. $^1$H NMR (DMF-d$_7$) δ 1.24 (s, 9H), 2.69 (s, 3H), 2.71–2.76 (bs, 4H), 2.81–2.93 (bs, 4H), 3.63 (s, 2H), 4.93 (s, H), 5.30 (s, 2H), 7.11–7.21 (m, 3H), 7.24 (s, 1H), 7.29 (s, 1H), 7.37 (s, 1H). MS: M$^+$−1=550.2 Da.

Intermediate 78: 4-(4-Bromomethyl-benzyl)-2-methyl-3-oxo-3,4-dihydro-2H-benzo[1,4]oxazine-6-carbaldehyde. The title compound was synthesized in a manner analogous to intermediate 16 using intermediate 10 and α,α'-dibromo-p-xylene. MS: M$^+$−1=374.0 Da.

Intermediate 79: 2-Methyl-4[4-(4-methyl-piperazin-1-ylmethyl)-benzyl]-3-oxo-3,4-dihydro-2H-benzo[1,4]oxazine-6-carbaldehyde. The title compound was synthesized in a manner analogous to intermediate 17 using intermediate 78 and 1-methylpiperazine. MS: M$^+$−1=393.2 Da.

Example 223

2-Methyl-4-[4-(4-methyl-piperazin-1-ylmethyl)-benzyl]-6-(4-oxo-2-thioxo-thiazolidin-5-ylidenemethyl)-4H-1,4-benzoxazin-3-one The title compound was synthesized in a manner analogous to Example 1 using intermediate 79. $^1$H NMR (DMF-d$_7$) δ 1.59 (d, 3H), 2.71–2.76 (bs, 4H), 2.90–3.02 (bs, 4H), 3.57 (s, 2H), 4.99–5.04 (dd, 1H), 5.20–5.37 (dd, 2H), 7.15–7.24 (m, 2H), 7.32–7.38 (m, 2H). MS: M$^+$−1=508.1 Da.

Example 224

5-[4-(2,6-Di-tert-butyl-pyridin-4-ylmethyl)-8-methyl-3-oxo-3,4-dihydro-2H-1,4-benzoxazin-6-ylmethylene]-thiazolidine-2,4-dione The title compound was synthesized in a manner analogous to Example 35 using thiazoladinedione instead of rhodanine. $^1$H NMR (DMSO-d$_6$) δ 1.24 (s, 18H), 2.23 (s, 3H), 4.94 (s, 2H), 5.14 (s, 2H), 6.90 (s, 1H), 7.06 (s, 2H), 7.17 (s, 1H), 7.60 (s, 1H). MS: M$^+$−1=492.2 Da.

Example 225

4-(2,6-Dichloro-pyridin-4-ylmethyl)-6-(4-oxo-2-thioxo-thiazolidin-5-ylidenemethyl)-4H-1,4-benzoxazin-3-one The title compound was synthesized in a manner analogous to Example 38. $^1$H NMR (DMSO-d$_6$) δ 4.96 (s, 2H), 5.20 (s, 2H), 7.02 (s, 1H), 7.17–7.26 (dd, 2H), 7.51 (s, 1H), 7.57 (s, 2H). MS: M$^+$−1=450.9 Da.

Example 226

5-[4-(2,6-Dichloro-pyridin-4-ylmethyl)-3-oxo-3,4-dihydro-2H-1,4-benzoxazin-6-ylmethylene]-thiazolidine-2,4-dione The title compound was synthesized in a manner analogous to Example 66. $^1$H NMR (DMSO-d$_6$) δ 4.89 (s, 2H), 5.18 (s, 2H), 7.05 (d, 1H), 7.15 (s, 1H), 7.29 (d, 1H), 7.50 (s, 2H), 8.09 (s, 1H). MS: M$^+$−1=434.1 Da.

Example 227

5-(3-Oxo-4-pyridin-4-ylmethyl-3,4-dihydro-2H-1,4-benzoxazin-6-ylmethylene)-thiazolidine-2,4-dione The title compound was synthesized in a manner analogous to Example 66. $^1$H NMR (DMSO-d$_6$) δ 4.89 (s, 2H), 5.16 (s, 2H), 7.01 (s, 1H), 7.13 (d, 1H), 7.19–7.21 (dd, 1H), 7.28 (d, 2H), 7.60 (s, 1H), 8.46 (d, 2H). MS: M$^+$−1=366.0 Da.

Example 228

5-{4-[4-(4-Methyl-piperazin-1-ylmethyl)-benzyl]-3-oxo-3,4-dihydro-2H-1,4-benzoxazin-6-ylmethylene}-thiazolidine-2,4-dione The title compound was synthesized in a manner analogous to Example 66, using BEMP resin and intermediate 3 to provide 4-[4-(4-methyl-piperazine-1-ylmethyl)-benzyl]-3-oxo-3,4-dihydro-2H-1,4-benzoxazine-6-carbaldehyde. 4-[4-(4-Methyl-piperazine-1-ylmethyl)-benzyl]-3-oxo-3,4-dihydro-2H-1,4-benzoxazine-6-carbaldehyde was then reacted with 1-methylpiperazine in a manner analogous to intermediate 17 to provide 4-[4-(4-methyl-piperazine-1-ylmethyl)-benzyl]-3-oxo-3,4-dihydro-2H-1,4-benzoxazine-6-carbaldehyde which was then reacted thiazoladinedione in an analogous manner to Example 66. $^1$H NMR (DMSO-d$_6$) δ 2.35 (s, 3H), 2.63–2.81 (bs, 4H), 3.13–3.30 (bs, 4H), 3.43 (s, 2H), 4.83 (s, 2H), 5.12 (s, 2H), 7.05–7.15 (m, 3H), 7.23–7.29 (m, 5H). MS: M$^+$−1=477.1 Da.

Example 229

4-(2,6-Dimethyl-pyridin-4-ylmethyl)-6-(4-oxo-2-thioxo-thiazolidin-5-ylidenemethyl)-4H-1,4-benzoxazin-3-one The title compound was synthesized in a manner analogous to Example 38. $^1$H NMR (DMSO-d$_6$) δ 2.46 (s, 6H), 4.92 (s, 2H), 5.10 (s, 2H), 6.89 (s, 1H), 6.99 (s, 2H), 7.14 (d, 1H), 7.25 (d, 1H), 7.41 (s, 1H). MS: M$^+$−1=410.0 Da.

Example 230

5-[4-(2,6-Dimethyl-pyridin-4-ylmethyl)-3-oxo-3,4-dihydro-2H-1,4-benzoxazin-6-ylmethylene]-thiazolidine-2,4-dione The title compound was synthesized in a manner analogous to Example 66. Microanalysis: $C_{20}H_{17}N_3O_4S_1$ calculated: C=60.75, H=4.33, N=10.63; found: C=60.66, H=4.59, N=10.82. MS: $M^+ +1=394.1$ Da.

Example 231

5-Methoxy-2-[3-oxo-6-(4-oxo-2-thioxo-thiazolidin-5-ylidenemethyl)-2,3-dihydro-1,4-benzoxazin-4-ylmethyl]-pyrimidine-4-carboxylic acid methyl ester The title compound was synthesized in a manner analogous to Example 38. $^1$H NMR (DMSO-$d_6$) δ 3.82 (s, 3H), 3.88 (s, 3H), 4.81 (s, 2H), 5.23 (s, 2H), 7.12–7.20 (m, 3H), 7.45 (s, 1H), 8.75 (s, 1H). MS: $M^+ -1=471.0$ Da.

Example 232

4-(4,6-Dimethyl-pyrimidine-2-ylmethyl)-6-(4-oxo-2-thioxo-thiazolidin-5-ylidenemethyl)-4H-benzo[1,4]oxazin-3-one The title compound was synthesized in a manner analogous to Example 38. $^1$H NMR (DMSO-$d_6$) δ 2.37 (s, 3H), 4.85 (s, 2H), 5.24 (s, 2H), 6.95 (s, 1H), 7.15–7.16 (m, 2H), 7.28 (d, 1H), 7.47 (s, 1H). MS: $M^+ -1=412.0$ Da.

Example 233

4-(4-Chloro-3-trifluoromethyl-benzyl)-8-fluoro-6-(4-oxo-2-thioxo-thiazolidin-5-ylidenemethyl)-4H-1,4-benzoxazin-3-one The title compound was synthesized in a manner analogous to Example 38 using intermediate 24 instead of intermediate 3. Microanalysis: $C_{20}H_{11}Cl_1N_2O_3S_2$ calculated: C=47.77, H=2.20, N=5.57; found: C=47.67, H=2.07, N=5.54. MS: $M^+ -1=501.9$ Da.

Example 234

4-(4,6-Di-tert-butyl-pyrimidin-2-ylmethyl)-6-(4-oxo-2-thioxo-thiazolidin-5-ylmethyl)-4H-benzo[1,4]oxazin-3-one The title compound was synthesized in a manner analogous to Example 38. Microanalysis: $C_{25}H_{28}N_4O_3S_2$ calculated: C=60.46, H=5.68, N=11.28; found: C=58.45, H=5.47, N=10.80. MS: $M^+ -1=496.1$ Da.

Example 235

4-(4,6-Di-tert-butyl-pyrimidin-2-ylmethyl)-8-fluoro-6-(4-oxo-2-thioxo-thiazolidin-5-ylmethyl)-4H-benzo[1,4]oxazin-3-one The title compound was synthesized in a manner analogous to Example 38 using intermediate 24. Microanalysis: $C_{25}H_{27}N_4O_3S_2F_1$ calculated: C=58.35, H=5.29, N=10.89; found: C=58.31, H=4.88, N=10.79. MS: $M^+ -1=514.1$ Da.

Example 236

4-[3-tert-Butyl-5-(1-hydroxy-1-methyl-ethyl)-benzyl]-8-fluoro-6-(4-oxo-2-thioxo-thazolidin-5-ylmethyl)-4H-benzo[1,4]oxazin-3-one The title compound was synthesized in a manner analogous to Example 38 using intermediate 24. Microanalysis: $C_{26}H_{27}N_2O_4S_2F_1$ calculated: C=60.68, H=5.29, N=5.44; found: C=60.72, H=5.31, N=5.42. MS: $M^+ -1=514.1$ Da.

Example 237

4-[3-tert-Butyl-5-(1-hydroxy-1-methyl-ethyl)-benzyl]-6-(4-oxo-2-thioxo-thazolidin-5-ylmethyl)-4H-benzo[1,4]oxazin-3-one The title compound was synthesized in a manner analogous to Example 38. $^1$H NMR (DMSO-$d_6$) δ 1.22 (s, 9H), 1.33 (s, 6H), 4.89 (m, 3H), 5.16 (s, 2H), 7.14–7.24 (m, 5H), 7.36 (s, 1H), 7.51 (s, 1H. MS: $M^+ -1=495.1$ Da.

Example 238

4-[4-(3-Aza-spiro[5.5]undec-3-ylmethyl)-benzyl]-6-(4-oxo-2-thioxo-thiazolidin-5-ylidenemethyl)-4H-benzo[1,4]oxazin-3-one The title compound was synthesized in a manner analogous to Example 19. $^1$H NMR (DMSO-$d_6$) δ 1.15–1.60 (m, 12H), 3.31 (bs, 4H), 4.19 (bs, 2H), 4.89 (s, 2H), 5.21 (s, 2H), 6.96–7.16 (m, 4H), 7.40–7.45 (m, 4H). MS: $M^+ +1=548.2$ Da.

Example 239

5-{4-[4-(3-Aza-spiro[5.5]undec-3-ylmethyl)-benzyl]-3-oxo-3,4-dihydro-2H-benzo[1,4]oxazin-6-ylmethylene}-thiazolidine-2,4-dione The title compound was synthesized in a manner analogous to Example 19 using thiazolidenedione instead of rhodanine. $^1$H NMR (DMSO-$d_6$) δ 1.25–1.45 (m, 12H), 2.70 (bs, 4H), 3.89 (bs, 2H), 4.88 (s, 2H), 5.18 (s, 2H), 7.07–7.19 (m, 4H), 7.34–7.37 (m, 4H). MS: $M^+ +1=532.3$ Da.

Example 240

4-{4-[6-(2,4-Dioxo-thiazolidin-5-ylidenemethyl)-3-oxo-2,3-dihydro-1,4-benzoxazin-4-ylmethyl]-benzyl}-piperazine-1-carboxylic acid ethyl ester The title compound was synthesized in a manner analogous to Example 239. $^1$H NMR (DMSO-$d_6$) δ 1.15 (t, 3H), 2.32 (bs, 4H), 3.47 (s, 2H), 4.01 (q, 2H), 4.91 (s, 2H), 5.16 (s, 2H), 7.11–7.16 (m, 2H), 7.23–7.7 (m, 4H), 7.63 (s, 1H). MS: $M^+ +1=537.2$ Da.

Example 241

4-{4-[3-Oxo-6-(4-oxo-2-thioxo-thiazolidin-5-ylidenemethyl)-2,3-dihydro-benzo[1,4]oxazin-4-ylmethyl]-benzyl}-piperazine-1-carboxylic acid ethyl ester The title compound was synthesized in a manner analogous to Example 19. $^1$H NMR (DMSO-$d_6$) δ 1.12 (t, 3H), 2.45 (bs, 4H), 3.31 (bs, 4H), 3.61 (s, 2H), 4.01 (q, 2H), 4.91

(s, 2H), 5.18 (s, 2H), 7.07 (s, 1H), 7.14 (d, 1H), 7.24 (d, 1H),7.30 (s, 4H), 7.41 (s, 1H). MS: M$^+$+1=553.2 Da.

Intermediate 80: 4-(3-Chloro-propyl)-8-fluoro-3-oxo-3,4-dihydro-2H-benzo[1,4]oxazine-6-carbaldehyde. The title compound was synthesized in a manner analogous to intermediate 16 using intermediate 3 and 3-bromo-1-chloropropane.

Intermediate 81: 8-Fluoro-4-(3-morpholin-4-yl-propyl)-3-oxo-3,4-dihydro-2H-benzo[1,4]oxazine-6-carbaldehyde. The title compound was synthesized in a manner analogous to intermediate 17 using intermediate 80 and morpholine.

Example 242

8-Fluoro-4-(3-morpholin-4-yl-propyl)-6-(4-oxo-2-thioxo-thiazolidin-5-ylidenemethyl)-4H-benzo[1,4]oxazin-3-one The title compound was synthesized in a manner analogous to Example 1 using intermediate 81. $^1$H NMR (DMSO-d$_6$) δ 1.90 (quint, 2H), 2.81 (bs, 4H), 3.66 (bs, 4H), 4.00 (t, 2H), 4.81 (s, 2H), 7.11 (d, 1H), 7.22 (d, 1H),7.37 (s, 1H), 7.41 (s, 1H). MS: M$^+$+1=430.0 Da.

Example 243

8-Fluoro-6-(4-oxo-2-thioxo-thiazolidin-5-ylidenemethyl-4-(3-piperidin-1-yl-propyl)-4H-benzo[1,4]oxazin-3-one The title compound was synthesized in a manner analogous to Example 242. $^1$H NMR (DMSO-d$_6$) δ 1.40–1.78 (m, 6H), 2.02 (m, 2H), 3.08 (bm, 4H), 3.98 (t, 2H), 4.81 (s, 2H), 7.03 (d, 1H), 7.18 (s, 2H). MS: M$^+$+1=436.1 Da.

Example 244

4-[3-(3,5-Dimethyl-piperidin-1-yl)-propyl]-8-fluoro-6-(4-oxo-2-thioxo-thiazolidin-5-ylidenemethyl)-4H-benzo[1,4]oxazin-3-one The title compound was synthesized in a manner analogous to Example 242. $^1$H NMR (DMSO-d$_6$) δ 0.75 (4, 1H), 0.86 (d, 6H), 0.93–0.95 (bm, 1H), 1.68–1.79 (m, 2H), 2.01–2.03 (m, 2H), 2.47–2.50 (m, 2H), 2.98–3.10 (m, 2H), 3.29–3.35 (m, 3H), 3.97–4.00 (m, 2H), 4.81 (s, 1H), 6.97–7.02 (m, 1H), 7.14–7.15 (m, 2H). MS: M$^+$+1=464.1 Da.

Example 245

4-(3-Diisopropylamino-propyl)-8-fluoro-6-(4-oxo-2-thioxo-thiazolidin-5-ylidenemethyl)-4H-benzo[1,4]oxazin-3-one The title compound was synthesized in a manner analogous to Example 242. $^1$H NMR (DMF-d$_4$) δ 1.34 (d, 6H), 2.19–2.40 (m, 2H), 3.34–3.40 (m, 2H), 3.65–3.81 (m, 2H), 4.13 (t, 3H), 4.59 (s, 2H), 7.12 (d, 1H), 7.24 (s, 2H). MS: M$^+$+1=452.1 Da.

Example 246

5-[4-(3,4-Dichloro-benzyl)-3-oxo-3,4-dihydro-2H-benzo[1,4]oxazin-6-ylmethylene]-thiazolidine-2,4-dione The title compound was synthesized in a manner analogous to Example 2, with the substitution of thiazoladinedione for rhodanine. $^1$H NMR (DMSO-d$_6$) δ 12.50 (s, 1H), 7.67 (s, 1H), 7.65 (s, 1H), 7.61 (d, 1H), 7.29 (d, 1H), 7.24 (d, 1H), 7.16 (d, 1H), 7.10 (s, 1H), 5.16 (s, 2H), 4.91 (s, 2H). MS: M$^+$−1=434.9 Da.

Example 247

4-(3,5-Di-tert-butyl-benzyl)-6-(4-oxo-2-thioxo-oxazolidin-5-ylidenemethyl)-4H-1,4-benzoxazin-3-one The title compound was synthesized in a manner analogous to Example 84. $^1$H NMR (CDCl$_3$/CD$_3$OD 3 drop) δ 7.44 (d, 2H), 7.22 (2, 2H), 7.07 (s, 2H), 7.06 (d, 11H), 6.42 (s, 1H), 5.17 (s, 2H), 1.20 (s, 9H). MS: M$^+$−1=479.20 Da.

Example 248

Acetic acid 4-[3-oxo-6-(4-oxo-2-thioxo-thiazolidin-5-ylidenemethyl)-2,3-dihydro-1,4-benzoxazin-4-ylmethyl]-phenyl ester Microanalysis: C$_{21}$H$_{16}$N$_2$O$_5$S$_2$; calculated: C=57.26, H=3.66, N=6.36; found: C=57.35, H=3.75, N=6.49. MS: M$^+$+1=441.1 Da.

Example 249

5-[4-(4-Benzyloxy-benzyl)-3-oxo-3,4-dihydro-2H-1,4-benzoxazin-6-ylmethylene]-thiazolidine-2,4-dione The title compound was synthesized in a manner analogous to Example 246. Microanalysis: C$_{26}$H$_{20}$N$_2$O$_5$S; calculated: C=66.09, H=4.27, N=5.39; found: C=66.10, H=4.18, N=5.75. MS: M$^+$−1=471.2 Da.

Example 250

4-(3,5-Di-tert-butyl-cyclohexylmethyl)-6-(4-oxo-2-thioxo-thiazolidin-5-ylidenemethyl)-4H-1,4-benzoxazin-3-one The title compound was synthesized in an analogous manner to Example 2 using intermediate 3 and 3,5-Di-t-butyl-1-(bromomethyl)cyclohexane. Microanalysis: C$_{27}$H$_{36}$N$_2$O$_3$S$_2$.0.14H$_2$O; calculated: C=64.44, H=7.27, N=5.57, KF(H$_2$O)=0.49; found: C=64.56, H=7.22, N=5.69, KF(H$_2$O)=0.51. MS: M$^+$+1=384.2 Da.

Example 251

5-{4-[3-Methyl-5-(4-methyl-piperazin-1-ylmethyl)-benzyl]-3-oxo-3,4-dihydro-2H-1,4-benzoxazin-6-ylmethylene}-thiazolidine-2,4-dione.

The title compound was synthesized in an analogous manner to Example 19 using 2,4-thiazolidinedione in place of rhodanine. Microanalysis: C$_{26}$H$_{28}$N$_4$O$_4$S.0.7H$_2$O; calculated: C=61.81, H=5.87, N=11.09; found: C=61.67, H=5.63, N=10.90. MS: M$^+$+1=493.2 Da.

Example 252

5-{3-Oxo-4-[3-(propane-2-sulfonyl)-benzyl]-3,4-dihydro-2H-1,4-benzoxazin-6-ylmethylene}-thiazolidine-2,4-dione The title compound was synthesized in a manner analogous to Example 2 using thiazoladinedione instead of rhodanine. Microanalysis: $C_{22}H_{20}N_2O_6S_2$; calculated: C=55.92, H=4.27, N=5.93; found: C=55.89, H=4.16, N=5.76. MS: $M^++1=473.1$ Da.

Example 253

6-(4-Oxo-2-thioxo-thiazolidin-5-ylidenemethyl)-4-[3-(propane-2-sulfonyl)-benzyl]-4H-1,4-benzoxazin-3-one Microanalysis: $C_{22}H_{20}N_2O_5S_3$; calculated: C=54.08, H=4.13, N=5.73; found: C=54.07, H=3.95, N=5.58. MS: $M^++1=489.1$ Da.

Example 254

4-(3-Isopropylsulfanyl-benzyl)-6-(4-oxo-2-thioxo-thiazolidin-5-ylidenemethyl)-4H-1,4-benzoxazin-3-one Microanalysis: $C_{22}H_{20}N_2O_3S_3$; calculated: C=57.87, H=4.42, N=6.14; found: C=57.61, H=4.07, N=5.91. MS: $M^++1=457.1$ Da.

Example 255

4-[3-Methyl-5-(4-methyl-piperazin-1-ylmethyl)-benzyl]-6-(4-oxo-2-thioxo-thiazolidin-5-ylidenemethyl)-4H-1,4-benzoxazin-3-one.

Microanalysis: $C_{26}H_{28}N_4O_3S_2.0.2H_2O$; calculated: C=60.96, H=5.59, N=10.94, $KF(H_2O)$=0.70; found: C=60.78, H=5.55, N=10.97, $KF(H_2O)$=0.56. MS: $M^++1=493.2$ Da.

Example 256

3-[6-(2,4-Dioxo-thiazolidin-5-ylidenemethyl)-3-oxo-2,3-dihydro-1,4-benzoxazin-4-ylmethyl]-N,N-dimethyl-benzenesulfonamide The title compound was synthesized in a manner analogous to Example 252. Microanalysis: $C_{21}H_{19}N_3O_6S_2$; calculated: C=53.27, H=4.04, N=8.87; found: C=52.86, H=3.71, N=8.80. MS: $M^++1=474.1$ Da.

Example 257

4-[3-(Morpholine-4-sulfonyl)-benzyl]-6-(4-oxo-2-thioxo-thiazolidin-5-ylidenemethyl)-4H-1,4-benzoxazin-3-one Microanalysis: $C_{23}H_{21}N_3O_6S_3$; calculated: C=51.96, H=3.98, N=7.90; found: C=51.98, H=3.70, N=7.90. MS: $M^++1=532.0$ Da.

Example 258

5-(4-Cyclohexylmethyl-3-oxo-3,4-dihydro-2H-1,4-benzoxazin-6-ylmethylene)-thiazolidine-2,4-dione The title compound was synthesized in a manner analogous to Example 252. Microanalysis: $C_{19}H_{20}N_2O_4S.0.17H_2O$; calculated: C=60.77, H=5.46, N=7.46; found: C=60.40, H=5.30, N=7.34. MS: $M^+-1=371.1$ Da.

Example 259

4-[4-(Morpholine-4-sulfonyl)-benzyl]-6-(4-oxo-2-thioxo-thiazolidin-5-ylidenemethyl)-4H-1,4-benzoxazin-3-one Microanalysis: $C_{23}H_{21}N_3O_6S_3$; calculated: C=51.96, H=3.98, N=7.90; found: C=51.76, H=3.98, N=7.90. MS: $M^+-1=531.0$ Da.

Example 260

4-(3-Isopropyl-2-methoxy-benzyl)-6-(4-oxo-2-thioxo-thiazolidin-5-ylidenemethyl)-4H-1,4-benzoxazin-3-one Microanalysis: $C_{23}H_{22}N_2O_4S_2.0.5H_2O$; calculated: C=59.59, H=5.00, N=6.04; found: C=59.61, H=5.16, N=5.84. MS: $M^++1=455.0$ Da.

Example 261

4-Cyclohexylmethyl-6-(4-oxo-2-thioxo-oxazolidin-5-ylidenemethyl)-4H-1,4-benzoxazin-3-one The title product was synthesized in a manner analogous to Example 84. Microanalysis: $C_{19}H_{20}N_2O_4S.0.2H_2O$; calculated: C=60.68, H=5.42, N=7.45; found: C=60.62, H=5.27, N=7.37.84. MS: $M^++1=373.1$ Da.

Example 262

N,N-Dimethyl-3-[3-oxo-6-(4-oxo-2-thioxo-thiazolidin-5-ylidenemethyl)-2,3-dihydro-1,4-benzoxazin-4-ylmethyl]-benzenesulfonamide.

Microanalysis: $C_{21}H_{19}N_3O_5S_3.0.05H_2O$; calculated: C=51.42, H=3.92, N=8.57, $KF(H_2O)$=0.18; found: C=51.30, H=3.66, N=8.71, $KF(H_2O)$=0.20. MS: $M^++1=490.1$ Da.

Example 263

4-(3-tert-Butyl-benzyl)-6-(4-oxo-2-thioxo-thiazolidin-5-ylidenemethyl)-4H-1,4-benzoxazin-3-one Microanalysis: $C_{23}H_{22}N_2O_3S_2.0.1H_2O$; calculated: C=62.73, H=5.08, N=6.36, $KF(H_2O)$=0.40; found: C=62.44, H=4.97, N=6.48, $KF(H_2O)$=0.10. MS: $M^++1=439.0$ Da.

Example 264

N,N-Dimethyl-4-{3-oxo-6-[4-oxo-2-thioxo-thiazolidin-(5Z)-ylidenemethyl]-2,3-dihydro-benzo[1,4]oxazin-4-ylmethyl}-benzenesulfonamide Microanalysis: $C_{21}H_{19}N_3O_5S_2.0.1H_2O$; calculated: C=51.33, H=3.94, N=8.55, KF($H_2O$)=0.37; found: C=50.98, H=3.93, N=8.39, KF($H_2O$)=0.39. MS: $M^++1$=490.0 Da.

Example 265

5-[1-[4-(3-Methanesulfonyl-benzyl)-3-oxo-3,4-dihydro-2H-benzo[1,4]oxazin-6-yl]-meth-(Z)-ylidene]-thiazolidine-2,4-dione The title compound was synthesized in a manner analogous to Example 252. Microanalysis: $C_{20}H_{16}N_2O_6S_2.0.05H_2O$; calculated: C=53.93, H=3.64, N=6.29, KF($H_2O$)=0.20; found: C=53.97, H=3.54, N=6.29, KF($H_2O$)=0.17. MS: $M^++1$=445.0 Da.

Example 266

4-Benzyl-6-{1-[4-oxo-2-thioxo-thiazolidin-(5Z)-ylidene]-ethyl}-4H-benzo[1,4]oxazin-3-one The title compound was synthesized in a manner analogous to Example 2 using 6-acetyl-4H-benzo[1,4]oxazin-3-one instead of intermediate 3. Microanalysis: $C_{20}H_{16}N_2O_3S_2$; calculated: C=60.59, H=4.07, N=7.07; found: C=60.30, H=3.90, N=6.97. MS: $M^++1$=397.0 Da.

Example 267

7-[4-Oxo-2-thioxo-thiazolidin-(5Z)-ylidenemethyl]-1-phenethyl-1H-pyrido[2,3-b][1,4]oxazin-2-one The title compound was synthesized in a manner analogous to Example 190. Microanalysis: $C_{19}H_{15}N_3O_3S_2$; calculated: C=57.42, H=3.80, N=10.57, S=16.13; found: C=57.35, H=3.74, N=10.41, S=15.77. MS: $M^++1$=397.0 Da.

Example 268

6-{1-[4-Oxo-2-thioxo-thiazolidin-(5Z)-ylidene]-ethyl}-4H-benzo[1,4]oxazin-3-one

The title compound was synthesized in a manner analogous to Example 266. Microanalysis: $C_{13}H_{10}N_2O_3S_2.0.1H_2O$; calculated: C=50.66, H=3.34, N=9.09, KF($H_2O$)=0.58; found: C=50.31, H=3.17, N=9.24, KF($H_2O$)=0.49. MS: $M^++1$=306.9 Da.

Example 269

8-Fluoro-4-(3-methanesulfonyl-benzyl)-6-(4-oxo-2-thioxo-thiazolidin-5-ylidenemethyl)-4H-benzo[1,4]oxazin-3-one The title compound was synthesized in a manner analogous to Example 2 using intermediate 24. Microanalysis: $C_{20}H_{15}FN_2O_5S_3$; calculated: C=50.20, H=3.16, N=5.85; found: C=50.19, H=3.29, N=5.72. MS: $M^+-1$=477.9 Da.

Example 270

4-(3-Methanesulfonyl-benzyl)-6-[4-oxo-2-thioxo-thiazolidin-(5Z)-ylidenemethyl]-4H-benzo[1,4]oxazin-3-one Microanalysis: $C_{20}H_{16}N_2O_5S_3$; calculated: C=52.16, H=3.50, N=6.08; found: C=52.07, H=3.44, N=6.02. MS: $M^+-1$=461.0 Da.

Example 271

4-(3,5-Bis-trifluoromethyl-benzyl)-6-[4-oxo-2-thioxo-oxazolidin-(5Z)-ylidenemethyl]-4H-benzo[1,4]oxazin-3-one The title compound was synthesized in a manner analogous to Example 84. $^1$H NMR (DMSO-$d_6$) δ 4.94 (s, 2H), 5.29 (s, 2H), 6.68 (s, 1H), 7.18 (d, 1H), 7.51 (s, 1H), 7.55 (d, 1H), 7.99 (s, 3H). MS: $M^++1$=503.0 Da.

Example 272

5-[1-[4-(3,5-Bis-trifluoromethyl-benzyl)-3-oxo-3,4-dihydro-2H-benzo[1,4]oxazin-6-yl]-meth-(Z)-ylidene]-thiazolidine-2,4-dione The title compound was synthesized in a manner analogous to Example 2, using ammonium acetate and 2,4-thiazolidinedione instead of rhodanine and EDDA. Microanalysis ($C_{21}H_{12}F_6N_2O_4S$): calculated: C=50.21, H=2.41, N=5.58; found: C=50.51, H=2.24, N=5.38. MS: $M^+-1$=501.1 Da.

Example 273

4-(3,5-Bis-trifluoromethyl-benzyl)-8-fluoro-6-[4-oxo-2-thioxo-thiazolidin-(5Z)-ylidenemethyl]-4H-benzo[1,4]oxazin-3-one The title compound was synthesized in a manner analogous to Example 46. Microanalysis ($C_{21}H_{11}N_2F_7O_3S_2$): calculated: C=47.02, H=2.07, N=5.22; found: C=46.88, H=1.83, N=5.29. MS: $M^+-1$=535.1 Da.

Example 274

4-[3-tert-Butyl-5-(2-methoxy-ethoxymethoxymethyl)-benzyl]-6-[4-oxo-2-thioxo-thiazolidin-(5Z)-ylidenemethyl]-4H-benzo[1,4]oxazin-3-one.

Microanalysis ($C_{28}H_{32}N_2O_6S_2$): calculated: C=60.41, H=5.79, N=5.03; found: C=60.22, H=5.69, N=4.85. MS: $M^+-1$=556.2 Da.

Example 275

4-[3-tert-Butyl-5-(morpholine-4-carbonyl)-benzyl]-6-(4-oxo-2-thioxo-thiazolidin-5-ylidenemethyl)-4H-1,4-benzoxazin-3-one; compound with ethane-1,2-diamine The title compound was synthesized in a manner analogous to Example 59. Microanalysis ($C_{29}H_{32}N_4O_4S_2.0.25$ $C_2H_8N_2$): calculated: C=60.40, H=5.51, N=8.65; found: C=58.8, H=5.50, N=9.03. MS: $M^+-1$=550.2 Da.

Example 276

5-[1-{4-[3-tert-Butyl-5-(1-hydroxy-1-methyl-ethyl)-benzyl]-8-fluoro-3-oxo-3,4-dihydro-2H-benzo[1,4]oxazin-6-yl}-meth-(Z)-ylidene]-thiazolidine-2,4-dione The title compound was synthesized in a manner analogous to Example 272 using intermediate 24. $^1$H NMR (DMSO-d$_6$) δ 1.28 (s, 9H), 1.32 (s, 6H), 4.88–4.89 (m, 1H), 4.98 (s, 2H), 5.15 (s, 2H), 7.00–7.36 (m, 5H), 7.61 (s, 1H). MS: M$^+$−1=497.1 Da.

Example 277

5-[1-[4-(3-tert-Butyl-5-morpholin-4-ylmethyl-benzyl)-3-oxo-3,4-dihydro-2H-benzo[1,4]oxazin-6-yl]-meth-(Z)-ylidene]-thiazolidine-2,4-dione.

The title compound was synthesized in a manner analogous to Example 19, using 1,3-bis-bromomethyl-5-tert-benzene and morpholine, and using ammonium acetate and 2,4-thiazolidinedione instead of rhodanine and EDDA. $^1$H NMR (DMSO-d$_6$) δ 1.22 (s, 9H), 2.26 (bs, 4H), 3.43–3.45 (m, 6H), 4.88 (s, 2H), 5.17 (s, 2H), 6.95 (s, 1H), 7.12–7.27 (m, 5H), 7.58 (s, 1H).

Example 278

4-(3-tert-Butyl-5-morpholin-4-ylmethyl-benzyl)-6-[4-oxo-2-thioxo-thiazolidin-(5Z)-ylidenemethyl]-4H-benzo[1,4]oxazin-3-one The title compound was synthesized in a manner analogous to Example 19. $^1$H NMR (DMSO-d$_6$) δ 1.23 (s, 9H), 2.46–2.48 (bs, 4H), 3.52 (bs, 4H), 3.64 (bs, 2H), 4.88 (s, 2H), 5.18 (s, 2H), 7.02 (s, 1H), 7.10–7.13 (m, 2H), 7.19 (d, 1H), 7.21 (s, 1H), 7.33 (d, 1H). Microanalysis (C$_{28}$H$_{31}$N$_3$O$_4$S$_2$): calculated: C=62.55, H=5.81, N=7.81; found: C=62.58, H=5.00, N=7.17.

Example 279

4-[3-tert-Butyl-5-(4-methyl-piperazine-1-carbonyl)-benzyl]-6-[4-oxo-2-thioxo-thiazolidin-(5Z)-ylidenemethyl]-4H-benzo[1,4]oxazin-3-one.

The title compound was synthesized in a manner analogous to Example 59. $^1$H NMR (DMSO-d$_6$) δ 1.27 (9S, 9H), 2.43 (s, 3H), 2.56 (bs, 2H), 2.74 (b s, 2H), 3.28 (bs, 2H), 3.61 (bs, 2H), 4.88 (s, 2H), 5.21 (s, 2H), 7.10 (s, 1H), 7.17 (d, 1H), 7.19 (d, 1H), 7.26 (d, 2H), 7.53 (s, 1H). MS: M$^+$−1=563.2 Da.

Intermediate 81: 4-(6-Formyl-3-oxo-2,3-dihydro-benzo[1,4]oxazin-4-ylmethyl)-benzoic acid methyl ester. The title compound was synthesized in a manner analogous to intermediate 22 using intermediate 3 and 4-bromomethyl-benzoic acid methyl ester. MS: M$^+$+1=326.0 Da.

Intermediate 82: 4-(6-Formyl-3-oxo-2,3-dihydro-benzo[1,4]oxazin-4-ylmethyl)-benzoic acid. The title compound was synthesized in a manner analogous to intermediate 15 using intermediate 81. MS: M$^+$−1=310.0 Da.

Intermediate 83: 4-[4-(4-Methyl-piperazine-1-carbonyl)-benzyl]-3-oxo-3,4-dihydro-2H-benzo[1,4]oxazine-6-carbaldehyde. The title compound was synthesized in a manner analogous to intermediate 32 using intermediate 82 and 1-methylpiperazine. MS: M$^+$−1=393.2 Da.

Example 280

4-[4-(4-Methyl-piperazine-1-carbonyl)-benzyl]-6-[4-oxo-2-thioxo-thiazolidin-(5Z)-ylidenemethyl]-4H-benzo[1,4]oxazin-3-one The title compound was synthesized in a manner analogous to Example 1, from intermediate 83. $^1$H NMR (DMSO-d$_6$) δ 2.73 (bs, 3H), 3.29–3.43 (m, 8H), 4.86 (s, 2H), 5.18 (s, 2H), 7.05–7.16 (m, 3H), 7.21 (s, 1H), 7.36 (s, 4H). MS: M$^+$−1=507.1 Da.

Example 281

4-[4-(Morpholine-4-carbonyl)-benzyl]-6-[4-oxo-2-thioxo-thiazolidin-(5Z)-ylidenemethyl]-4H-benzo[1,4]oxazin-3-one The title compound was synthesized in a manner analogous to Example 280. $^1$H NMR (DMSO-d$_6$) δ 3.28 (bs, 4H), 3.50 (bs, 4H), 4.89 (s, 2H), 5.18 (s, 2H), 7.07 (s, 1H), 7.12 (d, 1H), 7.21 (d, 1H), 7.35 (s, 4H), 7.45 (s, 1H). MS: M$^+$−1=494.1 Da.

Example 282

4-[3-(1-Hydroxy-1-methyl-ethyl)-benzyl]-6-[4-oxo-2-thioxo-thiazolidin-(5Z)-ylidenemethyl]-4H-benzo[1,4]oxazin-3-one; Compound with ethane-1,2-diamine Microanalysis (C$_{22}$H$_{20}$N$_2$O$_4$S$_2$C$_2$H$_8$N$_2$): calculated: C=57.58, H=5.64, N=11.19; found: C=57.46, H=4.97, N=8.67. MS: M$^+$−1=439.1 Da.

Example 283

4-[3-tert-Butyl-5-(1-methoxy-1-methyl-ethyl)-benzyl]-6-[4-oxo-2-thioxo-thiazolidin-(5Z)-ylidenemethyl]-4H-benzo[1,4]oxazin-3-one.

Microanalysis (C$_{27}$H$_{30}$N$_2$O$_4$S$_2$): calculated: C=63.50, H=5.92, N=5.49; found: C=63.33, H=5.84, N=5.42. MS: M$^+$−1=509.1 Da.

Intermediate 84: Acetic acid 3-tert-butyl-5-(8-fluoro-6-formyl-3-oxo-2,3-dihydro-benzo[1,4]oxazin-4-ylmethyl)-benzyl ester. The title compound was synthesized in a manner analogous to intermediate 46 using intermediate 24 and acetic acid 3-bromomethyl-5-tert-butyl-benzyl ester. MS: M$^+$−1=413.4 Da.

Intermediate 85: 4-(3-tert-Butyl-5-hydroxymethyl-benzyl)-8-fluoro-3-oxo-3,4-dihydro-2H-benzo[1,4]oxazine-6-carbaldehyde. The title compound was synthesized in a manner analogous to intermediate 15 using intermediate 84. MS: M$^+$−1=413.1 Da.

Example 284

4-(3-tert-Butyl-5-hydroxymethyl-benzyl)-8-fluoro-6-[4-oxo-2-thioxo-thiazolidin-(5Z)-ylidenemethyl]-4H-benzo[1,4]oxazin-3-one The title compound was synthesized in a manner analogous to Example 1, from intermediate 85. Microanalysis (C$_{24}$H$_{23}$F$_1$N$_2$O$_4$S$_2$): calculated: C=59.24, H=4.76, N=5.76; found: C=59.20, H=4.57, N=5.75. MS: M$^+$−1=485.1 Da.

Example 285

Acetic acid 3-tert-butyl-5-{8-fluoro-3-oxo-6-[4-oxo-2-thioxo-thiazolidin-(5Z)-ylidenemethyl]-2,3-dihydro-benzo[1,4]oxazin-4-ylmethyl}-benzyl ester The title compound was synthesized in a manner analogous to Example 1, from intermediate 84. Microanalysis ($C_{26}H_{25}F_1N_2O_5S_2$): calculated: C=59.08, H=4.77, N=5.30; found: C=59.23, H=4.48, N=4.60. MS: $M^+-1=528.0$ Da.

Intermediate 86: 2-Oxo-2,3-dihydro-benzooxazole-5-carbaldehyde. To a 0° C. solution of methanol (50 mL) and 5-formyl-2-hydroxy-benzamide (Reich et al. *J. Med. Chem.*, 2000;43(9):1670–1683) (2.0 g, 12.11 mmol) was added potassium hydroxide (1.35 g, 24.22 mmol) and then iodobenzene diacetate (3.90 g, 12.11 mmol). The reaction was stirred at 0° C. for 1 hour, then diluted with ethyl acetate (200 mL) and carefully acidified to pH 2 with 1N HCl. The organic layer was then washed with sodium chloride (2×50 mL), dried over magnesium sulfate, filtered and concentrated under reduced pressure. This was used in the next step without purification. MS: $M^+-1=162.0$ Da.

Intermediate 82: 3-(3,4-Dichloro-benzyl)-2-oxo-2,3-dihydro-benzooxazole-5-carbaldehyde. The title compound was synthesized in a manner analogous to intermediate 46 using intermediate 86 and 4-bromomethyl-1,2-dichloro-benzene. MS: $M^++1=321.9$ Da.

Example 286

3-(3,4-Dichloro-benzyl)-5-[4-oxo-2-thioxo-thiazolidin-(5Z)-ylidenemethyl]-3H-benzooxazol-2-one The title compound was synthesized in a manner analogous to Example 1, from intermediate 87. Microanalysis ($C_{18}H_{10}Cl_2N_2O_3S_2$): calculated: C=49.44, H=2.30, N=6.41; found: C=49.46, H=2.20, N=6.19. MS: $M^+-1=435.9$ Da.

Example 287

4-(4-Iodo-benzyl)-6-[4-oxo-2-thioxo-thiazolidin-(5Z)-ylidenemethyl]-4H-benzo[1,4]oxazin-3-one The title compound was synthesized in a manner analogous to Example 38. Microanalysis ($C_{19}H_{13}I_1.N_2O_3S_2$): calculated: C=44.89, H=2.58, N=5.51; found: C=44.99, H=2.45, N=5.33. MS: $M^+-1=507.8$ Da.

Intermediate 88: 4-(6-Formyl-3-oxo-2,3-dihydro-benzo[1,4]oxazin-4-ylmethyl)-benzoic acid. The title compound was synthesized in a manner analogous to intermediate 15 using intermediate 81. MS: $M^+-1=310.0$ Da.

Example 288

4-{3-oxo-6-[4-oxo-2-thioxo-thiazolidin-(5Z)-ylidenemethyl]-2,3-dihydro-benzo[1,4]oxazin-4-ylmethyl}-benzoic acid; Compound with ethane-1,2-diamine The title compound was synthesized in a manner analogous to Example 1, from intermediate 88. Microanalysis ($C_{20}H_{14}N_2O_5S_2.C_2H_8N_2$): calculated: C=55.25, H=3.97, N=9.20; found: C=52.59, H=4.20, N=8.87. MS: $M^+-1=425.0$ Da.

Example 289

8-Fluoro-4-(4-methanesulfonyl-benzyl)-6-[4-oxo-2-thioxo-thiazolidin-(5Z)-ylidenemethyl]-4H-benzo[1,4]oxazin-3-one; Compound with Ethane-1,2-diamine The title compound was synthesized in a manner analogous to Example 46. Microanalysis ($C_{20}H_{15}F_1N_2O_5S_2.C_2H_8N_2$): calculated: C=49.59, H=3.77, N=8.26; found: C=47.31, H=3.56, N=7.50. MS: $M^+-1=477.0$ Da.

Example 290

3-Benzyl-5-[4-oxo-2-thioxo-thiazolidin-(5Z)-ylidenemethyl]-3H-benzooxazol-2-one; Compound with Ethane-1,2-diamine The title compound was synthesized in a manner analogous to Example 286. Microanalysis ($C_{18}H_{12}N_2O_3S_2.C_2H_8N_2$): calculated: C=57.27, H=4.05, N=10.55; found: C=57.19, H=4.01, N=10.49. MS: $M^+-1=367.0$ Da.

Example 291

3-(4-Methanesulfonyl-benzyl)-5-(4-oxo-2-thioxo-thiazolidin-5-ylidenemethyl)-3H-benzoxazol-2-one; Compound with Ethane-1,2-diamine.

The title compound was synthesized in a manner analogous to Example 286. Microanalysis ($C_{19}H_{14}N_2O_5S_3$ $C_2H_8N_2$): calculated: C=50.40, H=3.81, N=8.82; found: C=48.67, H=3.89, N=8.04. MS: $M^+-1=445.0$ Da.

Example 292

8-Fluoro-4-(4-fluoro-3-trifluoromethyl-benzyl)-6-(4-oxo-2-thioxo-thiazolidin-5-ylidenemethyl)-4H-benzo[1,4]oxazin-3-one The title compound was synthesized in a manner analogous to Example 46. Microanalysis ($C_{20}H_{11}N_2O_3S_2F_5$): calculated: C=49.38, H=2.28, N=5.76; found: C=49.26, H=2.21, N=5.71. MS: $M^++1=486.1$ Da.

Example 293

4-[3-Chloro-5-(1-hydroxy-1-methyl-ethyl)-benzyl]-8-fluoro-6-(4-oxo-2-thioxo-thiazoldin-5-ylidenemethyl)-4H-benzo[1,4]oxazin-3-one; Compound with Ethane-1,2-diamine The title compound was synthesized in a manner analogous to Example 46. $^1$H NMR (DMSO-$d_6$) δ 1.38 (s, 6H), 2.94 (s, 4H, ethylene diamine), 4.95 (s, 2H), 5.15 (s, 2H), 6.97 (s, 1H), 7.06–7.13 (m, 3H), 7.37 (t, 1H), 7.41 (d, 1H). MS: $M^+-1=492.1$ Da.

Example 294

8-Fluoro-4-[4-(1-hydroxy-1-methyl-ethyl)-benzyl]-6-(4-oxo-2-thioxo-thiazolidin-5-ylidenemethyl)-4H-benzo[1,4]oxazin-3-one The title compound was synthesized in a manner analogous to Example 46. $^1$H NMR (DMSO-d$_6$) δ 1.37 (s, 6H), 4.99 (s, 2H), 5.15 (bs, 2H), 6.99 (s, 1H), 7.23–7.26 (m, 3H), 7.41 (d, 2H), 7.49 (s, 1H). MS: M+−i=458.1 Da.

Example 295

4-(3,5-Difluoro-4-hydroxy-benzyl)-6-(4-oxo-2-thioxo-thiazolidin-5-ylidenemethyl)-4H-benzo[1,4]oxazin-3-one The title compound was synthesized in a manner analogous to Example 38. Microanalysis (C$_{19}$H$_{12}$N$_2$O$_4$S$_2$F$_2$): calculated: C=52.53, H=2.78, N=6.45; found: C=52.41, H=2.52, N=6.09. MS: M$^+$+1=435.1 Da.

Example 296

{5-[4-(3-Chloro-4-fluoro-benzyl)-8-fluoro-3-oxo-3,4-dihydro-2H-benzo[1,4]oxazin-6-ylmethylene]-4-oxo-2-thioxo-thiazolidin-3-yl}-acetic acid; compound with ethane-1,2-diamine The title compound was synthesized in a manner analogous to Example 46 using rhodanine-3-acetic acid in place of rhodanine. Microanalysis (C$_{21}$H$_{13}$N$_2$O$_5$S$_2$F$_2$Cl$_1$ 0.50 C$_2$H$_8$N$_2$[ethylene diamine].0.08 C$_1$H$_4$O$_1$): calculated: C=48.79, H=3.21, N=7.73; found: C=48.50, H=3.05, N=7.61. MS: M$^+$−1=511.0 Da.

Example 297

4-(3,5-Dibromo-benzyl)-8-fluoro-6-(4-oxo-2-thioxo-thiazolidin-5-ylidenemethyl)-4H-benzo[1,4]oxazin-3-one The title compound was synthesized in a manner analogous to Example 46. Microanalysis (C$_{19}$1H 1N$_2$O$_3$S$_2$F$_1$Br$_1$): calculated: C=40.88, H=1.99, N=5.02; found: C=41.15, H=1.95, N=4.88. MS: M$^+$−1=556.9 Da.

Example 298

5-[8-Fluoro-4-(4-fluoro-benzyl)-3-oxo-3,4-dihydro-2H-benzo[1,4]oxazin-6-ylmethylene]-thiazolidine-2,4-dione The title compound was synthesized in a manner analogous to Example 46 using thiazoladinedione instead of rhodanine. Microanalysis (C$_{19}$H$_{12}$N$_2$O$_4$S$_1$F$_2$): calculated: C=56.72, H=3.01, N=6.96; found: C=56.46, H=2.79, N=6.76. MS: M$^+$+1=403.1 Da.

Example 299

8-Fluoro-4-(4-methoxy-3-trifluoromethyl-benzyl)-6-(4-oxo-2-thioxo-thiazolidin-5-ylidenemethyl)-4H-benzo[1,4]oxazin-3-one The title compound was synthesized in a manner analogous to Example 46. Microanalysis (C$_{21}$H$_{14}$N$_2$O$_4$S$_2$F$_4$): calculated: C=50.60, H=2.83, N=5.62; found: C=50.47, H=2.54, N=5.62. MS: M$^+$−1=498.1 Da.

Example 300

4-(3-Chloro-4-fluoro-benzyl)-8-fluoro-6-(4-oxo-2-thioxo-oxazolidin-5-ylidenemethyl)-4H-benzo[1,4]oxazin-3-one The title compound was synthesized in a manner analogous to Example 46. Microanalysis (C$_{19}$H$_{11}$N$_2$O$_4$SF$_2$Cl$_1$): calculated: C=52.24, H=2.54, N=6.41; found: C=51.99, H=2.66, N=6.13. MS: M$^+$−1=437.0 Da.

Example 301

8-Fluoro-4-(4-fluoro-benzyl)-6-(4-oxo-2-thioxo-thiazolidin-5-ylidenemethyl)-4H-benzo[1,4]oxazin-3-one The title compound was synthesized in a manner analogous to Example 46. Microanalysis (C$_{19}$H$_{12}$N$_2$O$_3$S$_2$F$_2$): calculated: C=54.54, H=2.89, N=6.69; found: C=54.35, H=2.81, N=6.58. MS: M$^+$−1=419.0 Da.

Example 302

8-Fluoro-4-[4-fluoro-3-(1-hydroxy-1-methyl-ethyl)-benzyl]-6-(4-oxo-2-thioxo-thiazolidin-5-ylidenemethyl)-4H-benzo[1,4]oxazin-3-one; Compound with Ethane-1,2-diamine The title compound was synthesized in a manner analogous to Example 46. $^1$H NMR (DMSO-d$_6$) δ 1.44 (d, 6H), 2.93 (s, 4H, ethylene diamine), 4.91 (s, 2H), 5.14 (bs, 2H), 7.00–7.10 (m, 4H), 7.14–7.18 (m, 1H), 7.61 (dd, 1H). MS: M$^+$−1=476.0 Da.

Example 303

4-(4-Fluoro-benzyl)-6-(4-oxo-2-thioxo-thiazolidin-5-ylidenemethyl)-4H-benzo[1,4]oxazin-3-one The title compound was synthesized in a manner analogous to Example 38. Microanalysis (C$_{19}$H$_{13}$N$_2$O$_3$S$_2$F): calculated: C=56.99, H=3.27, N=7.00; found: C=57.04, H=3.11, N=6.96. MS: M$^+$+1=401.0 Da.

Example 304

4-[4-Fluoro-3-(1-hydroxy-1-methyl-ethyl)-benzyl]-6-(4-oxo-2-thioxo-thiazolidin-5-ylidenemethyl)-4H-benzo[1,4]oxazin-3-one; Compound with Ethane-1,2-diamine The title compound was synthesized in a manner analogous to Example 38. $^1$H NMR (DMSO-d$_6$) δ 1.41 (s, 6H), 2.92 (s, 4H, ethylenediamine), 4.80 (s, 2H), 5.15 (bs, 2H), 6.99–7.19 (m, 6H), 7.62 (dd, 1H). MS: M$^+$−1=458 Da.

Example 305

5-{4-[4-Fluoro-3-(1-hydroxy-1-methyl-ethyl)-benzyl]-3-oxo-3,4-dihydro-2H-benzo[1,4]oxazin-6-ylmethylene}-thiazolidine-2,4-dione The title compound was synthesized in a manner analogous to Example 272. Microanalysis ($C_{22}H_{19}N_2O_5SF$): calculated: C=59.72, H=4.33, N=6.33; found: C=59.78, H=4.10, N=6.17. MS: $M^+-1$=442.0 Da.

Example 306

4-(4-Fluoro-3-methyl-benzyl)-6-(4-oxo-2-thioxo-thiazolidin-5-ylidenemethyl)-4H-benzo[1,4]oxazin-3-one The title compound was synthesized in a manner analogous to Example 38. Microanalysis ($C_{20}H_{15}N_2O_3S_2F$): calculated: C=57.96, H=3.65, N=6.76; found: C=58.13, H=3.63, N=6.62. MS: $M^+-1$=442.0 Da.

Example 307

4-[3-(2-Fluoro-phenoxy)-benzyl]-3-oxo-3,4-dihydro-2H-benzo[1,4]oxazine-6-ylmethylene}-thiazolidine-2,4-dione The title compound was synthesized in a manner analogous to Example 272 using using BEMP resin as in intermediate 22. Microanalysis ($C_{25}H_{17}N_2O_5SF$): calculated: C=63.02, H=3.06, N=5.88; found: C=62.79, H=3.34, N=5.78. MS: $M^+ +1$=477.1 Da.

Example 308

5-[4-(3-Chloro-4-fluoro-benzyl)-3-oxo-3,4-dihydro-2H-benzo[1,4]oxazin-6-ylmethylene]-thiazolidine-2,4-dione The title compound was synthesized in a manner analogous to Example 307. Microanalysis ($C_{19}H_{12}N_2O_4SCl$): calculated: C=54.49, H=2.89, N=6.69; found: C=54.51, H=2.64, N=6.57. MS: $M^+ +1$=419.0 Da.

Example 309

4-(3-Chloro-4-fluoro-benzyl)-8-fluoro-6-(4-oxo-2-thioxo-thiazolidin-5-ylidenemethyl)-4H-benzo[1,4]oxazin-3-one The title compound was synthesized in a manner analogous to Example 46. Microanalysis ($C_{19}H_{11}N_2O_3S_2F_2Cl$): calculated: C=50.39, H=2.45, N=6.19; found: C=50.48, H=2.30, N=6.07. MS: $M^+ +1$=415.0 Da.

Example 310

8-Fluoro-4-[2-(4-fluoro-phenoxy)-ethyl]-6-(4-oxo-2-thioxo-thiazolidin-5-ylidenemethyl)-4H-benzo[1,4]oxazin-3-one The title compound was synthesized in a manner analogous to Example 46. Microanalysis ($C_{20}H_{14}N_2O_4S_2F_2$): calculated: C=53.56, H=3.15, N=6.25; found: C=53.54, H=3.18, N=6.16. MS: $M^+ +1$=449.0 Da.

Example 311

4-(3-Chloro-4-fluoro-benzyl)-6-(4-oxo-2-thioxo-thiazolidin-5-ylidenemethyl)-4H-benzo[1,4]oxazin-3-one The title compound was synthesized in a manner analogous to Example 38. Microanalysis ($C_{19}H_{12}N_2O_3S_2FCl$): calculated: C=52.47, H=2.78, N=6.44; found: C=52.39, H=2.55, N=6.18. MS: $M^+-1$=433.9 Da.

Example 312

4-(3,4-Difluoro-benzyl)-6-(4-oxo-2-thioxo-thiazolidin-5-ylidenemethyl)-4H-1,4-benzoxazin-3-one The title compound was synthesized in a manner analogous to Example 38. Microanalysis ($C_{19}H_{12}N_2O_3S_2F_2$): calculated: C=54.54, H=2.89, N=6.69; found: C=54.49, H=2.77, N=6.69. MS: $M^+ +1$=419.0 Da.

Example 313

4-{3-[Bis-(2-methoxy-ethyl)-amino]-propyl}-8-fluoro-6-(4-oxo-2-thioxo-thiazolidin-5-ylidenemethyl)-4H-benzo[1,4[oxazin-3-one The title compound was synthesized in a manner analogous to Example 19. $^1$H NMR (DMSO-$d_6$) δ 1.92–1.95 (m, 2H), 3.05–3.27 (m 10H), 3.54–3.57 (m, 4H), 3.95–3.98 (m, 2H), 4.80 (s, 2H), 7.12 (dd, 1H), 7.24 (s, 1H), 7.39 (s, 1H). MS: $M^+ +1$=484.1 Da.

Example 314

6-(4-Oxo-2-thioxo-thiazolidin-5-ylidenemethyl)-4-quinoxalin-6-ylmethyl-4H-benzo[1,4]oxazin-3-one The title compound was synthesized in a manner analogous to Example 38. $^1$H NMR (DMSO-$d_6$) δ 8.90 (s, 2H), 8.09 (d, J=8.5 Hz, 1H), 8.02 (d, J=1.4 Hz, 1H), 7.82 (dd, 1H), 7.47 (s, 1H), 7.23 (dd, 1H), 7.19 (s, 1H), 7.17 (t, 1H), 5.44 (s, 2H), 4.99 (s, 2H) ppm. MS: $M^+ +1$=435.1 Da.

Example 315

8-Fluoro-6-(4-Oxo-2-thioxo-thiazolidin-5-ylidenemethyl)-4-quinoxalin-6-ylmethyl-4H-benzo[1,4]oxazin-3-one; Compound with Ethane-1,2-diamine The title compound was synthesized in a manner analogous to Example 46. $^1$H NMR (DMSO-$d_6$) δ 8.89 (s, 2H), 8.09 (d, J=8.7 Hz, 1H), 7.99 (s, 1H), 7.82 (dd, 1H), 7.07 (d, J=11.2 Hz, 1H), 7.01 (s, 2H), 5.43 (s, 2H), 5.01 (s, 2H), [2.92 (s, 4H) 0.46 M of $C_2H_8N_2$] ppm. MS: $M^+ +1$=453.1Da.

Example 316

4-(5-Chloro-thiophen-2-ylmethyl)$_6$-(4-oxo-3-phenyl-2-thioxo-thiazolidin-5-ylidenemethyl)-4H-benzo[1,4]oxazin-3-one The title compound was synthesized in a manner analogous to Example 38, using 3-phenyl rhodanine instead of rhodanine. $^1$H NMR (DMSO-$d_6$) δ 7.826 (s, 1H), 7.605 (d, J=2.0 Hz, 1H), 7.565–7.475 (m, 3H), 7.401–7.376 (m, 2H), 7.328 (dd, 1H), 7.20 (d, J=8.3 Hz, 1H), 7.155 (d, J=3.9 Hz, 1H), 6.970 (d, J=3.65 Hz, 1H), 5.267 (s, 2H), 4.864 (s, 2H) ppm. MS: M⁻1=498.0 Da.

Example 317

4-(2,5-Dimethyl-furan-3-ylmethyl)-6-(4-oxo-2-thioxo-thiazolidin-5-ylidenemethyl)-4H-benzo[1,4]oxazin-3-one The title compound was synthesized in a manner analogous to Example 38. ¹H NMR (DMSO-d₆) δ 7.548 (s, 1H), 7.300 (d, J=2.0 Hz, 1H), 7.253–7.226 (dd, 1H), 7.137 (d, J=8.3 Hz, 1H), 5.812 (s, 1H), 4.891 (s, 2H), 4.803 (s, 2H), 2.268 (s, 3H), 2.100 (s, 3H) ppm. MS: M⁻1=399.1 Da.

Example 318

4-(2,5-Dimethyl-furan-3-ylmethyl)-8-fluoro-6-(4-oxo-2-thioxo-thiazolidin-5-ylidenemethyl)-4H-benzo[1,4]oxazin-3-one The title compound was synthesized in a manner analogous to Example 46. ¹H NMR (DMSO-d₆) δ 7.69 (s, 1H), 7.263 (dd, 1H), 7.091 (s, 1H), 4.902 (s, 4H), 2.267 (s, 3H), 2.105 (s, 3H) ppm. MS: M⁻1=417.1 Da.

Example 319

4-(5-Chloro-thiophen-2-ylmethyl)-8-fluoro-6-(4-oxo-2-thioxo-thiazolidin-5-ylidenemethyl)-4H-benzo[1,4]oxazin-3-one The title compound was synthesized in a manner analogous to Example 46. ¹H NMR (DMSO-d₆) δ 7.587 (s, 1H), 7.304 (s, 1H), 7.215 (dd, 1H), 7.135 (d, J=3.9 Hz, 1H), 6.967 (d, J=3.9 Hz, 1H), 5.248 (s, 2H), 4.934 (s, 2H), ppm. MS: M⁻1=439.1 Da.

Example 320

[4-oxo-5-(3-oxo-4-thiophen-2-ylmethyl-3,4-dihydro-2H-benzo[1,4]oxazin-6-ylmethylene)-2-thioxo-thiazolidin-3-yl]-acetic acid; Compound with ethane-1,2-diamine The title compound was synthesized in a manner analogous to Example 38, using rhodanine-3-acetic acid instead of rhodanine. ¹H NMR (DMSO-d₆) δ 7.778 (s, 1H), 7.555 (d, J=1.9 Hz, 1H), 7.418 (dd, 1H), 7.292 (dd, 1H), 7.202 (d, J=3.42 Hz, 1H), 7.168 (d, J=8.54 Hz, 1H), 6.960 (dd, 1H), 5.35 (s, 2H), 4.8421 (s, 2H), 4.42 (s, 2H), [2.788 (s, 4H) 0.46 M of C₂H₈N₂] ppm. MS: M⁻1=456.0 Da.

Example 321

{5-[4-(5-Methyl-2-triflouromethyl-furan-3-ylmethyl)-3-oxo-3,4-dihydro-2H-benzo[1,4]oxazin-6-ylmethylene]-4-oxo-2-thioxo-thiazolidin-3-yl}-acetic acid; Compound with ethane-1,2-diamine The title compound was synthesized in a manner analogous to Example 320. ¹H NMR (DMSO-d₆) δ 7.723 (s, 1H), 7.329 (dd, 1H), 7.204 (dd, 2H), 6.183 (s, 1H), 5.119 (s, 2H), 4.878 (s, 2H), 4.407 (s, 2H), 2.248 (s, 3H), [2.797 (s, 4H) 0.53M of C₂H₈N₂] ppm. MS M⁻1=511.1 Da.

Example 322

4-(5-Chloro-thiophen-2-ylmethyl)-6-(4-oxo-2-thioxo-thiazolidin-5-ylidenemethyl)-4H-benzo[1,4]oxazin-3-one The title compound was synthesized in a manner analogous to Example 38. ¹H NMR (DMSO-d₆) δ 7.627 (s, 1H), 7.520 (d, J=1.9 Hz, 1H), 7.26 (dd, 1H), 7.17 (s, 1H), 7.149 (d, J=2.9 Hz, 1H), 6.962 (d, J=3.9 Hz, 1H), 5.244 (s, 2H), 4.839 (s, 2H) ppm. MS: M⁻1=421.0 Da.

Example 323

6-(4-Oxo-2-thioxo-thiazolidin-5-ylidenemethyl)-4-quinolin-3-ylmethyl-4H-benzo[1,4]oxazin-3-one The title compound was synthesized in a manner analogous to Example 38. ¹H NMR (DMSO-d₆) δ 8.930 (d, 1H), 8.243 (s, 1H) 7.988 (d, J=10.0 Hz, 1H), 7.925 (d, J=9.27 Hz, 1H), 7.690 (t, 1H) 7.585–7.544 (m, 1H), 7.251 (s, 2H), 7.139 (s, 2H), 5.391 (s, 2H), 4.930 (s, 2H), [2.953 (s, 4H) 0.30M of C₂H₈N₂] ppm. MS M⁺+1=434.1 Da.

Example 324

4-(5-Methyl-2-triflouromethyl-furan-3-ylmethyl)-6-(4-oxo-2-thioxo-thiazolidin-5-ylidenemethyl)-4H-benzo[1,4]oxazin-3-one The title compound was synthesized in a manner analogous to Example 38. ¹H NMR (DMSO-d₆) δ 7.541 (s, 1H), 7.283 (dd, 1H), 7.185 (d, J=8.6 Hz, 1H), 7.150 (d, J=2.0 Hz, 1H), 6.164 (s, 1H), 5.105 (s, 2H), 4.866 (s, 2H), 2.242 (d, J=1.0 Hz, 3H) ppm. MS: M⁻1=453.1 Da.

Example 325

4-(1-tert-Butyl-5-methyl-1H-pyrazol-3-ylmethyl)-8-flouro-6-(4-oxo-2-thioxo-thiazolidin-5-ylidenemethyl)-4H-benzo[1,4]oxazin-3-one The title compound was synthesized in a manner analogous to Example 46. ¹H NMR (DMSO-d₆) δ 7.491 (s, 1H), 7.336 (dd, 1H), 7.187 (s, 1H), 5.877 (s, 1H), 4.989 (s, 2H), 4.906 (s, 2H), 2.315 (s, 3H), 1.507 (s, 9H) ppm. MS: M⁺+1=461.2 Da.

Example 326

4-(1-tert-Butyl-5-methyl-1H-pyrazol-3-ylmethyl)-6-(4-oxo-2-hioxo-thiazolidin-5-ylidenemethyl)-4H-benzo[1,4]oxazin-3-one The title compound was synthesized in a manner analogous to Example 38. ¹H NMR (DMSO-d₆) δ 7.500 (s, 1H), 7.385 (d, J=2.2 Hz, 1H), 7.267 (dd, 1H), 7.120 (d, J=8.3 Hz, 1H), 5.860 (s, 1H), 4.984 (s, 2H), 4.811 (s, 2H), 2.312 (d, J=0.5 Hz, 3H), 1.513 (s, 9H) ppm. MS: M⁻1=441.2 Da.

Example 327

4-(2-Benzyl-5-tert-butyl-2H-pyrazol-3-ylmethyl)-6-(4-oxo-2-thioxo-thiazolidin-5-ylidenemethyl)-4H-benzo[1,4]oxazin-3-one The title compound was synthesized in a manner analogous to Example 38. $^1$H NMR (DMSO-$d_6$) δ 7.480 (s, 1H), 7.291–7.212 (m, 4H), 7.107 (d, J=8.6 Hz, 1H), 7.057–7.036 (m, 3H), 6.094 (s, 1H), 5.376 (s, 2H), 5.046 (s, 2H), 4.737 (s, 2H), 1.170 (s, 9H) ppm. MS: M$^-$1=519.2 Da.

Example 328

8-Fluoro-6-(4-oxo-2-thioxo-thiazolidin-5-ylidenemethyl)-4-quinolin-6-ylmethyl-4H-1,4-benzoxazin-3-one The title compound was synthesized in a manner analogous to Example 46. $^1$H NMR (DMSO-$d_6$) δ 8.849 (q, 1H), 8.282 (d, 1H), 8.000 (d, 1H), 7.918 (s, 1H), 7.713 (dd, 1H), 7.512–7.481 (m, 1H), 7.404 (s, 1H), 7.261 (d, 1H), 6.950 (s, 1H), 5.393 (s, 2H), 5.064 (s, 2H) ppm. MS: M$^-$1=450.1 Da.

Example 329

4-(1,5-Dimethyl-1H-pyrazol-3-ylmethyl)-6-(4-oxo-2-thioxo-thiazolidin-5-ylidenemethyl)-4H-1,4-benzoxazin-3-one The title compound was synthesized in a manner analogous to Example 38. $^1$H NMR (DMSO-$d_6$) δ 7.525 (s, 1H), 7.295 (s, 1H), 7.273 (d, J=1.9 Hz, 1H), 7.118 (d, J=8.5 Hz, 1H), 5.904 (s, 1H), 4.972 (s, 2H), 4.804 (s, 2H), 3.684 (s, 3H), 2.166 (s, 3H) ppm. MS: M$^-$1=399.1 Da.

Example 330

4-(5-Chloro-pyridin-3-ylmethyl)-8-fluoro-6-(4-oxo-2-thioxo-thiazolidin-5-ylidenemethyl)-4H-1,4-benzoxazin-3-one The title compound was synthesized in a manner analogous to Example 46. $^1$H NMR (DMSO-$d_6$) δ 8.540 (d, J=1.7 Hz, 1H), 8.527 (d, J=1.7 Hz, 1H), 7.890 (t, J=2.1 Hz, 1H), 7.20–7.116 (m, 2H), 6.941 (s, 1H), 5.213 (s, 2H), 4.978 (s, 2H), [2.953 (s, 4H) 0.31M of $C_2H_8N_2$], ppm. MS: M$^-$1=434.0 Da.

Example 331

4-[4-Chloro-3-(1-hydroxy-1-methyl-ethyl)-benzyl]-8-fluoro-6-(4-oxo-2-thioxo-thiazolidin-5-ylidenemethyl)-4H-1,4-benzoxazin-3-one; Compound with Ethane-1,2-diamine The title compound was synthesized in a manner analogous to Example 46. $^1$H NMR (DMSO-$d_6$) δ 7.805.90 (d, J=2.1 Hz, 1H), 7.278 (d, J=8.1 Hz, 1H), 7.104 (dd, J=5.8 Hz, J=2.5 Hz, 2H), 7.040 (d, J=12.2 Hz, 1H), 6.970 (s, 1H), 5.146 (s, 2H), 4.917 (s, 2H), 1.539 (s, 6H), [2.953 (s, 4H) 0.31M of $C_2H_8N_2$] ppm. MS: M$^-$1=491.0 Da. Example 332: 4-[4-Chloro-3-(1-hydroxy-1-methyl-ethyl)-benzyl]-6-(4-oxo-2-thioxo-thiazolidin-5-ylidenemethyl)-4H-1,4-benzoxazin-3-one; compound with ethane-1,2-diamine. The title compound was synthesized in a manner analogous to Example 38. $^1$H NMR (DMSO-$d_6$) δ 7.822 (d, J=2.2 Hz, 1H), 7.284 (d, J=8.0 Hz, 1H), 7.132 (s, 1H), 7.113–7.08 (m, 4H), 5.149 (s, 2H), 4.829 (s, 2H), 1.548 (s, 6H), [2.890 (s, 4H) 0.52M of $C_2H_8N_2$] ppm. MS: M$^-$1=473.1 Da.

Example 333

6-(4-Oxo-2-thioxo-thiazolidin-5-ylidenemethyl)-4-thiophen-2-ylmethyl-4H-1,4-benzoxazin-3-one The title compound was synthesized in a manner analogous to Example 38. $^1$H NMR (DMSO-$d_6$) δ 7.572 (s, 1H), 7.476 (d, J=2.0 Hz, 1H), 7.389 (dd, J=3.9 Hz, J=1.2 Hz, 1H), 7.206–7.185 (m, 2H), 7.120 d, J=8.3 Hz, 1H), 6.932–6.911 (m, 1H), 5.301 (s, 2H), 4.807 (s, 2H) ppm. MS: M$^-$1=387.0 Da.

Example 334

4-(5-Methyl-pyridin-3-ylmethyl)-6-(4-oxo-2-thioxo-thiazolidin-5-ylidenemethyl)-4H-1,4-benzoxazin-3-one The title compound was synthesized in a manner analogous to Example 38. $^1$H NMR (DMSO-$d_6$) δ 8.327 (s, 1H), 8.286 (s, 1H), 7.539 (s, 1H), 7.495 (s, 1H), 7.216 (dd, J=6.6 Hz, J=1.9 Hz, 1H), 7.126 (d, J=8.3 Hz, 1H), 7.076 (d, J=1.9 Hz, 1H), 5.151 (s, 2H), 4.901 (s, 2H), 2.254 (s, 3H) ppm. MS: M$^+$+1=398.0 Da.

Example 335

4-(1-Isopropyl-1H-benzimidazol-5-ylmethyl)-6-(4-oxo-2-thioxo-thiazolidin-5-ylidenemethyl)-4H-1,4-benzoxazin-3-one The title compound was synthesized in a manner analogous to Example 38. $^1$H NMR (DMSO-$d_6$) δ 8.295 (s, 1H), 7.555 (s, 1H), 7.578 (d, J=8.3 Hz, 1H), 7.439 (s, 1H), 7.236 (s, 1H), 7.223 (s, 1H), 7.166 (d, J=8.6 Hz, 1H), 7.110 (d, J=8.3 Hz, 1H), 5.252 (s, 2H), 4.905 (s, 2H), 4.710–4.643 (m, 1H), 1.462 (d, J=6.8 Hz, 6H) ppm. MS: M$^+$+1=465.1 Da.

Example 336

4-(3-Isopropyl-3H-benzimidazol-5-ylmethyl)-6-(4-oxo-2-thioxo-thiazolidin-5-ylidenemethyl)-4H-1,4-benzoxazin-3-one The title compound was synthesized in a manner analogous to Example 38. $^1$H NMR (DMSO-$d_6$) δ 8.279 (d, 1H), 7.683 (s, 1H), 7.549–7.517 (m, 1H), 7.422 (s, 1H), 7.224 (s, 1H), 7.176 (d, J=8.6 Hz, 1H), 7.110–7.053 (m, 2H), 5.287 (s, 2H), 4.897 (s, 2H), 4.698–4.665 (m, 1H), 1.468 (d, 6.6 Hz, 6H) ppm. MS: M$^+$+1=465.1 Da.

Example 337

6-(4-Oxo-2-thioxo-thiazolidin-5-ylidenemethyl)-4-quinolin-6-ylmethyl-4H-1,4-benzoxazin-3-one The title compound was synthesized in a manner analogous to Example 38. $^1$H NMR (DMSO-$d_6$) δ 8.816 (dd, J=2.5 Hz, J=1.7 Hz, 1H), 8.258 (d, J=7.5 Hz, 1H), 7.969 (d, J=8.6 Hz, 1H), 7.879 (s, 1H), 7.684 (dd, J=7.1 Hz, J=1.7 Hz, 1H), 7.479–7.448 (m, 1H), 7.393 (s, 1H), 7.195 (d, J=8.6 Hz, 1H), 7.147–7.126 (m, 2H), 5.352 (s, 2H), 4.944 (s, 2H) ppm. MS: M$^+$+1=434.0 Da.

Example 338

5-(4-Furan-3-ylmethyl-3-oxo-3,4-dihydro-2H-1,4-benzoxazin-6-ylmethylene)-thiazolidine-2,4-dione The title compound was synthesized in an analogous manner to Example 272. $^1$H NMR (DMSO-$d_6$) δ 7.749 (s, 1H), 7.717 (s, 1H), 7.594 (t, J=1.8 Hz, 1H), 7.360 (d, J=2.0 Hz, 1H), 7.214 (dd, J=6.6 Hz, J=2.0 Hz, 1H), 7.130 (d, J=8.2 Hz, 1H), 6.420 (dd, J=1.2 Hz, 1.0 Hz, 1H), 4.971 (s, 2H), 4.810 (s, 2H) ppm. MS: M$^-$1=355.0 Da.

Example 339

4-(2,5-Dimethyl-2H-pyrazol-3-ylmethyl)-6-(4-oxo-2-thioxo-thiazolidin-5-ylidenemethyl)-4H-1,4-benzoxazin-3-one The title compound was synthesized in a manner analogous to Example 38. $^1$H NMR (DMSO-$d_6$) δ 7.544 (s, 1H), 7.322 (d, J=1.7 Hz, 1H), 7.219 (dd, J=6.5 Hz, J=1.9 Hz, 1H), 7.165 (d, J=8.4 Hz, 1H), 5.808 (s, 1H), 5.153 (s, 2H), 4.843 (s, 2H), 3.767 (s, 3H), 2.001 (s, 3H) ppm. MS: M$^+$+1=401.0 Da.

Example 340

4-Furan-3-ylmethyl-6-(4-oxo-2-thioxo-thiazolidin-5-ylidenemethyl)-4H-1,4-benzoxazin-3-one The title compound was synthesized in a manner analogous to Example 38. $^1$H NMR (DMSO-$d_6$) δ 7.719 (s, 1H), 7.604 (s, 1H), 7.591 (t, J=1.7 Hz, 1H), 7.377 (d, J=2.2 Hz, 1H), 7.223–7.198 (m, 1H), 7.130 (d, J=8.6 Hz, 1H), 6.425 (dd, J=1.0 Hz, J=0.7 Hz, 1H), 4.980 (s, 2H), 4.819 (s, 2H) ppm. MS: M$^-$1=371.0 Da.

Example 341

4-(3,4-Dichloro-benzyl)-8-fluoro-6-[4-oxo-2-thioxo-thiazolidin-(5Z)-ylidenemethyl]-4H-benzo[1,4]oxazin-3-one The title compound was synthesized in a manner analogous to Example 46. Microanalysis ($C_{19}H_{11}C_{12}F_1N_2O_3S_2$): calculated: C=48.62, H=2.36, N=5.97; actual: C=48.57, H=2.33, N=5.94. MS: M$^+$−1=466.9 Da.

Biological Example 1

PI3Kγ Protein Expression and Purification Protocol

*Spodtera frugiperda* cells, grown in ESF921 media, were coinfected with baculovirus expressing a glu-tagged p101 and baculovirus expressing an HA-tagged p110γ, at a 3:1 ratio of p101 baculovirus to p110γ baculovirus. Sf9 cells were grown to 1×10$^7$ total cells/mL in 10L bioreactors and harvested 48–72 hours post infection. Samples of infected cells were then tested for expression of p101/p110γ PI3 kinase by immunoprecipitation and Western Blot analysis methods (see below).

To purify PI3Kγ, 4 volumes of room temperature hypotonic lysis buffer (1 mM MgCl$_2$, 1 mM DTT, 5 mM EGTA, 1 mM Pefabloc, 0.5 µM aprotinin, 5 µM leupeptin, 2 µM pepstatin, 5 µM E64, pH 8) per gram of cell paste, was poured onto frozen cell pellets with stirring, then lysed in a nitrogen "bomb" at 400 psi (599HC T316, Parr Instrument Co, Moline, Ill.). NaCl was added to 150 mM, and sodium cholate was added to 1% and mixed for another 45 minutes. The lysates were clarified by centrifugation for 25 minutes at 14,000 rpm. The lysates were then loaded over anti-glu-linked Protein-G Sepharose beads (Covance Research Products, Richmond, Calif.) using 20 mL resin/50 g cell paste. The column was washed with 15 volumes of wash buffer (1 mM DTT, 0.2 mM EGTA, 1 mM Pefabloc, 0.5 [M aprotinin, 5 µM leupeptin, 2 µM pepstatin, 5 µM E64, 150 mM NaCl, 1% sodium cholate, pH 8). PI3Kγ was eluted with 6 column volumes of wash buffer that contain 100 µg/mL of a peptide that competes for binding of the glu tag. The column fractions with the eluted protein (determined by taking OD$_{280}$ readings) were collected and dialyzed in 0.2 mM EGTA, 1 mM DTT, 1 mM Pefabloc, 5 µM leupeptin, 0.5% sodium cholate, 150 mM NaCl, and 50% glycerol, pH 8. The fractions were stored at −80° C. until further use.

Biological Example 2

G Protein Subunits Expression

*Spodtera frugiperda* cells were coinfected with baculovirus expressing a glu-tagged G protein β$_1$ and baculovirus expressing a G protein β$_2$ at a 1:1 ratio of glu-tagged G protein β$_1$ baculovirus to G protein β2 baculovirus. Sf9 cells are grown in 10 L bioreactors and harvested 48–72 hours post infection. Samples of infected cells were tested for G protein β$_1$/β$_2$ expression by Western Blot analysis, as described below. Cell lysates were homogenized and loaded onto a column of glu-tagged beads as in Biological Example 1 and competed off the column with a glu peptide as described in Biological Example 1.

Biological Example 3

Western Blot Analysis

Protein samples were run on an 8% Tris-Glycine gel and transferred to a 45 µM nitrocellulose membrane. The blots were then blocked with 5% bovine serum albumin (BSA) and 5% ovalbumin in TBST (50 mM Tris, 200 mM NaCl, 0.1% Tween 20, ph 7.4) for 1 hour at room temperature, and incubated overnight at 4° C. with primary antibody diluted 1:1000 in TBST with 0.5% BSA. The primary antibodies for the p110γ, p110α, p110β, p85α, G protein β$_1$, and G protein γ$_2$ subunits were purchased from Santa Cruz Biotechnology, Inc., Santa Cruz, Calif. The p101 subunit antibodies were developed at Research Genetics, Inc., Huntsville, Ala. based on a p101 peptide antigen.

After incubation with the primary antibody, the blots were washed in TBST and incubated for 2 hours at room temperaure with goat-anti-rabbit HRP conjugate (Bio-Rad Laboratories, Inc., Hercules, Calif., product Number 170–6515), diluted 1:10,000 in TBST with 0.5% BSA. The antibodies were detected with ECL™ detection reagents (Amersham Biosciences Corp., Piscataway, N.J.) and quantified on a Kodak ISO400F scanner.

Biological Example 4

Immunoprecipitation

100 µL of cell paste from Biological Example 1 or 2 was thawed and lysed on ice with 400 µL of hypotonic lysis buffer (25 mM tris, 1 mM DTT, 1 mM EDTA, 1 mM Pefabloc, 5 µM leupeptin, 5 µM E-64 (Roche), 1% Nonidet P40, pH 7.5–8). The lysate was incubated for 2 hours at room temperature with glu-tagged beads (Covance Research Products, Cambridge, England, product Number AFC-115P). The beads were washed 3 times in wash buffer (20 mM Tris, pH 7.8–8, 150 mM NaCl$_2$, 0.5% NP40) and the protein eluted off the beads by heating in 2 times sample buffer (Invitrogen Corporation, Carlsbad, Calif., product Number LC1676).

Biological Example 5

PI3Kγ In Vitro Kinase Assay

The inhibitory properties of the compounds in Table 1 were assayed in an in vitro PI3K assay. In a 96-well polypropylene plate, each well was spotted with 2 µL of 50 times the desired final concentration of compound in DMSO. Purified recombinant p101/p110γ protein (0.03 µg; ~2.7 nM) and G protein β$_1$/γ$_2$ subunits (0.09 µg; ~57.7 nM) for each reaction was combined in the assay buffer (30 mM HEPES, 100 mM NaCl, 1 mM EGTA, and 1 mM DTT). ATP and [γ-$^{32}$P-ATP] (0.09 µCi) were added to this mixture so that the final ATP concentration in the reaction was 20 µM. Lipid micelles were formed by sonicating phosphatidylinositol-4,5-diphosphate (PIP$_2$), phosphatidylethanolamine (PE), and Na-cholate in the assay buffer for 10 minutes, adding MgCL$_2$ and incubating on ice for 20 minutes, for final concentrations of 25 µM PIP$_2$, 300 [M PE, 0.02% Na-cholate, and 10 mM MgCl$_2$ in the reaction. The reactions were started by adding equal volumes lipid and enzyme mixture in a total volume of 50 µL, allowed to run for 20 minutes at room temperature, and stopped with 100 µL 75 mM H$_3$PO$_4$. The lipid product was transferred to a glass fiber filter plate and washed with 75 mM H$_3$PO$_4$ several times. The presence of radioactive lipid product (PIP$_3$) was measured by adding Wallac Optiphase mix to each well and counting in a Wallac 1450 Trilux plate reader (PerkinElmer Life Sciences Inc., Boston, Mass. 02118). The IC$_{50}$ for each compound tested is reported in µM in Table 1:

TABLE 1

| Ex No. | IC$_{50}$ (µM) |
| --- | --- |
| 1 | 0.078 |
| 2 | 0.045 |
| 3 | 0.635 |
| 4 | 0.023 |
| 5 | 0.025 |
| 6 | 0.560 |
| 7 | 0.084 |
| 8 | 0.081 |
| 9 | 0.061 |
| 10 | 3.635 |
| 11 | 0.061 |
| 12 | 0.027 |
| 13 | 0.745 |
| 14 | 0.005 |
| 15 | 0.013 |
| 16 | 0.328 |
| 17 | 0.009 |
| 18 | 0.319 |
| 19 | 0.008 |
| 20 | 0.003 |
| 21 | 0.014 |
| 22 | 0.017 |
| 23 | 0.005 |
| 24 | 0.003 |
| 25 | 0.008 |
| 26 | 0.009 |
| 27 | 0.003 |
| 28 | 0.003 |

TABLE 1-continued

| Ex No. | IC$_{50}$ (µM) |
| --- | --- |
| 29 | 0.031 |
| 30 | 0.002 |
| 31 | 0.083 |
| 32 | 0.012 |
| 33 | 0.004 |
| 34 | 0.003 |
| 35 | 0.012 |
| 36 | 0.002 |
| 37 | 1.625 |
| 38 | 0.006 |
| 39 | 0.335 |
| 40 | 0.015 |
| 41 | 0.061 |
| 42 | 0.041 |
| 43 | 1.445 |
| 44 | 0.265 |
| 45 | 0.336 |
| 46 | 0.008 |
| 47 | 0.320 |
| 48 | 0.042 |
| 49 | 0.061 |
| 50 | 0.010 |
| 51 | 0.165 |
| 52 | 0.016 |
| 53 | 0.043 |
| 54 | 0.040 |
| 55 | 0.009 |
| 56 | 0.018 |
| 57 | 0.029 |
| 58 | 0.032 |
| 59 | 0.070 |
| 60 | 0.026 |
| 61 | 0.070 |
| 62 | 0.850 |
| 63 | 0.049 |
| 64 | 0.016 |
| 65 | 0.095 |
| 66 | 0.257 |
| 67 | 0.060 |
| 68 | 0.555 |
| 69 | 0.008 |
| 70 | 0.012 |
| 71 | 0.006 |
| 72 | 0.014 |
| 73 | 0.007 |
| 74 | 0.019 |
| 75 | 0.155 |
| 76 | 0.006 |
| 77 | 0.021 |
| 78 | 0.057 |
| 79 | 0.020 |
| 80 | 0.017 |
| 81 | 0.029 |
| 82 | 3.735 |
| 83 | 0.260 |
| 84 | 0.060 |
| 85 | 0.021 |
| 86 | 12.300 |
| 87 | 16.100 |
| 88 | 0.003 |
| 89 | 0.004 |
| 90 | 0.004 |
| 91 | 0.008 |
| 92 | 0.006 |
| 93 | 0.016 |
| 94 | 0.029 |
| 95 | 0.225 |
| 96 | 0.670 |
| 97 | 0.003 |
| 98 | 0.005 |
| 99 | 0.018 |
| 100 | 0.005 |
| 101 | 0.005 |
| 102 | 0.002 |
| 103 | 0.004 |
| 104 | 0.002 |
| 105 | 0.005 |

TABLE 1-continued

| Ex No. | IC$_{50}$ (µM) |
|---|---|
| 106 | 0.009 |
| 107 | 0.072 |
| 108 | 0.004 |
| 109 | 0.330 |
| 110 | 0.055 |
| 111 | 0.014 |
| 112 | 0.022 |
| 113 | 0.014 |
| 114 | 0.005 |
| 115 | 0.015 |
| 116 | 0.024 |
| 117 | 0.040 |
| 118 | 0.023 |
| 119 | 0.019 |
| 120 | 0.030 |
| 121 | 0.067 |
| 122 | 0.005 |
| 123 | 0.007 |
| 124 | 0.015 |
| 125 | 0.018 |
| 126 | 0.010 |
| 127 | 0.043 |
| 128 | 0.180 |
| 129 | 0.049 |
| 130 | 0.003 |
| 131 | 0.039 |
| 132 | 0.012 |
| 133 | 0.005 |
| 134 | 0.005 |
| 135 | 0.005 |
| 136 | 0.007 |
| 137 | 0.003 |
| 138 | 0.010 |
| 139 | 0.042 |
| 140 | 0.029 |
| 141 | 0.860 |
| 142 | 0.044 |
| 143 | 0.035 |
| 144 | 0.024 |
| 145 | 0.026 |
| 146 | 0.030 |
| 147 | 0.049 |
| 148 | 0.061 |
| 149 | 0.021 |
| 150 | 0.005 |
| 151 | 0.061 |
| 152 | 1.030 |
| 153 | 0.096 |
| 154 | 0.160 |
| 155 | 0.010 |
| 156 | 0.021 |
| 157 | 0.021 |
| 158 | 0.028 |
| 159 | 0.010 |
| 160 | 0.007 |
| 161 | 0.004 |
| 162 | 0.053 |
| 163 | 0.030 |
| 164 | 0.013 |
| 165 | 0.015 |
| 166 | 0.020 |
| 167 | 0.010 |
| 168 | 0.012 |
| 169 | 0.008 |
| 170 | 0.009 |
| 171 | 0.015 |
| 172 | 0.145 |
| 173 | 0.039 |
| 174 | 0.002 |
| 175 | 0.004 |
| 176 | 0.059 |
| 177 | 0.025 |
| 178 | 0.004 |
| 179 | 0.007 |
| 180 | 0.009 |
| 181 | 0.010 |
| 182 | 0.165 |

TABLE 1-continued

| Ex No. | IC$_{50}$ (µM) |
|---|---|
| 183 | 0.021 |
| 184 | 0.003 |
| 185 | 0.102 |
| 186 | 0.315 |
| 187 | 0.098 |
| 188 | 0.020 |
| 189 | 0.640 |
| 190 | 0.240 |
| 191 | 0.007 |
| 192 | 0.008 |
| 193 | 0.006 |
| 194 | 0.006 |
| 195 | 1.910 |
| 196 | 0.026 |
| 197 | 0.390 |
| 198 | 0.006 |
| 199 | 0.009 |
| 200 | 3.64 |
| 201 | 0.070 |
| 202 | 0.003 |
| 203 | 0.175 |
| 204 | 0.016 |
| 205 | 0.032 |
| 206 | 0.060 |
| 207 | 0.002 |
| 208 | 0.002 |
| 209 | 0.074 |
| 210 | 0.045 |
| 211 | 0.017 |
| 212 | 0.022 |
| 213 | 2.095 |
| 214 | 3.180 |
| 215 | 1.085 |
| 216 | 0.026 |
| 217 | 0.042 |
| 218 | 0.055 |
| 219 | 0.006 |
| 220 | 0.495 |
| 221 | 0.895 |
| 222 | 0.006 |
| 223 | 0.295 |
| 224 | 0.255 |
| 225 | 0.049 |
| 226 | 34.200 |
| 227 | 0.048 |
| 228 | 0.003 |
| 229 | 0.020 |
| 230 | 0.043 |
| 231 | 0.050 |
| 232 | 0.125 |
| 233 | 0.035 |
| 234 | 2.070 |
| 235 | 1.240 |
| 236 | 0.005 |
| 237 | 0.006 |
| 238 | 0.036 |
| 239 | 0.039 |
| 240 | 0.032 |
| 241 | 0.052 |
| 242 | 0.055 |
| 243 | 0.180 |
| 244 | 0.185 |
| 245 | 0.185 |
| 246 | 0.003 |
| 247 | 0.010 |
| 248 | 0.021 |
| 249 | 0.008 |
| 250 | 0.175 |
| 251 | 0.025 |
| 252 | 0.021 |
| 253 | 0.016 |
| 254 | 0.010 |
| 255 | 0.015 |
| 256 | 0.020 |
| 257 | 0.028 |
| 258 | 0.004 |
| 259 | 0.013 |

TABLE 1-continued

| Ex No. | IC$_{50}$ (µM) |
|---|---|
| 260 | 0.004 |
| 261 | 0.002 |
| 262 | 0.019 |
| 263 | 0.018 |
| 264 | 0.004 |
| 265 | 0.018 |
| 266 | 1.610 |
| 267 | 0.460 |
| 268 | 4.640 |
| 269 | 0.014 |
| 270 | 0.011 |
| 271 | 0.101 |
| 272 | 0.070 |
| 273 | 0.121 |
| 274 | 0.013 |
| 275 | 0.025 |
| 276 | 0.007 |
| 277 | 0.005 |
| 278 | 0.007 |
| 279 | 0.016 |
| 280 | 0.008 |
| 281 | 0.008 |
| 282 | 0.013 |
| 283 | 0.011 |
| 284 | 0.010 |
| 285 | 0.021 |
| 286 | 0.220 |
| 287 | 0.016 |
| 288 | 0.035 |
| 289 | 0.010 |
| 290 | 0.243 |
| 291 | 0.433 |
| 292 | 0.011 |
| 293 | 0.015 |
| 294 | 0.003 |
| 295 | 0.004 |
| 296 | 3.850 |
| 297 | 0.036 |
| 298 | 0.001 |
| 299 | 0.006 |
| 300 | 0.003 |
| 301 | 0.001 |
| 302 | 0.012 |
| 303 | 0.002 |
| 304 | 0.008 |
| 305 | 0.016 |
| 306 | 0.001 |
| 307 | 0.005 |
| 308 | 0.001 |
| 309 | 0.002 |
| 310 | 0.009 |
| 311 | 0.001 |
| 312 | 0.003 |
| 313 | 0.035 |
| 314 | 0.036 |
| 315 | 0.044 |
| 316 | 3.700 |
| 317 | 0.021 |
| 318 | 0.025 |
| 319 | 0.005 |
| 321 | 9.730 |
| 322 | 0.003 |
| 323 | 0.029 |
| 324 | 0.033 |
| 325 | 0.018 |
| 326 | 0.025 |
| 327 | 0.245 |
| 328 | 0.006 |
| 329 | 0.028 |
| 330 | 0.047 |
| 331 | 0.009 |
| 332 | 0.007 |
| 333 | 0.007 |
| 334 | 0.025 |
| 335 | 0.034 |
| 336 | 0.009 |
| 337 | 0.008 |
| 338 | 0.012 |
| 339 | 0.080 |
| 340 | 0.013 |
| 341 | 0.003 |

Formulation Example 1

Tablet Formulation

| Ingredient | Amount |
|---|---|
| Compound of Formula I | 50 mg |
| Lactose | 80 mg |
| Cornstarch (for mix) | 10 mg |
| Cornstarch (for paste) | 8 mg |
| Magnesium Stearate (1%) | 2 mg |
| | 150 mg |

The compounds of the present invention (e.g., a compound of Formula I, or a pharmaceutically acceptable salt thereof) can be mixed with the lactose and cornstarch (for mix) and blended to uniformity to a powder. The cornstarch (for paste) is suspended in 6 mL of water and heated with stirring to form a paste. The paste is added to the mixed powder, and the mixture is granulated. The wet granules are passed through a No. 8 hard screen and dried at 50° C. The mixture is lubricated with 1% magnesium stearate and compressed into a tablet. The tablets are administered to a patient at the rate of 1 to 4 each day for treatment of a PI3K-mediated disorder or condition.

Formulation Example 2

Parenteral Solution

In a solution of 700 mL of propylene glycol and 200 mL of water for injection can be added 20.0 g of a compound of the present invention. The mixture is stirred, and the pH is adjusted to 5.5 with hydrochloric acid. The volume is adjusted to 1000 mL with water for injection. The solution is sterilized, filled into 5.0 mL ampules, each containing 2.0 mL (40 mg of invention compound), and sealed under nitrogen. The solution is administered by injection to a subject suffering from a PI3K-mediated disorder or condition and in need of treatment.

Formulation Example 3

Patch Formulation

Ten milligrams of a compound of the present invention can be mixed with 1 mL of propylene glycol and 2 mg of acrylic-based polymer adhesive containing a resinous cross-linking agent. The mixture is applied to an impermeable backing (30 cm$^2$) and applied to the upper back of a patient for sustained release treatment of a PI3K-mediated disorder or condition.

It is understood that the examples and embodiments described herein are for illustrative purposes only and that various modifications or changes in light thereof will be suggested to persons skilled in the art and are to be included within the spirit and purview of this application and the scope of the appended claims. All publications, patents, and patent applications cited herein are hereby incorporated by reference in their entirety for all purposes.

What is claimed is:

1. A compound of Formula I:

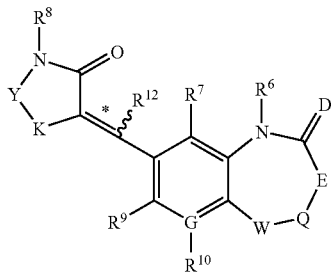

or a pharmaceutically acceptable salt thereof;
wherein $R^2$ and $R^3$ are independently selected from H or —CH$_3$,
wherein $R^6$ is selected from the group consisting of H, a —C(O)—C$_{1-9}$alkyl, a C$_{3-8}$cycloalkyl, a —C(O)—C$_{1-3}$ alkylene-C$_{3-8}$cycloalkyl, a (C$_{1-6}$alkyl)-C$_{3-8}$ cycloalkyl, a —O—CH$_2$—C$_{3-8}$cycloalkyl, a group of formula -A-B-L, and a group of formula —X—V—U-T,
wherein A is absent, or —O—,
wherein B is a C$_{1-6}$alkylene,
wherein L is —OR$^{24}$, —C(O)R$^{24}$, —OC(O)R$^{24}$, —SO$_2$—R$^{24}$, —NHC(O)R$^{24}$, —NR$^{24}$R$^{26}$, —C(O)—NR$^{24}$R$^{26}$, —OC(O)NR$^{24}$R$^{26}$, —NC(O) OR$^{24}$, a 3- to 8-membered heterocycloalkyl, a 6- to 11-membered bicyclic heterocycloalkyl, a 6- to 9-membered bridged bicyclic heterocycloalkyl, a 5-membered heteroaryl, a 6-membered heteroaryl, an 8-to 12-membered bicyclic heteroaryl, a naphthalenyl or a 9- to 12-membered bicyclic aryl;
wherein R$^{24}$ and R$^{26}$ are independently selected from the group consisting of: a C$_{1-6}$alkyl, phenyl, naphthalenyl or a 9- to 12-membered bicyclic aryl, a 5-membered heteroaryl, a 6-membered heteroaryl, an 8-to 12-membered bicyclic heteroaryl, a C$_{1-6}$alkylene-phenyl, C$_{1-6}$alkylene-naphthalenyl or a C$_{1-6}$alkylene-(9- to 12-membered bicyclic aryl), a C$_{1-6}$alkylene(5-membered heteroaryl), C$_{1-6}$alkylene(6-membered heteroaryl), a C$_{1-6}$alkylene(8- to 12-membered bicyclic heteroaryl), C$_{1-6}$alkylene-(3- to 8-membered heterocycloalkyl), C$_{1-6}$alkylene-(6- to 11-membered bicyclic heterocycloalkyl), C$_{1-6}$alkylene-(6- to 9-membered bridged bicyclic heterocycloalkyl), and H;
wherein X is C$_{1-3}$ alkylene, —O—C$_{1-3}$alkylene, —C$_{1-3}$ alkylene-CO—, —C$_{1-3}$ alkylene-C(O)O—, —C$_{1-3}$ alkylene-C(O)—CH$_2$—, —C$_1$-C$_3$ alkylene-O—, —C$_{1-3}$ alkylene-S(O)—, —C$_{1-3}$ alkylene-S—, or —C$_{1-3}$ alkylene-SO$_2$—;
wherein V is a 9- to 12-membered bicyclic arylene, a naphthalenylene, a phenylene, a 5-membered heteroarylene, a 6-membered heteroarylene, an 8- to 12-membered bicyclic heteroarylene, a 3- to 8-membered heterocycloalkylene, a 6- to 11-membered bicyclic heterocycloalkylene, or a 6- to 9-membered bridged bicyclic heterocycloalkylene;
wherein U is —CO—, —O—, —CH$_2$—O—, a C$_{1-3}$ alkenylene, —(CH$_2$)$_m$—, —O—CH$_2$—, NH—, or is absent,
wherein m is an integer from 1 to 3;
wherein T is a C$_{3-8}$cycloalkyl, a 9- to 12-membered bicyclic aryl, a naphthalenyl, a phenyl, a 5-membered heteroarylene, a 6-membered heteroarylene, an 8- to 12-membered bicyclic heteroarylene, a piperizinyl, a pyridinyl, a 3- to 8-membered heterocycloalkyl, a 6- to 11-membered bicyclic heterocycloalkyl, a 6- to 9-membered bridged bicyclic heterocycloalkyl, a piperidinyl, a morpholinyl, or an aza-spiro[5.5]undecyl;
wherein R$^7$ is H, F, CF$_3$, or CH$_3$;
wherein R$^8$ is H, —CH$_2$COOH, phenyl, —CH$_3$, a C$_{1-6}$alkyl, or a C$_{2-6}$alkenyl;
wherein Y is C(O), or C(S);
wherein K is NH, O, CH$_2$, or S;
wherein R$^9$ is H, F, CF$_3$, or CH$_3$;
wherein R$^{10}$ is H, —O—C$_{1-3}$alkyl, a C$_{1-3}$alkyl, NO$_2$, NR$^{16}$R$^{18}$, a S—C$_{1-3}$alkyl, F or Cl,
wherein R$^{16}$ and R$^{18}$ are independently selected from the group consisting of: H and C$_{1-3}$alkyl;
wherein R$^{12}$ is H, or C$_{1-3}$alkyl; and
wherein the stereochemistry of the double bond denoted "*" is E or Z.

2. The compound of claim 1, wherein R$^2$, R$^3$, R$^7$, R$^8$, R$^9$, R$^{10}$, and R$^{12}$ are H.

3. The compound of claim 2, wherein X is a C$_{1-3}$alkylene, and V is a phenylene, naphthalenylene, or a 9- to 12-membered bicyclic arylene.

4. The compound of claim 2, wherein X is a C$_{1-3}$alkylene, and V is a 5-membered heteroarylene, a 6-membered heteroarylene, or an 8- to 12-membered bicyclic heteroarylene.

5. The compound of claim 4, wherein V is selected from the group consisting of a 2-thienylene, a 3-thienylene, a 2-furanylene, a 3-furanylene, a pyrimidinylene and a pyridinylene.

6. The compound of claim 2, wherein A is absent, B is a C$_{1-3}$alkylene, wherein L is a 5-membered heteroaryl, a 6-membered heteroaryl, an 8- to 12-membered bicyclic heteroaryl, a naphthalenyl or a 9- to 12-membered bicyclic aryl.

7. The compound of claim 2, wherein K is S, Y is C(O), and R$^6$ is H.

8. The compound of claim 2, wherein K is S, Y is C(S), and R$^6$ is H.

9. The compound of claim 2, wherein K is NH, Y is C(O) and R$^6$ is H.

10. The compound of claim 2, wherein said compound is selected from the group consisting of:
4-(4-tert-Butyl-benzyl)-6-(4-oxo-2-thioxo-thiazolidin-5-ylidenemethyl)-4H-1,4-benzoxazin-3-one;
5-[4-(2,6-Di-tert-butyl-pyridin-4-ylmethyl)-3-oxo-3,4-dihydro-2H-1,4-benzoxazin-6-ylmethylene]-thiazolidine-2,4-dione;
6-(Oxo-2-thioxo-thiazolidin-5-ylidenmethyl)-4-[2-(4-trifluoromethyl-phenyl)-ethyl]-4H-benzo[1,4]oxazin-3-one;
4-(4-Methanesulfonyl-benzyl)-6-(4-oxo-2-thioxo-thiazolidin-5-ylidenemethyl)-4H-1,4-benzoxazin-3-one;
4-(3-tert-Butyl-5-hydroxymethyl-benzyl)-6-(4-oxo-2-thioxo-thiazolidin-5-ylidenemethyl)-4H-1,4-benzoxazin-3-one;
5-[4-(3,5-Di-tert-butyl-4-hydroxy-benzyl)-3-oxo-3,4-dihydro-2H-1,4-benzoxazin-6-ylmethylene]-thiazolidine-2,4-dione;

5-{4-[4-(4-Methyl-piperazin-1-ylmethyl)-benzyl]-3-oxo-3,4-dihydro-2H-1,4-benzoxazin-6-ylmethylene}-thiazolidine-2,4-dione;

4-Cyclohexylmethyl-6-(4-oxo-2-thioxo-oxazolidin-5-ylidenemethyl)-4H-1,4-benzoxazin-3-one;

4-[3-tert-Butyl-5-(morpholine-4-carbonyl)-benzyl]-6-(4-oxo-2-thioxo-thiazolidin-5-ylidenemethyl)-4H-1,4-benzoxazin-3-one;

5-[1-[4-(3-tert-Butyl-5-morpholin-4-ylmethyl-benzyl)-3-oxo-3,4-dihydro-2H-benzo[1,4]oxazin-6-yl]-meth-(Z)-ylidene]-thiazolidine-2,4-dione;

4-(3,5-Difluoro-4-hydroxy-benzyl)-6-(4-oxo-2-thioxo-thiazolidin-5-ylidenemethyl)-4H-benzo [1,4] oxazin-3-one;

5-[4-(3-Chloro-4-fluoro-benzyl)-3-oxo-3,4-dihydro-2H-benzo[1,4]oxazin-6-ylmethylene]-thiazolidine-2,4-dione; and 4-(1-tert-Butyl-5-methyl- 1H-pyrazol-3-ylmethyl)-6-(4-oxo-2-hioxo-thiazolidin-5-ylidenemethyl)-4H-benzo[1,4]oxazin-3-one.

11. The compound of claim 1, wherein $R^{10}$ is methoxy, and $R^2$, $R^3$, $R^7$, $R^8$, $R^9$, and $R^{12}$ are H.

12. The compound of claim 1, wherein $R^{10}$ is methyl, and $R^2$, $R^3$, $R^7$, $R^8$, $R^9$, and $R^{12}$ are H.

13. The compound of claim 1, wherein $R^7$ and $R^{10}$ are methyl, and $R^2$, $R^3$, $R^8$, $R^9$, and $R^{12}$ are H.

14. The compound of claim 1, wherein $R^{10}$ is chloro, and $R^2$, $R^3$, $R^7$, $R^8$, $R^9$, and $R^{12}$ are H.

15. The compound of claim 1, wherein $R^{10}$ is fluoro, and $R^2$, $R^3$, $R^7$, $R^8$, $R^9$, and $R^{12}$ are H.

16. The compound of claim 15, wherein said compound is selected from the group consisting of:

4-(3-Methanesulfonyl-benzyl)-6-[4-oxo-2-thioxo-thiazolidin-(5Z)-ylidenemethyl]-4H-benzo[1,4]oxazin-3-one;

5-[-{4-[3-tert-Butyl-5-(1-hydroxy-1-methyl-ethyl)-benzyl]-8-fluoro-3-oxo-3,4-dihydro-2H-benzo[1,4]oxazin-6-yl}-meth-(Z)-ylidene]-thiazolidine-2,4-dione;

8-Fluoro-4-[4-(1-hydroxy-1-methyl-ethyl)-benzyl]-6-(4-oxo-2-thioxo-thiazolidin-5-ylidenemethyl)-4H-benzo[1,4]oxazin-3-one;

5-[8-Fluoro-4-(4-fluoro-benzyl)-3-oxo-3,4-dihydro-2H-benzo[1,4]oxazin-6-ylmethylene]-thiazolidine-2,4-dione;

4-(3-Chloro-4-fluoro-benzyl)-8-fluoro-6-(4-oxo-2-thioxo-oxazolidin-5-ylidenemethyl)-4H-benzo[1,4]oxazin-3-one;

8-Fluoro-6-(4-oxo-2-thioxo-thiazolidin-5-ylidenemethyl)-4-quinolin-6-ylmethyl-4H-1,4-benzoxazin-3-one; and 4-(3,4-Dichloro-benzyl)-8-fluoro-6-(4-oxo-2-thioxo-thiazolidin-5-ylidenemethyl)-4H-benzo[1,4]oxazin-3-one.

17. The compound of claim 1, wherein $R^2$ is methyl, and $R^3$, $R^7$, $R^8$, $R^9$, $R^{10}$, and $R^{12}$ are H.

18. A pharmaceutical composition comprising:

a therapeutically effective amount of a compound of claim 1 and a pharmaceutically acceptable carrier.

19. A pharmaceutical composition comprising:

a therapeutically effective amount of a compound of any one of claims 1–10 or 11–17 and a pharmaceutically acceptable carrier.

* * * * *